United States Patent [19]

Bodor

[11] Patent Number: 5,624,894
[45] Date of Patent: Apr. 29, 1997

[54] BRAIN-ENHANCED DELIVERY OF NEUROACTIVE PEPTIDES BY SEQUENTIAL METABOLISM

[75] Inventor: Nicholas S. Bodor, Gainesville, Fla.

[73] Assignee: University of Florida, Gainesville, Fla.

[21] Appl. No.: 428,488

[22] Filed: Apr. 27, 1995

Related U.S. Application Data

[63] Continuation of Ser. No. 946,062, Sep. 17, 1992, abandoned.
[51] Int. Cl.$^6$ ..................................................... A61K 38/03
[52] U.S. Cl. ...................... 514/2; 546/134; 546/288; 546/290; 546/314; 514/15; 514/16; 514/17; 530/345
[58] Field of Search .................... 514/2, 12–17; 530/345; 546/315, 316, 286, 321, 134, 288, 290, 314

[56] References Cited

U.S. PATENT DOCUMENTS 4,540,564  9/1985  Bodor ........................................... 424/9
4,888,427  12/1989  Bodor ........................................... 546/316

FOREIGN PATENT DOCUMENTS

85/03937  9/1985  WIPO .

OTHER PUBLICATIONS

Bodor, et al, *J. Pharm. Sci.*, 67, No. 5, 685 (1978).
Bodor, "Novel Approaches for the *Design of Membrane Transport Properties of Drugs,*" in *Design of Biopharmaceutical Properties through Prodrugs and Analogs*, Roche, E.B. (ed.), APhA Academy of Pharmaceutical Sciences, Washington, D.C. 98–135 (1976).
Bodor et al, *Science*, vol. 214, Dec. 18, 1981, pp. 1370–1372.
Simpkins and Bodor, "Brain–Enhanced Drug Delivery Systems for the Treatment of Dementia," in *Alzheimer's Disease: New Treatment Strategies*, eds. Z.S. Khachaturian and J.P. Blass, Marcel Dekker, Inc., New York, 1992.
Guengerich et al, *J. Med. Chem.*, vol. 34, pp. 1838–1844 (1991).
Bodor et al, *Journal of Molecular Structure (Theochem)*, 206, pp. 315–334 (1990).
Bodor et al, *Journal of Molecular Structure (Theochem)*, 163, pp. 315–330 (1988).
Bodor et al, *Tetrahedron*, vol. 44, No. 24, pp. 7601–7610 (1988).
Brewster et al, *Fourth Colloquium in Biological Sciences: Blood–Brain Transfer*, vol. 529 of the Annals of the New York Academy of Sciences, pp. 298–300, Jun. 14, 1988.
Simpkins et al, Chapter 4 in *Alzheimer's Disease: New Treatment Strategies*, eds. Khachaturian and Blass, Marcel Dekker, Inc., New York, pp. 37–55 (1992).
Bodor et al, *Science*, vol. 257, pp. 1698–1700, Sep. 18, 1992.
Thomas, "Medical Progress: Top Ten Advances of 1992," in *Harvard Health Letter*, vol. 18, No. 5, pp. 1–4, Mar. 1993.
Pop et al, *International Journal of Pharmaceutics*, 84, pp. 39–48 (1992).
Bundgaard, Chapter 1 in *Design of Prodrugs*, ed. H. Bundgaard, pp. 1–10, 79–83 (1985).

*Primary Examiner*—David Lukton
*Attorney, Agent, or Firm*—Burns, Doane, Swecker & Mathis, L.L.P.

[57] ABSTRACT

The invention provides novel peptide derivatives which are designed to deliver pharmacologically active peptides into the central nervous system by sequential metabolism. The peptide is placed in a molecular environment which disguises its peptide nature and provides biolabile, lipophilic functions to penetrate the blood-brain barrier by passive transport. The design incorporates a dihydropyridine-type redox targetor moiety, an amino acid or di- or -tripeptide spacer inserted between the targetor and N-terminal amino acid unit of the peptide and a bulky, lipophilic substituent protecting the C-terminal amino acid unit of the peptide. The dihydropyridine-type targetor undergoes an enzymatically mediated oxidation to a hydrophilic, membrane-impermeable pyridinium salt. That polar targetor-peptide conjugate is trapped behind the lipoidal blood-brain barrier. Over time, cleavage of the lipophilic ester from the peptide by esterase and or lipase enzymes and enzymatic cleavage of the targetor-spacer from the peptide results in release of the desired peptide in the brain.

67 Claims, 5 Drawing Sheets

SEQUENCE LISTING ( 1 ) GENERAL INFORMATION:

( i i i ) NUMBER OF SEQUENCES: 107

( 2 ) INFORMATION FOR SEQ ID NO:1:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "Position 1 = p-Glu."

( x i ) SEQUENCE DESCRIPTION: SEQ ID NO:1:

Glu His Pro Gly
    1

( 2 ) INFORMATION FOR SEQ ID NO:2:

( i ) SEQUENCE CHARACTERISTICS:
        ( A ) LENGTH: 4 amino acids (B) TYPE: amino acid
(C) STRANDEDNESS: single
(D) TOPOLOGY: linear (i i) MOLECULE TYPE: peptide (x i) SEQUENCE DESCRIPTION: SEQ ID NO:2:

Gln His Pro Gly
1

(2) INFORMATION FOR SEQ ID NO:3:

(i) SEQUENCE CHARACTERISTICS:
(A) LENGTH: 4 amino acids
(B) TYPE: amino acid
(C) STRANDEDNESS: single
(D) TOPOLOGY: linear (i i) MOLECULE TYPE: peptide (x i) SEQUENCE DESCRIPTION: SEQ ID NO:3:

Gln Leu Pro Gly
1

(2) INFORMATION FOR SEQ ID NO:4:

(i) SEQUENCE CHARACTERISTICS:
(A) LENGTH: 5 amino acids
(B) TYPE: amino acid
(C) STRANDEDNESS: single
(D) TOPOLOGY: linear (i i) MOLECULE TYPE: peptide (i x) FEATURE:
(A) NAME/KEY: Modified-site
(B) LOCATION: 1
(D) OTHER INFORMATION: /note= "Position 1 = H-Tyr."

(i x) FEATURE:
(A) NAME/KEY: Modified-site
(B) LOCATION: 5
(D) OTHER INFORMATION: /note= "Position 5 = Met-OH."

(x i) SEQUENCE DESCRIPTION: SEQ ID NO:4:

Tyr Gly Gly Phe Met
1               5

(2) INFORMATION FOR SEQ ID NO:5:

(i) SEQUENCE CHARACTERISTICS:
(A) LENGTH: 5 amino acids
(B) TYPE: amino acid
(C) STRANDEDNESS: single
(D) TOPOLOGY: linear (i i) MOLECULE TYPE: peptide (i x) FEATURE:
(A) NAME/KEY: Modified-site
(B) LOCATION: 1
(D) OTHER INFORMATION: /note= "Position 1 = H-Tyr."

(i x) FEATURE:
(A) NAME/KEY: Modified-site
(B) LOCATION: 5
(D) OTHER INFORMATION: /note= "Position 5 = Leu-OH."

(x i) SEQUENCE DESCRIPTION: SEQ ID NO:5:

Tyr Gly Gly Phe Leu
1               5

( 2 ) INFORMATION FOR SEQ ID NO:6:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 2
        ( D ) OTHER INFORMATION: /note= "Position 2 = D-Ala."

( i x ) FEATURE:
        ( A ) NAME/KEY: Modified-site
        ( B ) LOCATION: 5
        ( D ) OTHER INFORMATION: /note= "Position 5 = D-Leu."

( x i ) SEQUENCE DESCRIPTION: SEQ ID NO:6:

Tyr  Ala  Gly  Phe  Leu
1                          5

( 2 ) INFORMATION FOR SEQ ID NO:7:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "Amino acid 1 is disulfide bonded."

( i x ) FEATURE:
        ( A ) NAME/KEY: Modified-site
        ( B ) LOCATION: 6
        ( D ) OTHER INFORMATION: /note= "Amino acid 6 is disulfide bonded."

( i x ) FEATURE:
        ( A ) NAME/KEY: Modified-site
        ( B ) LOCATION: 9
        ( D ) OTHER INFORMATION: /note= "Position 9 = Gly-NH2."

( x i ) SEQUENCE DESCRIPTION: SEQ ID NO:7:

Cys  Tyr  Ile  Gln  Asn  Cys  Pro  Leu  Gly
1                          5

( 2 ) INFORMATION FOR SEQ ID NO:8:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "Amino acid 1 is disulfide bonded."

( i x ) FEATURE:
        ( A ) NAME/KEY: Modified-site
        ( B ) LOCATION: 6
        ( D ) OTHER INFORMATION: /note= "Amino acid 6 is disulfide bonded."

( i x ) FEATURE:
  ( A ) NAME/KEY: Modified-site
  ( B ) LOCATION: 9
  ( D ) OTHER INFORMATION: /note= "Position 9 = Gly-NH2."

( x i ) SEQUENCE DESCRIPTION: SEQ ID NO:8:

Cys Tyr Phe Gln Asn Cys Pro Arg Gly
1       5

( 2 ) INFORMATION FOR SEQ ID NO:9:

( i ) SEQUENCE CHARACTERISTICS:
  ( A ) LENGTH: 9 amino acids
  ( B ) TYPE: amino acid
  ( C ) STRANDEDNESS: single
  ( D ) TOPOLOGY: linear ( i i ) MOLECULE TYPE: peptide ( i x ) FEATURE:
  ( A ) NAME/KEY: Modified-site
  ( B ) LOCATION: 1
  ( D ) OTHER INFORMATION: /note= "Amino acid 1 is disulfide bonded."

( i x ) FEATURE:
  ( A ) NAME/KEY: Modified-site
  ( B ) LOCATION: 6
  ( D ) OTHER INFORMATION: /note= "Amino acid 6 is disulfide bonded."

( i x ) FEATURE:
  ( A ) NAME/KEY: Modified-site
  ( B ) LOCATION: 9
  ( D ) OTHER INFORMATION: /note= "Position 9 = Gly-NH2."

( x i ) SEQUENCE DESCRIPTION: SEQ ID NO:9:

Cys Tyr Phe Gln Asn Cys Pro Lys Gly
1       5

( 2 ) INFORMATION FOR SEQ ID NO:10:

( i ) SEQUENCE CHARACTERISTICS:
  ( A ) LENGTH: 7 amino acids
  ( B ) TYPE: amino acid
  ( C ) STRANDEDNESS: single
  ( D ) TOPOLOGY: linear ( i i ) MOLECULE TYPE: peptide ( i x ) FEATURE:
  ( A ) NAME/KEY: Modified-site
  ( B ) LOCATION: 1
  ( D ) OTHER INFORMATION: /note= "Amino acid 1 is disulfide bonded."

( i x ) FEATURE:
  ( A ) NAME/KEY: Modified-site
  ( B ) LOCATION: 6
  ( D ) OTHER INFORMATION: /note= "Amino acid 6 is disulfide bonded."

( i x ) FEATURE:
  ( A ) NAME/KEY: Modified-site
  ( B ) LOCATION: 7
  ( D ) OTHER INFORMATION: /note= "Position 7 = Pro-OH."

( x i ) SEQUENCE DESCRIPTION: SEQ ID NO:10:

Cys Tyr Phe Gln Asn Cys Pro
1     5

( 2 ) INFORMATION FOR SEQ ID NO:11:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "Position 1 = p-Glu."

( i x ) FEATURE:
        ( A ) NAME/KEY: Modified-site
        ( B ) LOCATION: 13
        ( D ) OTHER INFORMATION: /note= "Position 13 = Leu-OH."

( x i ) SEQUENCE DESCRIPTION: SEQ ID NO:11:

Glu Leu Tyr Glu Asn Lys Pro Arg Arg Pro Tyr Ile Leu
    1                5                              10

( 2 ) INFORMATION FOR SEQ ID NO:12:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "Position 1 = p-Glu."

( i x ) FEATURE:
        ( A ) NAME/KEY: Modified-site
        ( B ) LOCATION: 8
        ( D ) OTHER INFORMATION: /note= "Position 8 = Leu-OH."

( x i ) SEQUENCE DESCRIPTION: SEQ ID NO:12:

Glu Gly Lys Arg Pro Trp Ile Leu
    1                5

( 2 ) INFORMATION FOR SEQ ID NO:13:

( i ) SEQUENCE CHARACTERISTICS:
        ( A ) LENGTH: 39 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "Position 1 = H-Ser."

( i x ) FEATURE:
        ( A ) NAME/KEY: Modified-site
        ( B ) LOCATION: 39
        ( D ) OTHER INFORMATION: /note= "Position 39 = Phe-OH."

( i x ) FEATURE:
        ( A ) NAME/KEY: Modified-site
        ( B ) LOCATION: 30
        ( D ) OTHER INFORMATION: /note= "Position 30 = Glu-NH2."

( x i ) SEQUENCE DESCRIPTION: SEQ ID NO:13:

Ser Tyr Ser Met Glu His Phe Arg Tyr Gly Lys Pro Val Gly Lys Lys

```
        1               5                   10                  15
      Arg Arg Pro Val Lys Val Tyr Pro Asp Gly Ala Glu Asp Glu Leu Ala
                      20                  25                  30

Glu Ala Phe Pro Leu Glu Phe
                  35
```

( 2 ) INFORMATION FOR SEQ ID NO:14:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "Position 1 = H-Met(O)."

( i x ) FEATURE:
        ( A ) NAME/KEY: Modified-site
        ( B ) LOCATION: 5
        ( D ) OTHER INFORMATION: /note= "Position 5 = D-Lys."

( i x ) FEATURE:
        ( A ) NAME/KEY: Modified-site
        ( B ) LOCATION: 6
        ( D ) OTHER INFORMATION: /note= "Position 6 = Phe-OH."

( x i ) SEQUENCE DESCRIPTION: SEQ ID NO:14:

```
      Met Glu His Phe Lys Phe
      1               5
```

( 2 ) INFORMATION FOR SEQ ID NO:15:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "Position 1 = H-Arg."

( i x ) FEATURE:
        ( A ) NAME/KEY: Modified-site
        ( B ) LOCATION: 5
        ( D ) OTHER INFORMATION: /note= "Position 5 = Glu-NH2."

( i x ) FEATURE:
        ( A ) NAME/KEY: Modified-site
        ( B ) LOCATION: 6
        ( D ) OTHER INFORMATION: /note= "Position 6 = Glu-NH2."

( x i ) SEQUENCE DESCRIPTION: SEQ ID NO:15:

```
      Arg Pro Lys Pro Glu Glu Phe Phe Gly Leu Met
      1               5                   10
```

( 2 ) INFORMATION FOR SEQ ID NO:16:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note= "Position 1 = p-Glu."

( i x ) FEATURE:
    ( A ) NAME/KEY: Modified-site
    ( B ) LOCATION: 11
    ( D ) OTHER INFORMATION: /note= "Position 11 = Met-NH2."

( x i ) SEQUENCE DESCRIPTION: SEQ ID NO:16:

Glu Ala Asp Pro Asn Lys Phe Tyr Gly Leu Met
1               5                   10

( 2 ) INFORMATION FOR SEQ ID NO:17:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "Position 1 = p-Glu."

( i x ) FEATURE:
        ( A ) NAME/KEY: Modified-site
        ( B ) LOCATION: 11
        ( D ) OTHER INFORMATION: /note= "Position 11 = Met-NH2."

( x i ) SEQUENCE DESCRIPTION: SEQ ID NO:17:

Glu Pro Ser Lys Asp Ala Phe Ile Gly Leu Met
1               5                   10

( 2 ) INFORMATION FOR SEQ ID NO:18:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 12
        ( D ) OTHER INFORMATION: /note= "Position 12 = Met-NH2."

( x i ) SEQUENCE DESCRIPTION: SEQ ID NO:18:

Asp Val Pro Lys Ser Asp Gln Phe Val Gly Leu Met
1               5                   10

( 2 ) INFORMATION FOR SEQ ID NO:19:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "Position 1 = Val with a
            hydrogen atom or a terminal nitrogen protecting group
            of acyl, aliphatic urethane, aromatic urethane, alkyl or aralkyl type."

(ix) FEATURE:
 (A) NAME/KEY: Modified-site
 (B) LOCATION: 7
 (D) OTHER INFORMATION: /note= "Position 7 = a neutral
  L-alpha- amino acid residue with a hydroxy group, an
  amino group or a group of the formula OR, NHR, NR2 or
  NH-N-H-R' wherein R and R' are defined on page 48 of
  the specification."

(xi) SEQUENCE DESCRIPTION: SEQ ID NO:19:

Val Pro Pro Leu Gly Trp Xaa
1     5

(2) INFORMATION FOR SEQ ID NO:20:

(i) SEQUENCE CHARACTERISTICS:
  (A) LENGTH: 10 amino acids
  (B) TYPE: amino acid
  (C) STRANDEDNESS: single
  (D) TOPOLOGY: linear (ii) MOLECULE TYPE: peptide (ix) FEATURE:
  (A) NAME/KEY: Modified-site
  (B) LOCATION: 1
  (D) OTHER INFORMATION: /note= "Position 1 = H-Asp."

(ix) FEATURE:
  (A) NAME/KEY: Modified-site
  (B) LOCATION: 10
  (D) OTHER INFORMATION: /note= "Position 10 = Leu-OH."

(xi) SEQUENCE DESCRIPTION: SEQ ID NO:20:

Asp Arg Val Tyr Ile His Pro Phe His Leu
1     5         10

(2) INFORMATION FOR SEQ ID NO:21:

(i) SEQUENCE CHARACTERISTICS:
  (A) LENGTH: 8 amino acids
  (B) TYPE: amino acid
  (C) STRANDEDNESS: single
  (D) TOPOLOGY: linear (ii) MOLECULE TYPE: peptide (ix) FEATURE:
  (A) NAME/KEY: Modified-site
  (B) LOCATION: 1
  (D) OTHER INFORMATION: /note= "Position 1 = H-Asp."

(ix) FEATURE:
  (A) NAME/KEY: Modified-site
  (B) LOCATION: 8
  (D) OTHER INFORMATION: /note= "Position 8 = Phe-OH."

(xi) SEQUENCE DESCRIPTION: SEQ ID NO:21:

Asp Arg Val Tyr Ile His Pro Phe
1     5

(2) INFORMATION FOR SEQ ID NO:22:

(i) SEQUENCE CHARACTERISTICS:
  (A) LENGTH: 10 amino acids
  (B) TYPE: amino acid
  (C) STRANDEDNESS: single
  (D) TOPOLOGY: linear (ii) MOLECULE TYPE: peptide (ix) FEATURE:

(A) NAME/KEY: Modified-site
(B) LOCATION: 1
(D) OTHER INFORMATION: /note= "Position 1 = p-Glu."

(ix) FEATURE:
(A) NAME/KEY: Modified-site
(B) LOCATION: 10
(D) OTHER INFORMATION: /note= "Position 10 = Gly-NH2."

(xi) SEQUENCE DESCRIPTION: SEQ ID NO:22:

```
Glu His Trp Ser Tyr Gly Leu Arg Pro Gly
1             5                      10
```

(2) INFORMATION FOR SEQ ID NO:23:

(i) SEQUENCE CHARACTERISTICS:
(A) LENGTH: 10 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1
(D) OTHER INFORMATION: /note= "Position 1 = p-Glu."(ix)
FEATURE:
(A) NAME/KEY: Modified-site
(B) LOCATION: 3
(D) OTHER INFORMATION: /note= "Position 3 = tryptophyl,
phenylalanyl, 3-(1-naphthyl)-L-alanyl or
3-(2- naphthyl)-L-alanyl."

(ix) FEATURE:
(A) NAME/KEY: Modified-site
(B) LOCATION: 5
(D) OTHER INFORMATION: /note= "Position 5 = tyrosyl,
phenylalanyl or 3-(1-pentafluoro-phenyl)-L-alanyl."

(ix) FEATURE:
(A) NAME/KEY: Modified-site
(B) LOCATION: 6
(D) OTHER INFORMATION: /note= "Position 6 = amino acyl residue
selected from the group consisting of radicals
represented by structural formulas described on pages
51-53 of the specification."

(ix) FEATURE:
(A) NAME/KEY: Modified-site
(B) LOCATION: 7
(D) OTHER INFORMATION: /note= "Position 7 = leucyl, isoleucyl,
nor-leucyl, N-methyl-leucyl or tryptophanyl."

(ix) FEATURE:
(A) NAME/KEY: Modified-site
(B) LOCATION: 8
(D) OTHER INFORMATION: /note= "Position 8 = arginyl or
leucyl."

(ix) FEATURE:
(A) NAME/KEY: Modified-site
(B) LOCATION: 10
(D) OTHER INFORMATION: /note= "Position 10 = glycinamide
or -NH-R1 wherein R1 is lower alkyl, cycloalkyl,
fluoro lower alkyl or -NH-CO-NH- R2 wherein R is
hydrogen or lower alkyl."

(xi) SEQUENCE DESCRIPTION: SEQ ID NO:23:

```
Glu His Xaa Ser Xaa Xaa Xaa Xaa Pro Xaa
1             5                      10
```

(2) INFORMATION FOR SEQ ID NO:24:

(i) SEQUENCE CHARACTERISTICS:
(A) LENGTH: 10 amino acids (B) TYPE: amino acid
(C) STRANDEDNESS: single
(D) TOPOLOGY: linear (ii) MOLECULE TYPE: peptide (ix) FEATURE:
    (A) NAME/KEY: Modified-site
    (B) LOCATION: 1
    (D) OTHER INFORMATION: /note= "Position 1 = dehydro-Pro, Pro, D-pGlu, D- Phe, D-Trp or beta-D-NAL attached to hydrogen or an acyl group having 7 or less carbon atoms."

(ix) FEATURE:
    (A) NAME/KEY: Modified-site
    (B) LOCATION: 2
    (D) OTHER INFORMATION: /note= "Position 2 = D-Phe attached to F, Cl, Cl2Br, NO2 or CalphaMeCl."

(ix) FEATURE:
    (A) NAME/KEY: Modified-site
    (B) LOCATION: 3
    (D) OTHER INFORMATION: /note= "Position 3 = D-Trp, (N in For )D-Trp or D-Trp which is substituted in the 5- or 6- position with NO2, NH2, OCH3, F, Cl, Br or CH3."

(ix) FEATURE:
    (A) NAME/KEY: Modified-site
    (B) LOCATION: 4
    (D) OTHER INFORMATION: /note= "Position 4 = Ser, Orn, AAL or aBu."

(ix) FEATURE:
    (A) NAME/KEY: Modified-site
    (B) LOCATION: 5
    (D) OTHER INFORMATION: /note= "Position 5 = Tyr, (3F)Phe, (2 F )Phe, (3I)Tyr, (3CH3)Phe, (2CH3)Phe, (2CH3)Phe, (3 C l )Phe or (2Cl)Phe."

(ix) FEATURE:
    (A) NAME/KEY: Modified-site
    (B) LOCATION: 6
    (D) OTHER INFORMATION: /note= "Position 6 = D-Lys, D-Orn or D-Dap attached to arg-R', R"n(X), with n being 1 to 5 and R'and R"being H, methyl, ethyl, propyl or butyl."

(ix) FEATURE:
    (A) NAME/KEY: Modified-site
    (B) LOCATION: 7
    (D) OTHER INFORMATION: /note= "Position 7 - Leu, NML, Nle or Nva."

(ix) FEATURE:
    (A) NAME/KEY: Modified-site
    (B) LOCATION: 10
    (D) OTHER INFORMATION: /note= "Position 10 = Gly-NH2, D- Ala-NH2 or NH-Y."

(xi) SEQUENCE DESCRIPTION: SEQ ID NO:24:

```
Xaa  Phe  Xaa  Xaa  Xaa  Xaa  Xaa  Arg  Pro  Xaa
1                  5                            10
```

(2) INFORMATION FOR SEQ ID NO:25:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (ix) FEATURE:
    (A) NAME/KEY: Modified-site
    (B) LOCATION: 1
    (D) OTHER INFORMATION: /note= "Position 1 = dehydro-Pro, D-pGlu, D- Phe, D-Trp or beta-D-NAL attached to hydrogen or an acyl group having 7 or less carbon atoms."

( i x ) FEATURE:
  ( A ) NAME/KEY: Modified-site
  ( B ) LOCATION: 2
  ( D ) OTHER INFORMATION: /note= "Position 2 = Phe attached to F, Cl, Cl2Br, NO2 or CalphaMeCl."

( i x ) FEATURE:
  ( A ) NAME/KEY: Modified-site
  ( B ) LOCATION: 3
  ( D ) OTHER INFORMATION: /note= "Position 3 = (NinFor)D-Trp or D-Trp which is substituted in the 5- or 6-position with NO2, NH2, OCH3, F, Cl, Br or CH3."

( i x ) FEATURE:
  ( A ) NAME/KEY: Modified-site
  ( B ) LOCATION: 4
  ( D ) OTHER INFORMATION: /note= "Position 4 = Ser, Orn, or aBu."

( i x ) FEATURE:
  ( A ) NAME/KEY: Modified-site
  ( B ) LOCATION: 5
  ( D ) OTHER INFORMATION: /note= "Position 5 = Tyr, Arg, ( 3 F )Phe, (2F)Phe, (3I)Tyr, (3CH3)Phe, (2CH3)Phe, ( 3 C l )Phe or (2Cl)Phe."

( i x ) FEATURE:
  ( A ) NAME/KEY: Modified-site
  ( B ) LOCATION: 6
  ( D ) OTHER INFORMATION: /note= "Position 6 = A(4NH2)D- Phe, D-Lys, D-Orn, D-Har, D-His, (4gua)D-Phe, D-Tyr, a D- isomer of lipophilic amino or D-arg."

( i x ) FEATURE:
  ( A ) NAME/KEY: Modified-site
  ( B ) LOCATION: 7
  ( D ) OTHER INFORMATION: /note= "Position 7 = Leu, NML, or Nva."

( i x ) FEATURE:
  ( A ) NAME/KEY: Modified-site
  ( B ) LOCATION: 10
  ( D ) OTHER INFORMATION: /note= "Position 10 = Gly-NH2, D-Ala-NH2 or NH-Y wherein Y defined on page 55 of the specification."

( x i ) SEQUENCE DESCRIPTION: SEQ ID NO:25:

Xaa Phe Xaa Xaa Xaa Xaa Xaa Arg Pro Xaa
1               5                       10

( 2 ) INFORMATION FOR SEQ ID NO:26:

( i ) SEQUENCE CHARACTERISTICS:
    ( A ) LENGTH: 5 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION: 2
    ( D ) OTHER INFORMATION: /note= "Position 2 = D-Ala."

( i x ) FEATURE:
    ( A ) NAME/KEY: Modified-site
    ( B ) LOCATION: 5
    ( D ) OTHER INFORMATION: /note= "Position 5 = D-Leu."

( x i ) SEQUENCE DESCRIPTION: SEQ ID NO:26:

Tyr Ala Gly Phe Leu
1               5

( 2 ) INFORMATION FOR SEQ ID NO:27:

( i ) SEQUENCE CHARACTERISTICS:
   ( A ) LENGTH: 5 amino acids
   ( B ) TYPE: amino acid
   ( C ) STRANDEDNESS: single
   ( D ) TOPOLOGY: linear ( i i ) MOLECULE TYPE: peptide ( i x ) FEATURE:
   ( A ) NAME/KEY: Modified-site
   ( B ) LOCATION: 2
   ( D ) OTHER INFORMATION: /note= "Position 2 = D-Ala."

( x i ) SEQUENCE DESCRIPTION: SEQ ID NO:27:

Tyr Ala Gly Phe Leu
1               5

( 2 ) INFORMATION FOR SEQ ID NO:28:

( i ) SEQUENCE CHARACTERISTICS:
      ( A ) LENGTH: 5 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:28:

Tyr Ala Gly Phe Leu
1               5

( 2 ) INFORMATION FOR SEQ ID NO:29:

( i ) SEQUENCE CHARACTERISTICS:
      ( A ) LENGTH: 6 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:29:

Ala Tyr Ala Gly Phe Leu
1               5

( 2 ) INFORMATION FOR SEQ ID NO:30:

( i ) SEQUENCE CHARACTERISTICS:
      ( A ) LENGTH: 4 amino acids
      ( B ) TYPE: amino acid
      ( C ) STRANDEDNESS: single
      ( D ) TOPOLOGY: linear ( i i ) MOLECULE TYPE: peptide ( i x ) FEATURE:
      ( A ) NAME/KEY: Modified-site
      ( B ) LOCATION: 1
      ( D ) OTHER INFORMATION: /note= "Position 1 = Boc-Gln."

( i x ) FEATURE:
      ( A ) NAME/KEY: Modified-site
      ( B ) LOCATION: 4
      ( D ) OTHER INFORMATION: /note= "Position 4 = Gly-Cholesteryl
            ester."

( x i ) SEQUENCE DESCRIPTION: SEQ ID NO:30:

Gln Leu Pro Gly
1

( 2 ) INFORMATION FOR SEQ ID NO:31:

( i ) SEQUENCE CHARACTERISTICS:
   ( A ) LENGTH: 4 amino acids
   ( B ) TYPE: amino acid
   ( C ) STRANDEDNESS: single
   ( D ) TOPOLOGY: linear ( i i ) MOLECULE TYPE: peptide ( i x ) FEATURE:
   ( A ) NAME/KEY: Modified-site
   ( B ) LOCATION: 4
   ( D ) OTHER INFORMATION: /note= "Position 4 = Gly-Cholesteryl ester."

( x i ) SEQUENCE DESCRIPTION: SEQ ID NO:31:

Gln Leu Pro Gly
1

( 2 ) INFORMATION FOR SEQ ID NO:32:

( i ) SEQUENCE CHARACTERISTICS:
      ( A ) LENGTH: 5 amino acids
      ( B ) TYPE: amino acid
      ( C ) STRANDEDNESS: single
      ( D ) TOPOLOGY: linear ( i i ) MOLECULE TYPE: peptide ( i x ) FEATURE:
      ( A ) NAME/KEY: Modified-site
      ( B ) LOCATION: 1
      ( D ) OTHER INFORMATION: /note= "Position 1 = Boc-Ala."

( i x ) FEATURE:
      ( A ) NAME/KEY: Modified-site
      ( B ) LOCATION: 5
         bonded."
      ( D ) OTHER INFORMATION: /note= "Position 5 = Gly-Cholesteryl ester."

( x i ) SEQUENCE DESCRIPTION: SEQ ID NO:32:

Ala Gln Leu Pro Gly
1               5

( 2 ) INFORMATION FOR SEQ ID NO:33:

( i ) SEQUENCE CHARACTERISTICS:
      ( A ) LENGTH: 5 amino acids
      ( B ) TYPE: amino acid
      ( C ) STRANDEDNESS: single
      ( D ) TOPOLOGY: linear ( i i ) MOLECULE TYPE: peptide ( i x ) FEATURE:
      ( A ) NAME/KEY: Modified-site
      ( B ) LOCATION: 5
      ( D ) OTHER INFORMATION: /note= "Position 5 = Gly-Cholesteryl ester."

( x i ) SEQUENCE DESCRIPTION: SEQ ID NO:33:

Ala Gln Leu Pro Gly
1               5

( 2 ) INFORMATION FOR SEQ ID NO:34:

( i ) SEQUENCE CHARACTERISTICS:
      ( A ) LENGTH: 5 amino acids
      ( B ) TYPE: amino acid
      ( C ) STRANDEDNESS: single
      ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note= "Position 1 = nicotinoyl-Ala."

( i x ) FEATURE:
    ( A ) NAME/KEY: Modified-site
    ( B ) LOCATION: 5
    ( D ) OTHER INFORMATION: /note= "Position 5 = Gly-Cholesteryl ester."

( x i ) SEQUENCE DESCRIPTION: SEQ ID NO:34:

Ala Gln Leu Pro Gly
1                5

( 2 ) INFORMATION FOR SEQ ID NO:35:

( i ) SEQUENCE CHARACTERISTICS:
    ( A ) LENGTH: 5 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note= "Position 1 = 1,4- Dihydrotrigonellyl-Ala methylsulfate.

( i x ) FEATURE:
    ( A ) NAME/KEY: Modified-site
    ( B ) LOCATION: 5
    ( D ) OTHER INFORMATION: /note= "Position 5 = Gly-Cholesteryl ester."

( x i ) SEQUENCE DESCRIPTION: SEQ ID NO:35:

Ala Gln Leu Pro Gly
1                5

( 2 ) INFORMATION FOR SEQ ID NO:36:

( i ) SEQUENCE CHARACTERISTICS:
    ( A ) LENGTH: 5 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note= "Position 1 = 1,4- Dihydrotrigonellyl-Ala."

( i x ) FEATURE:
    ( A ) NAME/KEY: Modified-site
    ( B ) LOCATION: 5
    ( D ) OTHER INFORMATION: /note= "Position 5 = Gly- Cholesteryl ester."

( x i ) SEQUENCE DESCRIPTION: SEQ ID NO:36:

Ala Gln Leu Pro Gly
1                5

( 2 ) INFORMATION FOR SEQ ID NO:37:

( i ) SEQUENCE CHARACTERISTICS:
    ( A ) LENGTH: 6 amino acids
    ( B ) TYPE: amino acid
    ( C ) STRANDEDNESS: single (D) TOPOLOGY: linear (ii) MOLECULE TYPE: peptide (ix) FEATURE:
                (A) NAME/KEY: Modified-site
                (B) LOCATION: 1
                (D) OTHER INFORMATION: /note= "Position 1 = Boc-Ala."

(ix) FEATURE:
                (A) NAME/KEY: Modified-site
                (B) LOCATION: 6
                (D) OTHER INFORMATION: /note= "Position 6 = Gly-Cholesteryl
                        ester."

(xi) SEQUENCE DESCRIPTION: SEQ ID NO:37:

Ala  Ala  Gln  Leu  Pro  Gly
        1                   5

(2) INFORMATION FOR SEQ ID NO:38:

(i) SEQUENCE CHARACTERISTICS:
                (A) LENGTH: 6 amino acids
                (B) TYPE: amino acid
                (C) STRANDEDNESS: single
                (D) TOPOLOGY: linear (ii) MOLECULE TYPE: peptide (ix) FEATURE:
                (A) NAME/KEY: Modified-site
                (B) LOCATION: 6
                (D) OTHER INFORMATION: /note= "Position 6 = Gly-Cholesteryl
                        ester."

(xi) SEQUENCE DESCRIPTION: SEQ ID NO:38:

Ala  Ala  Gln  Leu  Pro  Gly
        1                   5

(2) INFORMATION FOR SEQ ID NO:39:

(i) SEQUENCE CHARACTERISTICS:
                (A) LENGTH: 6 amino acids
                (B) TYPE: amino acid
                (C) STRANDEDNESS: single
                (D) TOPOLOGY: linear (ii) MOLECULE TYPE: peptide (ix) FEATURE:
                (A) NAME/KEY: Modified-site
                (B) LOCATION: 1
                (D) OTHER INFORMATION: /note= "Position 1 = nicotinoyl-Ala."

(ix) FEATURE:
                (A) NAME/KEY: Modified-site
                (B) LOCATION: 6
                (D) OTHER INFORMATION: /note= "Position 6 = Gly-Cholesteryl
                        ester."

(xi) SEQUENCE DESCRIPTION: SEQ ID NO:39:

Ala  Ala  Gln  Leu  Pro  Gly
        1                   5

(2) INFORMATION FOR SEQ ID NO:40:

(i) SEQUENCE CHARACTERISTICS:
                (A) LENGTH: 6 amino acids
                (B) TYPE: amino acid
                (C) STRANDEDNESS: single
                (D) TOPOLOGY: linear (ii) MOLECULE TYPE: peptide

```
        ( i x ) FEATURE:
                ( A ) NAME/KEY: Modified-site
                ( B ) LOCATION: 1
                ( D ) OTHER INFORMATION: /note= "Position 1 =
                        1,4- Dihydrotrigonellyl-Ala methylsulfate."

( i x ) FEATURE:
                ( A ) NAME/KEY: Modified-site
                ( B ) LOCATION: 6
                ( D ) OTHER INFORMATION: /note= "Position 6 = Gly-Cholesteryl
                        ester."

( x i ) SEQUENCE DESCRIPTION: SEQ ID NO:40:

Ala  Ala  Gln  Leu  Pro  Gly
    1                    5

( 2 ) INFORMATION FOR SEQ ID NO:41:

( i ) SEQUENCE CHARACTERISTICS:
                ( A ) LENGTH: 6 amino acids
                ( B ) TYPE: amino acid
                ( C ) STRANDEDNESS: single
                ( D ) TOPOLOGY: linear ( i i ) MOLECULE TYPE: peptide ( i x ) FEATURE:
                ( A ) NAME/KEY: Modified-site
                ( B ) LOCATION: 1
                ( D ) OTHER INFORMATION: /note= "Position 1 =
                        1,4- Dihydrotrigonellyl-Ala."

( i x ) FEATURE:
                ( A ) NAME/KEY: Modified-site
                ( B ) LOCATION: 6
                ( D ) OTHER INFORMATION: /note= "Position 6 = Gly-Cholesteryl
                        ester."

( x i ) SEQUENCE DESCRIPTION: SEQ ID NO:41:

Ala  Ala  Gln  Leu  Pro  Gly
    1                    5

( 2 ) INFORMATION FOR SEQ ID NO:42:

( i ) SEQUENCE CHARACTERISTICS:
                ( A ) LENGTH: 6 amino acids
                ( B ) TYPE: amino acid
                ( C ) STRANDEDNESS: single
                ( D ) TOPOLOGY: linear ( i i ) MOLECULE TYPE: peptide ( i x ) FEATURE:
                ( A ) NAME/KEY: Modified-site
                ( B ) LOCATION: 1
                ( D ) OTHER INFORMATION: /note= "Position 1 =
                        1,4- dihydrotrigonellyl-Pro."

( i x ) FEATURE:
                ( A ) NAME/KEY: Modified-site
                ( B ) LOCATION: 6
                ( D ) OTHER INFORMATION: /note= "Position 6 = Gly-Cholesteryl
                        ester."

( x i ) SEQUENCE DESCRIPTION: SEQ ID NO:42:

Pro  Ala  Gln  Leu  Pro  Gly
    1                    5

( 2 ) INFORMATION FOR SEQ ID NO:43:

( i ) SEQUENCE CHARACTERISTICS:
                ( A ) LENGTH: 5 amino acids
                ( B ) TYPE: amino acid
                ( C ) STRANDEDNESS: single
```

( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note= "Position 1 = Boc-Pro."

( i x ) FEATURE:
    ( A ) NAME/KEY: Modified-site
    ( B ) LOCATION: 5
    ( D ) OTHER INFORMATION: /note= "Position 5 = Gly-Cholesteryl ester."

( x i ) SEQUENCE DESCRIPTION: SEQ ID NO:43:

Pro Gln Leu Pro Gly
1                 5

( 2 ) INFORMATION FOR SEQ ID NO:44:

( i ) SEQUENCE CHARACTERISTICS:
    ( A ) LENGTH: 5 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION: 5
    ( D ) OTHER INFORMATION: /note= "Position 5 = Gly-Cholesteryl ester."

( x i ) SEQUENCE DESCRIPTION: SEQ ID NO:44:

Pro Gln Leu Pro Gly
1                 5

( 2 ) INFORMATION FOR SEQ ID NO:45:

( i ) SEQUENCE CHARACTERISTICS:
    ( A ) LENGTH: 5 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note= "Position 1 = nicotinoyl-Pro."

( i x ) FEATURE:
    ( A ) NAME/KEY: Modified-site
    ( B ) LOCATION: 5
    ( D ) OTHER INFORMATION: /note= "Position 5 = Gly-Cholesteryl ester."

( x i ) SEQUENCE DESCRIPTION: SEQ ID NO:45:

Pro Gln Leu Pro Gly
1                 5

( 2 ) INFORMATION FOR SEQ ID NO:46:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note= "Position 1 = Boc-Ala."

( i x ) FEATURE:
    ( A ) NAME/KEY: Modified-site
    ( B ) LOCATION: 6
    ( D ) OTHER INFORMATION: /note= "Position 6 = Gly-Cholesteryl ester."

( x i ) SEQUENCE DESCRIPTION: SEQ ID NO:46:

Ala Pro Gln Leu Pro Gly
1                   5

( 2 ) INFORMATION FOR SEQ ID NO:47:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 6
        ( D ) OTHER INFORMATION: /note= "Position 6 = Gly-Cholesteryl ester."

( x i ) SEQUENCE DESCRIPTION: SEQ ID NO:47:

Ala Pro Gln Leu Pro Gly
1                   5

( 2 ) INFORMATION FOR SEQ ID NO:48:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "Position 1 = nicotinoyl-Ala."

( i x ) FEATURE:
        ( A ) NAME/KEY: Modified-site
        ( B ) LOCATION: 6
        ( D ) OTHER INFORMATION: /note= "Position 6 = Gly-Cholesteryl ester."

( x i ) SEQUENCE DESCRIPTION: SEQ ID NO:48:

Ala Pro Gln Leu Pro Gly
1                   5

( 2 ) INFORMATION FOR SEQ ID NO:49:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "Position 1 = Boc-Pro."

( i x ) FEATURE:
    ( A ) NAME/KEY: Modified-site
    ( B ) LOCATION: 6
    ( D ) OTHER INFORMATION: /note= "Position 6 = Gly-Cholesteryl ester."

( x i ) SEQUENCE DESCRIPTION: SEQ ID NO:49:

Pro Pro Gln Leu Pro Gly
1                   5

( 2 ) INFORMATION FOR SEQ ID NO:50:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 6
        ( D ) OTHER INFORMATION: /note= "Position 6 = Gly-Cholesteryl ester."

( x i ) SEQUENCE DESCRIPTION: SEQ ID NO:50:

Pro Pro Gln Leu Pro Gly
1                   5

( 2 ) INFORMATION FOR SEQ ID NO:51:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "Position 1 = nicotinoyl-Pro."

( i x ) FEATURE:
        ( A ) NAME/KEY: Modified-site
        ( B ) LOCATION: 6
        ( D ) OTHER INFORMATION: /note= "Position 6 = Gly-Cholesteryl ester."

( x i ) SEQUENCE DESCRIPTION: SEQ ID NO:51:

Pro Pro Gln Leu Pro Gly
1                   5

( 2 ) INFORMATION FOR SEQ ID NO:52:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "Position 1 = Nicotinoyl-Pro."

( i x ) FEATURE:
        ( A ) NAME/KEY: Modified-site
        ( B ) LOCATION: 6

( D ) OTHER INFORMATION: /note= "Position 6 = Gly-Cholesteryl
                        ester."

( x i ) SEQUENCE DESCRIPTION: SEQ ID NO:52:

Pro   Pro   Gln   Leu   Pro   Gly
    1                       5

( 2 ) INFORMATION FOR SEQ ID NO:53:

( i ) SEQUENCE CHARACTERISTICS:
            ( A ) LENGTH: 5 amino acids
            ( B ) TYPE: amino acid
            ( C ) STRANDEDNESS: single
            ( D ) TOPOLOGY: linear ( i i ) MOLECULE TYPE: peptide ( i x ) FEATURE:
            ( A ) NAME/KEY: Modified-site
            ( B ) LOCATION: 1
            ( D ) OTHER INFORMATION: /note= "Position 1 =
                    1,4- Dihydrotrigonellyl-Pro methylsulfate."

( i x ) FEATURE:
            ( A ) NAME/KEY: Modified-site
            ( B ) LOCATION: 5
            ( D ) OTHER INFORMATION: /note= "Position 5 = Gly-Cholesteryl
                    ester."

( x i ) SEQUENCE DESCRIPTION: SEQ ID NO:53:

Pro   Gln   Leu   Pro   Gly
    1                 5

( 2 ) INFORMATION FOR SEQ ID NO:54:

( i ) SEQUENCE CHARACTERISTICS:
            ( A ) LENGTH: 5 amino acids
            ( B ) TYPE: amino acid
            ( C ) STRANDEDNESS: single
            ( D ) TOPOLOGY: linear ( i i ) MOLECULE TYPE: peptide ( i x ) FEATURE:
            ( A ) NAME/KEY: Modified-site
            ( B ) LOCATION: 1
            ( D ) OTHER INFORMATION: /note= "Position 1 =
                    1,4- Dihydrotrigonellyl-Pro."

( i x ) FEATURE:
            ( A ) NAME/KEY: Modified-site
            ( B ) LOCATION: 5
            ( D ) OTHER INFORMATION: /note= "Position 5 = Gly-Cholesteryl
                    ester."

( x i ) SEQUENCE DESCRIPTION: SEQ ID NO:54:

Pro   Gln   Leu   Pro   Gly
    1                 5

( 2 ) INFORMATION FOR SEQ ID NO:55:

( i ) SEQUENCE CHARACTERISTICS:
            ( A ) LENGTH: 6 amino acids
            ( B ) TYPE: amino acid
            ( C ) STRANDEDNESS: single
            ( D ) TOPOLOGY: linear ( i i ) MOLECULE TYPE: peptide ( i x ) FEATURE:
            ( A ) NAME/KEY: Modified-site
            ( B ) LOCATION: 1
            ( D ) OTHER INFORMATION: /note= "Position 1 =
                    1,4- Dihydrotrigonellyl-Ala methylsulfate."

( i x ) FEATURE:
    ( A ) NAME/KEY: Modified-site
    ( B ) LOCATION: 6
    ( D ) OTHER INFORMATION: /note= "Position 6 = Gly-Cholesteryl ester."

( x i ) SEQUENCE DESCRIPTION: SEQ ID NO:55:

Ala Pro Gln Leu Pro Gly
1               5

( 2 ) INFORMATION FOR SEQ ID NO:56:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note= "Position 1 = 1,4- Dihydrotrigonellyl-Ala."

( i x ) FEATURE:
    ( A ) NAME/KEY: Modified-site
    ( B ) LOCATION: 6
    ( D ) OTHER INFORMATION: /note= "Position 6 = Gly-Cholesteryl ester."

( x i ) SEQUENCE DESCRIPTION: SEQ ID NO:56:

Ala Pro Gln Leu Pro Gly
1               5

( 2 ) INFORMATION FOR SEQ ID NO:57:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note= "Position 1 = 1,4- Dihydrotrigonellyl-Pro methylsulfate."

( i x ) FEATURE:
    ( A ) NAME/KEY: Modified-site
    ( B ) LOCATION: 5
    ( D ) OTHER INFORMATION: /note= "Position 5 = Gly-Cholesteryl ester."

( x i ) SEQUENCE DESCRIPTION: SEQ ID NO:57:

Pro Pro Gln Leu Pro Gly
1               5

( 2 ) INFORMATION FOR SEQ ID NO:58:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i i ) MOLECULE TYPE: peptide ( i x ) FEATURE:

(A) NAME/KEY: Modified-site
(B) LOCATION: 1
(D) OTHER INFORMATION: /note= "Position 1 = 1,4- Dihydrotrigonellyl-Pro."

(ix) FEATURE:
(A) NAME/KEY: Modified-site
(B) LOCATION: 6
(D) OTHER INFORMATION: /note= "Position 6 = Gly-Cholesteryl ester."

(xi) SEQUENCE DESCRIPTION: SEQ ID NO:58:

Pro Pro Gln Leu Pro Gly
1               5

(2) INFORMATION FOR SEQ ID NO:59:

(i) SEQUENCE CHARACTERISTICS:
(A) LENGTH: 4 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1
(D) OTHER INFORMATION: /note= "Position 1 = nicotinoyl-Ala."

(ix) FEATURE:
(A) NAME/KEY: Modified-site
(B) LOCATION: 3
(D) OTHER INFORMATION: /note= "Position 3 = Tyr (O-tBu)."

(ix) FEATURE:
(A) NAME/KEY: Modified-site
(B) LOCATION: 4
(D) OTHER INFORMATION: /note= "Position 4 = Arg (jPmc)-Cholesteryl ester."

(xi) SEQUENCE DESCRIPTION: SEQ ID NO:59:

Ala Ala Tyr Arg
1

(2) INFORMATION FOR SEQ ID NO:60:

(i) SEQUENCE CHARACTERISTICS:
(A) LENGTH: 4 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1
(D) OTHER INFORMATION: /note= "Position 1 = Trigonellyl-Ala."

(ix) FEATURE:
(A) NAME/KEY: Modified-site
(B) LOCATION: 3
(D) OTHER INFORMATION: /note= "Position 3 = Tyr (O-tBu)."

(ix) FEATURE:
(A) NAME/KEY: Modified-site
(B) LOCATION: 4
(D) OTHER INFORMATION: /note= "Position 4 = Arg (jPmc)-Cholesteryl ester."

(xi) SEQUENCE DESCRIPTION: SEQ ID NO:60:

Ala Ala Tyr Arg
1

( 2 ) INFORMATION FOR SEQ ID NO:61:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "Position 1 = Trigonellyl-Ala"

( i x ) FEATURE:
        ( A ) NAME/KEY: Modified-site
        ( B ) LOCATION: 4
        ( D ) OTHER INFORMATION: /note= "Position 4 = Arg-Cholesteryl ester."

( x i ) SEQUENCE DESCRIPTION: SEQ ID NO:61:

Ala Ala Tyr Arg
    1

( 2 ) INFORMATION FOR SEQ ID NO:62:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "Position 1 = 1,4- Dihydrotrigonellyl-Ala."

( i x ) FEATURE:
        ( A ) NAME/KEY: Modified-site
        ( B ) LOCATION: 4
        ( D ) OTHER INFORMATION: /note= "Position 4 = Arg-Cholesteryl ester."

( x i ) SEQUENCE DESCRIPTION: SEQ ID NO:62:

Ala Ala Tyr Arg
    1

( 2 ) INFORMATION FOR SEQ ID NO:63:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "Position 1 = nicotinoyl-Pro."

( i x ) FEATURE:
        ( A ) NAME/KEY: Modified-site
        ( B ) LOCATION: 3
        ( D ) OTHER INFORMATION: /note= "Position 3 = Tyr (O-tBu)."

( i x ) FEATURE:
        ( A ) NAME/KEY: Modified-site
        ( B ) LOCATION: 4

( D ) OTHER INFORMATION: /note= "Position 4 = Arg (jPmc)
Cholesteryl ester."

( x i ) SEQUENCE DESCRIPTION: SEQ ID NO:63:

Pro Pro Tyr Arg
1

( 2 ) INFORMATION FOR SEQ ID NO:64:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Modified-site
( B ) LOCATION: 1
( D ) OTHER INFORMATION: /note= "Position 1 = Trigonellyl-Pro
methylsulfate."

( i x ) FEATURE:
( A ) NAME/KEY: Modified-site
( B ) LOCATION: 3
( D ) OTHER INFORMATION: /note= "Position 3 = Tyr (O-tBu)."

( i x ) FEATURE:
( A ) NAME/KEY: Modified-site
( B ) LOCATION: 4
( D ) OTHER INFORMATION: /note= "Position 4 = Arg
( j - P m c )-Cholesteryl ester."

( x i ) SEQUENCE DESCRIPTION: SEQ ID NO:64:

Pro Pro Tyr Arg
1

( 2 ) INFORMATION FOR SEQ ID NO:65:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Modified-site
( B ) LOCATION: 1
( D ) OTHER INFORMATION: /note= "Position 1 - Trigonellyl-Pro."

( i x ) FEATURE:
( A ) NAME/KEY: Modified-site
( B ) LOCATION: 4
( D ) OTHER INFORMATION: /note= "Position 4 = Arg-Cholesteryl
ester."

( x i ) SEQUENCE DESCRIPTION: SEQ ID NO:65:

Pro Pro Tyr Arg
1

( 2 ) INFORMATION FOR SEQ ID NO:66:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note= "Position 1 =
        1,4- Dihydrotrigonellyl-Pro."

( i x ) FEATURE:
    ( A ) NAME/KEY: Modified-site
    ( B ) LOCATION: 4
    ( D ) OTHER INFORMATION: /note= "Position 4 = Arg-Cholesteryl
        ester."

( x i ) SEQUENCE DESCRIPTION: SEQ ID NO:66:

Pro Pro Tyr Arg
1

( 2 ) INFORMATION FOR SEQ ID NO:67:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "Position 1 = nicotinoyl-Ala."

( i x ) FEATURE:
        ( A ) NAME/KEY: Modified-site
        ( B ) LOCATION: 3
        ( D ) OTHER INFORMATION: /note= "Position 3 = Tyr (O-tBu)."

( i x ) FEATURE:
        ( A ) NAME/KEY: Modified-site
        ( B ) LOCATION: 4
        ( D ) OTHER INFORMATION: /note= "Position 4 = Arg (j-Pmc)
            Cholesteryl ester."

( x i ) SEQUENCE DESCRIPTION: SEQ ID NO:67:

Pro Pro Tyr Arg
1

( 2 ) INFORMATION FOR SEQ ID NO:68:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "Position 1 = Trigonellyl-Ala
            methylsulfate."

( i x ) FEATURE:
        ( A ) NAME/KEY: Modified-site
        ( B ) LOCATION: 3
        ( D ) OTHER INFORMATION: /note= "Position 3 = Tyr (O-tBu)."

( i x ) FEATURE:
        ( A ) NAME/KEY: Modified-site
        ( B ) LOCATION: 4
        ( D ) OTHER INFORMATION: /note= "Position 4 = Arg
            ( j - P m c )-Cholesteryl ester."

( x i ) SEQUENCE DESCRIPTION: SEQ ID NO:68:

Ala Pro Tyr Arg ( 2 ) INFORMATION FOR SEQ ID NO:69:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "Position 1 = Trigonellyl-Ala methylsulfate."

( i x ) FEATURE:
        ( A ) NAME/KEY: Modified-site
        ( B ) LOCATION: 4
        ( D ) OTHER INFORMATION: /note= "Position 4 = Arg-Cholesteryl ester."

( x i ) SEQUENCE DESCRIPTION: SEQ ID NO:69:

Ala  Pro  Tyr  Arg
    1

( 2 ) INFORMATION FOR SEQ ID NO:70:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "Position 1 = 1,4- dihydrotrionellyl-Ala."

( i x ) FEATURE:
        ( A ) NAME/KEY: Modified-site
        ( B ) LOCATION: 4
        ( D ) OTHER INFORMATION: /note= "Position 4 = Arg-Cholesteryl ester."

( x i ) SEQUENCE DESCRIPTION: SEQ ID NO:70:

Ala  Pro  Tyr  Arg
    1

( 2 ) INFORMATION FOR SEQ ID NO:71:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "Position 1 = nicotinoyl-Pro."

( i x ) FEATURE:
        ( A ) NAME/KEY: Modified-site
        ( B ) LOCATION: 3
        ( D ) OTHER INFORMATION: /note= "Position 3 = Tyr (O-tBu)."

( i x ) FEATURE:

( A ) NAME/KEY: Modified-site
( B ) LOCATION: 4
( D ) OTHER INFORMATION: /note= "Position 4 = Arg
( j - P m c )-Cholesteryl ester."

( x i ) SEQUENCE DESCRIPTION: SEQ ID NO:71:

Pro Ala Tyr Arg
1

( 2 ) INFORMATION FOR SEQ ID NO:72:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Modified-site
( B ) LOCATION: 1
( D ) OTHER INFORMATION: /note= "Position 1 = trigonellyl-Pro
methylsulfate."

( i x ) FEATURE:
( A ) NAME/KEY: Modified-site
( B ) LOCATION: 2
( D ) OTHER INFORMATION: /note= "Position 2 = Tyr (O-tBu)."

( i x ) FEATURE:
( A ) NAME/KEY: Modified-site
( B ) LOCATION: 4
( D ) OTHER INFORMATION: /note= "Position 4 = Arg
( j - P m c )-Cholesteryl ester."

( x i ) SEQUENCE DESCRIPTION: SEQ ID NO:72:

Pro Ala Tyr Arg
1

( 2 ) INFORMATION FOR SEQ ID NO:73:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Modified-site
( B ) LOCATION: 1
( D ) OTHER INFORMATION: /note= "Position 1 = trigonellyl-Pro
methylsulfate."

( i x ) FEATURE:
( A ) NAME/KEY: Modified-site
( B ) LOCATION: 4
( D ) OTHER INFORMATION: /note= "Position 4 = Arg-Cholesteryl
ester."

( x i ) SEQUENCE DESCRIPTION: SEQ ID NO:73:

Pro Ala Tyr Arg
1

( 2 ) INFORMATION FOR SEQ ID NO:74:

( i ) SEQUENCE CHARACTERISTICS:
( A ) LENGTH: 4 amino acids
( B ) TYPE: amino acid
( C ) STRANDEDNESS: single
( D ) TOPOLOGY: linear (i i) MOLECULE TYPE: peptide (i x) FEATURE:
    (A) NAME/KEY: Modified-site
    (B) LOCATION: 1
    (D) OTHER INFORMATION: /note= "Position 1 = 1,4- dihydrotrigonellyl-Pro."

(i x) FEATURE:
    (A) NAME/KEY: Modified-site
    (B) LOCATION: 4
    (D) OTHER INFORMATION: /note= "Position 4 = Arg-Cholesteryl ester."

(x i) SEQUENCE DESCRIPTION: SEQ ID NO:74:

Pro Ala Tyr Arg
1

(2) INFORMATION FOR SEQ ID NO:75:

(i) SEQUENCE CHARACTERISTICS:
        (A) LENGTH: 5 amino acids
        (B) TYPE: amino acid
        (C) STRANDEDNESS: single
        (D) TOPOLOGY: linear (i i) MOLECULE TYPE: peptide (i x) FEATURE:
    (A) NAME/KEY: Modified-site
    (B) LOCATION: 1
    (D) OTHER INFORMATION: /note= "Position 1 = H-Tyr."

(i x) FEATURE:
    (A) NAME/KEY: Modified-site
    (B) LOCATION: 2
    (D) OTHER INFORMATION: /note= "Position 2 = D-Ala."

(i x) FEATURE:
    (A) NAME/KEY: Modified-site
    (B) LOCATION: 5
    (D) OTHER INFORMATION: /note= "Position 5 = D-Leu-OH."

(x i) SEQUENCE DESCRIPTION: SEQ ID NO:75:

Tyr Ala Gly Phe Leu
1                  5

(2) INFORMATION FOR SEQ ID NO:76:

(i) SEQUENCE CHARACTERISTICS:
        (A) LENGTH: 4 amino acids
        (B) TYPE: amino acid
        (C) STRANDEDNESS: single
        (D) TOPOLOGY: linear (i i) MOLECULE TYPE: peptide (i x) FEATURE:
    (A) NAME/KEY: Modified-site
    (B) LOCATION: 1
    (D) OTHER INFORMATION: /note= "Position 1 = N-t-Boc-D-Ala."

(i x) FEATURE:
    (A) NAME/KEY: Modified-site
    (B) LOCATION: 4
    (D) OTHER INFORMATION: /note= "Position 4 = D-Leu-Cholesteryl ester."

(x i) SEQUENCE DESCRIPTION: SEQ ID NO:76:

Ala Gly Phe Leu
1

(2) INFORMATION FOR SEQ ID NO:77:

( i ) SEQUENCE CHARACTERISTICS:
   ( A ) LENGTH: 5 amino acids
   ( B ) TYPE: amino acid
   ( C ) STRANDEDNESS: single
   ( D ) TOPOLOGY: linear ( i i ) MOLECULE TYPE: peptide ( i x ) FEATURE:
   ( A ) NAME/KEY: Modified-site
   ( B ) LOCATION: 1
   ( D ) OTHER INFORMATION: /note= "Position 1 = N-t-Boc-Tyr."

( i x ) FEATURE:
   ( A ) NAME/KEY: Modified-site
   ( B ) LOCATION: 2
   ( D ) OTHER INFORMATION: /note= "Position 2 = D-Ala."

( i x ) FEATURE:
   ( A ) NAME/KEY: Modified-site
   ( B ) LOCATION: 5
   ( D ) OTHER INFORMATION: /note= "Position 5 = D-Leu-Cholesteryl ester."

( x i ) SEQUENCE DESCRIPTION: SEQ ID NO:77:

Tyr  Ala  Gly  Phe  Leu
1                     5

( 2 ) INFORMATION FOR SEQ ID NO:78:

( i ) SEQUENCE CHARACTERISTICS:
      ( A ) LENGTH: 6 amino acids
      ( B ) TYPE: amino acid
      ( C ) STRANDEDNESS: single
      ( D ) TOPOLOGY: linear ( i i ) MOLECULE TYPE: peptide ( i x ) FEATURE:
      ( A ) NAME/KEY: Modified-site
      ( B ) LOCATION: 1
      ( D ) OTHER INFORMATION: /note= "Position 1 = N-t-Boc-Ala."

( i x ) FEATURE:
      ( A ) NAME/KEY: Modified-site
      ( B ) LOCATION: 3
      ( D ) OTHER INFORMATION: /note= "Position 3 = D-Ala."

( i x ) FEATURE:
      ( A ) NAME/KEY: Modified-site
      ( B ) LOCATION: 6
      ( D ) OTHER INFORMATION: /note= "Position 6 = D-Leu-Cholesteryl ester."

( x i ) SEQUENCE DESCRIPTION: SEQ ID NO:78:

Ala  Tyr  Ala  Glu  Phe  Leu
1                     5

( 2 ) INFORMATION FOR SEQ ID NO:79:

( i ) SEQUENCE CHARACTERISTICS:
      ( A ) LENGTH: 6 amino acids
      ( B ) TYPE: amino acid
      ( C ) STRANDEDNESS: single
      ( D ) TOPOLOGY: linear ( i i ) MOLECULE TYPE: peptide ( i x ) FEATURE:
      ( A ) NAME/KEY: Modified-site
      ( B ) LOCATION: 1
      ( D ) OTHER INFORMATION: /note= "Position 1 = Nicotinoyl-Ala."

( i x ) FEATURE:
      ( A ) NAME/KEY: Modified-site (B) LOCATION: 3
(D) OTHER INFORMATION: /note= "Position 3 = D-Ala."

(ix) FEATURE:
(A) NAME/KEY: Modified-site
(B) LOCATION: 6
(D) OTHER INFORMATION: /note= "Position 6 = D-Leu-Cholesteryl ester."

(xi) SEQUENCE DESCRIPTION: SEQ ID NO:79:

Ala Tyr Ala Gly Phe Leu
1               5

(2) INFORMATION FOR SEQ ID NO:80:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1
(D) OTHER INFORMATION: /note= "Position 1 = trigonellyl-Ala methylsulfate."

(ix) FEATURE:
(A) NAME/KEY: Modified-site
(B) LOCATION: 3
(D) OTHER INFORMATION: /note= "Position 3 = D-Ala."

(ix) FEATURE:
(A) NAME/KEY: Modified-site
(B) LOCATION: 6
(D) OTHER INFORMATION: /note= "Position 6 = D-Leu-Cholesteryl ester."

(xi) SEQUENCE DESCRIPTION: SEQ ID NO:80:

Ala Tyr Ala Gly Phe Leu
1               5

(2) INFORMATION FOR SEQ ID NO:81:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1
(D) OTHER INFORMATION: /note= "Position 1 = 1,4- Dihydrotrigonellyl-Ala."

(ix) FEATURE:
(A) NAME/KEY: Modified-site
(B) LOCATION: 3
(D) OTHER INFORMATION: /note= "Position 3 = D-Ala."

(ix) FEATURE:
(A) NAME/KEY: Modified-site
(B) LOCATION: 6
(D) OTHER INFORMATION: /note= "Position 6 = D-Leu- Cholesteryl ester."

(xi) SEQUENCE DESCRIPTION: SEQ ID NO:81:

Ala Tyr Ala Gly Phe Leu
1               5

( 2 ) INFORMATION FOR SEQ ID NO:82:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "Position 1 = H-Tyr."

( i x ) FEATURE:
        ( A ) NAME/KEY: Modified-site
        ( B ) LOCATION: 2
        ( D ) OTHER INFORMATION: /note= "Position 2 = D-Ala."

( i x ) FEATURE:
        ( A ) NAME/KEY: Modified-site
        ( B ) LOCATION: 5
        ( D ) OTHER INFORMATION: /note= "Position 5 = D-Leu-Cholesteryl ester."

( x i ) SEQUENCE DESCRIPTION: SEQ ID NO:82:

Tyr  Ala  Gly  Phe  Leu
    1                        5

( 2 ) INFORMATION FOR SEQ ID NO:83:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "Position 1 = N-t-Boc-Ala."

( i x ) FEATURE:
        ( A ) NAME/KEY: Modified-site
        ( B ) LOCATION: 4
        ( D ) OTHER INFORMATION: /note= "Position 4 = D-Ala."

( i x ) FEATURE:
        ( A ) NAME/KEY: Modified-site
        ( B ) LOCATION: 7
        ( D ) OTHER INFORMATION: /note= "Position 7 = D-Leu-Cholesteryl ester."

( x i ) SEQUENCE DESCRIPTION: SEQ ID NO:83:

Ala  Ala  Tyr  Ala  Gly  Phe  Leu
    1                        5

( 2 ) INFORMATION FOR SEQ ID NO:84:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "Position 1 = Nicotinoyl-Ala."

( i x ) FEATURE:
  ( A ) NAME/KEY: Modified-site
  ( B ) LOCATION: 4
  ( D ) OTHER INFORMATION: /note= "Position 4 = D-Ala."

( i x ) FEATURE:
  ( A ) NAME/KEY: Modified-site
  ( B ) LOCATION: 7
  ( D ) OTHER INFORMATION: /note= "Position 7 = D-Leu-Cholesteryl ester."

( x i ) SEQUENCE DESCRIPTION: SEQ ID NO:84:

Ala Ala Tyr Ala Gly Phe Leu
1      5

( 2 ) INFORMATION FOR SEQ ID NO:85:

( i ) SEQUENCE CHARACTERISTICS:
  ( A ) LENGTH: 7 amino acids
  ( B ) TYPE: amino acid
  ( C ) STRANDEDNESS: single
  ( D ) TOPOLOGY: linear ( i i ) MOLECULE TYPE: peptide ( i x ) FEATURE:
  ( A ) NAME/KEY: Modified-site
  ( B ) LOCATION: 1
  ( D ) OTHER INFORMATION: /note= "Position 1 = trigonellyl-Ala-methylsulfate."

( i x ) FEATURE:
  ( A ) NAME/KEY: Modified-site
  ( B ) LOCATION: 4
  ( D ) OTHER INFORMATION: /note= "Position 4 = D-Ala."

( i x ) FEATURE:
  ( A ) NAME/KEY: Modified-site
  ( B ) LOCATION: 7
  ( D ) OTHER INFORMATION: /note= "Position 7 = D-Leu-Cholesteryl ester."

( x i ) SEQUENCE DESCRIPTION: SEQ ID NO:85:

Ala Ala Tyr Ala Gly Phe Leu
1      5

( 2 ) INFORMATION FOR SEQ ID NO:86:

( i ) SEQUENCE CHARACTERISTICS:
  ( A ) LENGTH: 7 amino acids
  ( B ) TYPE: amino acid
  ( C ) STRANDEDNESS: single
  ( D ) TOPOLOGY: linear ( i i ) MOLECULE TYPE: peptide ( i x ) FEATURE:
  ( A ) NAME/KEY: Modified-site
  ( B ) LOCATION: 1
  ( D ) OTHER INFORMATION: /note= "Position 1 = 1,4- Dihydrotrigonellyl-Ala."

( i x ) FEATURE:
  ( A ) NAME/KEY: Modified-site
  ( B ) LOCATION: 4
  ( D ) OTHER INFORMATION: /note= "Position 4 = D-Ala."

( i x ) FEATURE:
  ( A ) NAME/KEY: Modified-site
  ( B ) LOCATION: 7
  ( D ) OTHER INFORMATION: /note= "Position 7 = D-Leu-Cholesteryl ester."

( x i ) SEQUENCE DESCRIPTION: SEQ ID NO:86:

Ala Ala Tyr Ala Gly Phe Leu 1           5

(2) INFORMATION FOR SEQ ID NO:87:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Position 1 = Trigonellyl-Ala
            methylsulfate."

(ix) FEATURE:
        (A) NAME/KEY: Modified-site
        (B) LOCATION: 3
        (D) OTHER INFORMATION: /note= "Position 3 = D-Ala."

(ix) FEATURE:
        (A) NAME/KEY: Modified-site
        (B) LOCATION: 6
        (D) OTHER INFORMATION: /note= "Position 6 = D-Leu-OH."

(xi) SEQUENCE DESCRIPTION: SEQ ID NO:87:

Ala Tyr Ala Gly Phe Leu
1               5

(2) INFORMATION FOR SEQ ID NO:88:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Position 1 = Trigonellyl-Ala
            methylsulfate."

(ix) FEATURE:
        (A) NAME/KEY: Modified-site
        (B) LOCATION: 4
        (D) OTHER INFORMATION: /note= "Position 4 - D-Ala."

(ix) FEATURE:
        (A) NAME/KEY: Modified-site
        (B) LOCATION: 7
        (D) OTHER INFORMATION: /note= "Position 7 =
            D-Leu-OH- Cholesteryl ester."

(xi) SEQUENCE DESCRIPTION: SEQ ID NO:88:

Ala Ala Tyr Ala Gly Phe Leu
1               5

(2) INFORMATION FOR SEQ ID NO:89:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site (B) LOCATION: 1
(D) OTHER INFORMATION: /note= "Position 1 = Trigonellyl-Ala methylsulfate."

(ix) FEATURE:
(A) NAME/KEY: Modified-site
(B) LOCATION: 3
(D) OTHER INFORMATION: /note= "Position 3 = D-Ala."

(ix) FEATURE:
(A) NAME/KEY: Modified-site
(B) LOCATION: 6
(D) OTHER INFORMATION: /note= "Position 6 = D-Leu-ethyl ester."

(xi) SEQUENCE DESCRIPTION: SEQ ID NO:89:

Ala  Tyr  Ala  Gly  Phe  Leu
1                   5

(2) INFORMATION FOR SEQ ID NO:90:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1
(D) OTHER INFORMATION: /note= "Position 1 = 1,4- dihydrotrigonellyl-Ala."

(ix) FEATURE:
(A) NAME/KEY: Modified-site
(B) LOCATION: 3
(D) OTHER INFORMATION: /note= "Position 3 = D-Ala."

(ix) FEATURE:
(A) NAME/KEY: Modified-site
(B) LOCATION: 6
(D) OTHER INFORMATION: /note= "Position 6 = D-Leu-ethyl ester."

(xi) SEQUENCE DESCRIPTION: SEQ ID NO:90:

Ala  Tyr  Ala  Gly  Phe  Leu
1                   5

(2) INFORMATION FOR SEQ ID NO:91:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1
(D) OTHER INFORMATION: /note= "Position 1 = 1,4- dihydrotrigonellyl-Ala."

(ix) FEATURE:
(A) NAME/KEY: Modified-site
(B) LOCATION: 3
(D) OTHER INFORMATION: /note= "Position 3 = D-Ala."

(ix) FEATURE:
(A) NAME/KEY: Modified-site
(B) LOCATION: 6
(D) OTHER INFORMATION: /note= "Position 6 = D-Leu-OH."

( x i ) SEQUENCE DESCRIPTION: SEQ ID NO:91:

Ala Tyr Ala Gly Phe Leu
1               5

( 2 ) INFORMATION FOR SEQ ID NO:92:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "Position 1 = N-t-Boc-Pro."

( i x ) FEATURE:
        ( A ) NAME/KEY: Modified-site
        ( B ) LOCATION: 3
        ( D ) OTHER INFORMATION: /note= "Position 3 = D-Ala."

( i x ) FEATURE:
        ( A ) NAME/KEY: Modified-site
        ( B ) LOCATION: 6
        ( D ) OTHER INFORMATION: /note= "Position 6 = D-Leu-Cholesteryl ester."

( x i ) SEQUENCE DESCRIPTION: SEQ ID NO:92:

Pro Tyr Ala Gly Phe Leu
1               5

( 2 ) INFORMATION FOR SEQ ID NO:93:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "Position 1 = Nicotinoyl-Pro."

( i x ) FEATURE:
        ( A ) NAME/KEY: Modified-site
        ( B ) LOCATION: 3
        ( D ) OTHER INFORMATION: /note= "Position 3 = D-Ala."

( i x ) FEATURE:
        ( A ) NAME/KEY: Modified-site
        ( B ) LOCATION: 6
        ( D ) OTHER INFORMATION: /note= "Position 6 = D-Leu-Cholesteryl ester."

( x i ) SEQUENCE DESCRIPTION: SEQ ID NO:93:

Pro Tyr Ala Gly Phe Leu
1               5

( 2 ) INFORMATION FOR SEQ ID NO:94:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note= "Position 1 = Trigonellyl-Pro methylsulfate."

( i x ) FEATURE:
    ( A ) NAME/KEY: Modified-site
    ( B ) LOCATION: 3
    ( D ) OTHER INFORMATION: /note= "Position 3 = D-Ala."

( i x ) FEATURE:
    ( A ) NAME/KEY: Modified-site
    ( B ) LOCATION: 6
    ( D ) OTHER INFORMATION: /note= "Position 6 = D-Leu-Cholesteryl ester."

( x i ) SEQUENCE DESCRIPTION: SEQ ID NO:94:

Pro Tyr Ala Gly Phe Leu
1               5

( 2 ) INFORMATION FOR SEQ ID NO:95:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "Position 1 = 1,4- Dihydrotrigonellyl-Pro."

( i x ) FEATURE:
        ( A ) NAME/KEY: Modified-site
        ( B ) LOCATION: 3
        ( D ) OTHER INFORMATION: /note= "Position 3 = D-Ala."

( i x ) FEATURE:
        ( A ) NAME/KEY: Modified-site
        ( B ) LOCATION: 6
        ( D ) OTHER INFORMATION: /note= "Position 6 = D-Leu-Cholesteryl ester."

( x i ) SEQUENCE DESCRIPTION: SEQ ID NO:95:

Pro Tyr Ala Gly Phe Leu
1               5

( 2 ) INFORMATION FOR SEQ ID NO:96:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "Position 1 = N-t-Boc-Ala."

( i x ) FEATURE:
        ( A ) NAME/KEY: Modified-site
        ( B ) LOCATION: 4
        ( D ) OTHER INFORMATION: /note= "Position 4 = D-Ala."

( i x ) FEATURE:
        ( A ) NAME/KEY: Modified-site
        ( B ) LOCATION: 7
        ( D ) OTHER INFORMATION: /note= "Position 7 = D-Leu-Cholesteryl ester."

(x i) SEQUENCE DESCRIPTION: SEQ ID NO:96:

Ala Pro Tyr Ala Gly Phe Leu
1               5

(2) INFORMATION FOR SEQ ID NO:97:

(i) SEQUENCE CHARACTERISTICS:
        (A) LENGTH: 7 amino acids
        (B) TYPE: amino acid
        (C) STRANDEDNESS: single
        (D) TOPOLOGY: linear (i i) MOLECULE TYPE: peptide (i x) FEATURE:
        (A) NAME/KEY: Modified-site
        (B) LOCATION: 1
        (D) OTHER INFORMATION: /note= "Position 1 = Nicotinoyl-Ala."

(i x) FEATURE:
        (A) NAME/KEY: Modified-site
        (B) LOCATION: 4
        (D) OTHER INFORMATION: /note= "Position 4 = D-Ala."

(i x) FEATURE:
        (A) NAME/KEY: Modified-site
        (B) LOCATION: 7
        (D) OTHER INFORMATION: /note= "Position 7 = D-Leu-Cholesteryl
            ester."

(x i) SEQUENCE DESCRIPTION: SEQ ID NO:97:

Ala Pro Tyr Ala Gly Phe Leu
1               5

(2) INFORMATION FOR SEQ ID NO:98:

(i) SEQUENCE CHARACTERISTICS:
        (A) LENGTH: 7 amino acids
        (B) TYPE: amino acid
        (C) STRANDEDNESS: single
        (D) TOPOLOGY: linear (i i) MOLECULE TYPE: peptide (i x) FEATURE:
        (A) NAME/KEY: Modified-site
        (B) LOCATION: 1
        (D) OTHER INFORMATION: /note= "Position 1 = Trigonellyl-Ala."

(i x) FEATURE:
        (A) NAME/KEY: Modified-site
        (B) LOCATION: 4
        (D) OTHER INFORMATION: /note= "Position 4 = D-Ala."

(i x) FEATURE:
        (A) NAME/KEY: Modified-site
        (B) LOCATION: 7
        (D) OTHER INFORMATION: /note= "Position 7 = D-Leu-Cholesteryl
            ester."

(x i) SEQUENCE DESCRIPTION: SEQ ID NO:98:

Ala Pro Tyr Ala Gly Phe Leu
1               5

(2) INFORMATION FOR SEQ ID NO:99:

(i) SEQUENCE CHARACTERISTICS:
        (A) LENGTH: 7 amino acids
        (B) TYPE: amino acid
        (C) STRANDEDNESS: single
        (D) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note= "Position 1 = 1,4- Dihydrotrigonellyl-Ala."

( i x ) FEATURE:
    ( A ) NAME/KEY: Modified-site
    ( B ) LOCATION: 4
    ( D ) OTHER INFORMATION: /note= "Position 4 = D-Ala."

( i x ) FEATURE:
    ( A ) NAME/KEY: Modified-site
    ( B ) LOCATION: 7
    ( D ) OTHER INFORMATION: /note= "Position 7 = D-Leu-Cholesteryl ester."

( x i ) SEQUENCE DESCRIPTION: SEQ ID NO:99:

Ala  Pro  Tyr  Ala  Gly  Phe  Leu
1                      5

( 2 ) INFORMATION FOR SEQ ID NO:100:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "Position 1 = N-t-Boc-Pro."

( i x ) FEATURE:
        ( A ) NAME/KEY: Modified-site
        ( B ) LOCATION: 4
        ( D ) OTHER INFORMATION: /note= "Position 4 = D-Ala."

( i x ) FEATURE:
        ( A ) NAME/KEY: Modified-site
        ( B ) LOCATION: 7
        ( D ) OTHER INFORMATION: /note= "Position 7 = D-Leu-Cholesteryl ester."

( x i ) SEQUENCE DESCRIPTION: SEQ ID NO:100:

Pro  Pro  Tyr  Ala  Gly  Phe  Leu
1                      5

( 2 ) INFORMATION FOR SEQ ID NO:101:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "Position 1 = Nicotinoyl-Pro."

( i x ) FEATURE:
        ( A ) NAME/KEY: Modified-site
        ( B ) LOCATION: 4
        ( D ) OTHER INFORMATION: /note= "Position 4 = D-Ala."

( i x ) FEATURE:
        ( A ) NAME/KEY: Modified-site
        ( B ) LOCATION: 7

( D ) OTHER INFORMATION: /note= "Position 7 = D-Leu-Cholesteryl
ester."

( x i ) SEQUENCE DESCRIPTION: SEQ ID NO:101:

Pro Pro Tyr Ala Gly Phe Leu
1               5

( 2 ) INFORMATION FOR SEQ ID NO:102:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note= "Position 1 = Trigonellyl-Pro
       methylsulfate."

( i x ) FEATURE:
    ( A ) NAME/KEY: Modified-site
    ( B ) LOCATION: 4
    ( D ) OTHER INFORMATION: /note= "Position 4 = D-Ala."

( i x ) FEATURE:
    ( A ) NAME/KEY: Modified-site
    ( B ) LOCATION: 7
    ( D ) OTHER INFORMATION: /note= "Position 7 = D-Leu-Cholesteryl
       ester."

( x i ) SEQUENCE DESCRIPTION: SEQ ID NO:102:

Pro Pro Tyr Ala Gly Phe Leu
1               5

( 2 ) INFORMATION FOR SEQ ID NO:103:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note= "Position 1 -
       1,4- dihydrotrigonellyl-Pro."

( i x ) FEATURE:
    ( A ) NAME/KEY: Modified-site
    ( B ) LOCATION: 4
    ( D ) OTHER INFORMATION: /note= "Position 4 = D-Ala."

( i x ) FEATURE:
    ( A ) NAME/KEY: Modified-site
    ( B ) LOCATION: 7
    ( D ) OTHER INFORMATION: /note= "Position 7 = D-Leu-Cholesteryl
       ester."

( x i ) SEQUENCE DESCRIPTION: SEQ ID NO:103:

Pro Pro Tyr Ala Gly Phe Leu
1               5

( 2 ) INFORMATION FOR SEQ ID NO:104:

( i ) SEQUENCE CHARACTERISTICS:
    ( A ) LENGTH: 7 amino acids
    ( B ) TYPE: amino acid (C) STRANDEDNESS: single
(D) TOPOLOGY: linear (ii) MOLECULE TYPE: peptide (ix) FEATURE:
    (A) NAME/KEY: Modified-site
    (B) LOCATION: 1
    (D) OTHER INFORMATION: /note= "Position 1 = N-t-Boc-Pro."

(ix) FEATURE:
    (A) NAME/KEY: Modified-site
    (B) LOCATION: 4
    (D) OTHER INFORMATION: /note= "Position 4 = D-Ala."

(ix) FEATURE:
    (A) NAME/KEY: Modified-site
    (B) LOCATION: 7
    (D) OTHER INFORMATION: /note= "Position 7 = D-Leu-Cholesteryl ester."

(xi) SEQUENCE DESCRIPTION: SEQ ID NO:104:

Pro Ala Tyr Ala Gly Phe Leu
1                5

(2) INFORMATION FOR SEQ ID NO:105:

(i) SEQUENCE CHARACTERISTICS:
    (A) LENGTH: 7 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: Modified-site
    (B) LOCATION: 1
    (D) OTHER INFORMATION: /note= "Position 1 = Nicotinoyl-Pro."

(ix) FEATURE:
    (A) NAME/KEY: Modified-site
    (B) LOCATION: 4
    (D) OTHER INFORMATION: /note= "Position 4 = D-Ala."

(ix) FEATURE:
    (A) NAME/KEY: Modified-site
    (B) LOCATION: 7
    (D) OTHER INFORMATION: /note= "Position 7 = D-Leu-Cholesteryl ester."

(xi) SEQUENCE DESCRIPTION: SEQ ID NO:105:

Pro Ala Tyr Ala Gly Phe Leu
1                5

(2) INFORMATION FOR SEQ ID NO:106:

(i) SEQUENCE CHARACTERISTICS:
    (A) LENGTH: 7 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: Modified-site
    (B) LOCATION: 1
    (D) OTHER INFORMATION: /note= "Position 1 = Trigonellyl-Pro."

(ix) FEATURE:
    (A) NAME/KEY: Modified-site
    (B) LOCATION: 4
    (D) OTHER INFORMATION: /note= "Position 4 = D-Ala."

(ix) FEATURE:

(A) NAME/KEY: Modified-site
(B) LOCATION: 7
(D) OTHER INFORMATION: /note= "Position 7 = D-Leu-Cholesteryl ester."

(xi) SEQUENCE DESCRIPTION: SEQ ID NO:106:

Pro Ala Tyr Ala Gly Phe Leu
1               5

(2) INFORMATION FOR SEQ ID NO:107:

(i) SEQUENCE CHARACTERISTICS:
(A) LENGTH: 7 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1
(D) OTHER INFORMATION: /note= "Position 1 = 1,4- Dihydrotrigonellyl-Pro."

(ix) FEATURE:
(A) NAME/KEY: Modified-site
(B) LOCATION: 4
(D) OTHER INFORMATION: /note= "Position 4 = D-Ala."

(ix) FEATURE:
(A) NAME/KEY: Modified-site
(B) LOCATION: 7
(D) OTHER INFORMATION: /note= "Position 7 = D-Leu-Cholesteryl ester."

(xi) SEQUENCE DESCRIPTION: SEQ ID NO:107:

Pro Ala Tyr Ala Gly Phe Leu
1               5

BRAIN-ENHANCED DELIVERY OF NEUROACTIVE PEPTIDES BY SEQUENTIAL METABOLISM

CROSS-REFERENCE TO RELATED APPLICATION

This is a continuation of prior U.S. application Ser. No. 07/946,062, filed Sep. 17, 1992, now abandoned.

FIELD OF THE INVENTION

The invention provides novel peptide derivatives comprising a dihydropyridine⇌pyridinium salt-type redox targetor moiety, bulky lipophilic functions and amino acid/dipeptide/tripeptide spacers which are designed to deliver pharmacologically active peptides into the central nervous system by sequential metabolism.

BACKGROUND OF THE INVENTION

The blood-brain barrier (BBB) is the major obstacle for the development of centrally active peptides. The capillaries in the brain parenchyma possess high-resistance, tight junctions between the endothelial cells. The cells also lack pores, thus the brain capillary endothelium behaves like a continuous lipid bilayer. Diffusion through this layer, the physical BBB, is largely dependent on the lipid solubility of the solute. Water-soluble molecules (for example, glucose, essential amino acids, glutamate) enter the brain almost exclusively by carrier-mediated transport. Most peptides, such as the naturally occurring enkephalins, are hydrophilic and do not cross the BBB, due to the absence of specific transport systems in the membrane. Their metabolic instability also implies that the highly active neuropeptide degrading enzymes, such as the capillary-bound aminopeptidase, arylamidase and enkephalinase, constitute an enzymatic BBB for peptides that results in their rapid cleavage. See, for example, W. M. Pardridge, in *Peptide Drug Delivery to the Brain* (Raven Press, New York, 1991), pp. 244–250; W. M. Pardridge and L. J. Mietus, *Endocrinology* 109, 1138 (1981); L. B. Hersch, N. Aboukhair, S. Watson, *Peptides* 8, 523 (1987); J. M. Hambrook, B. A. Morgan, M. J. Ranee, C. F. C. Smith, *Nature* 262,782 (1976); and J. F. McKelvy, in *Brain Peptides*, D. T. Krieger, M. J. Brownstein, J. B. Martin, Eds. (Wiley-Interscience, New York, 1983), pp. 117–133.

Various strategies have been applied to direct centrally active peptides into the brain. An invasive procedure that includes surgical implantation of an intraventricular catheter followed by pharmaceutical infusion into the ventricular compartment delivers a metabolically unstable peptide only to the surface of the brain; D. G. Poplack, A. W. Blayer, M. E. Horowitz, in *Neurobiology of Cerebrospinal Fluid*, J. H. Wood, Ed. (Plenum Press, New York, 1981), pp. 561–578. Transient opening of the tight junctions by the intracarotid infusion of an osmotically active substance (mannitol, arabinose) in high concentrations (>1M) may facilitate an indiscriminate delivery of molecules that otherwise cannot cross the BBB; see E. A. Neuwelt and S. I. Rappaport. *Fed. Proc.* 43, 214 (1984). However, this procedure is accompanied by severe toxic effects which can lead to inflammation, encephalitis and seizures. These invasive procedures are only justified for some life-threatening conditions, and are not acceptable for less serious illnesses.

A noninvasive method for peptide delivery into the central nervous system (CNS) has been suggested that utilizes the formation of chimeric peptides [W. M. Pardridge, *Endocrinol. Rev.* 7, 314 (1986)]. This strategy relies on the presence of specific receptor-mediated transcytosis systems in the BBB for certain larger peptides such as insulin, insulin-like growth factor, transferrin and albumin. Covalently coupling (for example, via disulfide bonds) a non-transportable peptide to these transport vectors results in a chimeric peptide that can also undergo receptor-mediated transcytosis, and the active peptide can be released by its enzymatic cleavage in the CNS. However, these carriers are not brain-specific, as uptake by non-neural cells or cells outside the CNS has also been shown. See F. Ito, S. Ito, N. Shimizu, *Mol. Cell. Endocrinol.* 36, 165 (1984). Low amounts of the peptide relative to the carrier molecule, and the receptor-based cellular transport mechanism that has physiologically limited transporter capacity (saturable) also prevent pharmacologically significant amounts from entering the brain. Finally, release of the active peptide from the conjugate has not been documented.

Another method for peptide delivery is a simple pharmacologically based approach in which peptide "prodrugs" are applied that are lipophilic esters or amides of the molecule [T. Tsuzuki et al, *Biochem. Pharmacol.* 41, R5 (1991)]. Although the acquired lipophilicity of these prodrugs may assure penetration to the BBB (and to other membranes), this is not the sole factor involved in the transport of a peptide into the CNS. BBB transport of cyclosporin, which is one of the most lipid soluble peptides, is paradoxically low due to peptide degradation [D. J. Begley et al, *J. Neurochem.* 55, 1222 (1990)].

A dihydropyridine⇌pyridinium redox system has recently been successfully applied to delivery to the brain of a number of drugs. Generally speaking, according to this system, a dihydropyridine derivative of a biologically active compound is synthesized, which derivative can enter the CNS through the blood-brain barrier following its systemic administration. Subsequent oxidation of the dihydropyridine species to the corresponding pyridinium salt leads to delivery of the drug to the brain.

Four main approaches have been used thus far for delivering drugs to the brain using a redox system. The first approach involves derivation of selected drugs which contain a pyridinium nucleus as an integral structural component. This approach was first applied to delivering to the brain N-methylpyridinium-2-carbaldoxime chloride (2-PAM), the active nucleus of which constitutes a quaternary pyridinium salt, by way of the dihydropyridine latentiated prodrug form thereof. Thus, a hydrophilic compound (2-PAM) was made lipoidal (i.e. lipophilic) by making its dihydropyridine form (Pro-2-PAM) to enable its penetration through lipoidal barriers. This simple prodrug approach allowed the compound to get into the brain as well as other organs, but this manipulation did not and could not result in any brain specificity. On the contrary, such approach was delimited to relatively small molecule quaternary pyridinium ring-containing drug species and did not provide the overall ideal result of brain-specific, sustained release of the desired drug, with concomitant rapid elimination from the general circulation, enhanced drug efficacy and decreased toxicity. No "trapping" in the brain of the 2-PAM formed in situ resulted, and obviously no brain-specific, sustained delivery occurred as any consequence thereof: the 2-PAM was eliminated as fast from the brain as it was from the general circulation and other organs. Compare U.S. Pat. Nos. 3,929,813 and 3,962,447; Bodor et al, *J. Pharm. Sci.*, 67, No. 5, 685 (1978). See also Bodor, "Novel Approaches for the Design of Membrane Transport Properties of Drugs", in *Design of Biopharmaceutical Properties Through Pro-*

*drugs and Analogs*, Roche, E. B. (ed.), APhA Academy of Pharmaceutical Sciences, Washington, D.C., 98–135 (1976). Subsequent extension of this first approach to delivering a much larger quaternary salt, berberine, to the brain via its dihydropyridine prodrug form was, however, found to provide site-specific sustained delivery to the brain of that anticancer agent. See Bodor et al, *Science*, Vol. 214, Dec. 18, 1981, pp. 1370–1372. This approach is not applicable to the delivery of peptides, however, since they do not comprise active quaternary pyridinium salts.

The second approach for delivering drugs to the brain using a redox system involves the use of a dihydropyridine/ pyridinium carrier chemically linked to a biologically active compound. Bodor et al., *Science*, Vol. 214, Dec. 18, 1981, pp. 1370–1372, outlines a scheme for this specific and sustained delivery of drug species to the brain, as depicted in the following Scheme A:

drug species [D], followed by its normal elimination ($k_5$), metabolism. A properly selected carrier $[QC]^+$ will also be rapidly eliminated from the brain ($k_6 \gg k_2$). Because of the facile elimination of $[D\text{-}QC]^+$ from the general circulation, only minor amounts of drug are released in the body ($k_3 \gg k_4$); [D] will be released primarily in the brain ($k_4 > k_2$). The overall result ideally will be a brain-specific sustained release of the target drug species. Specifically, Bodor et at. worked with phenylethylamine as the drug model. That compound was coupled to nicotinic acid, then quaternized to give compounds of the formula

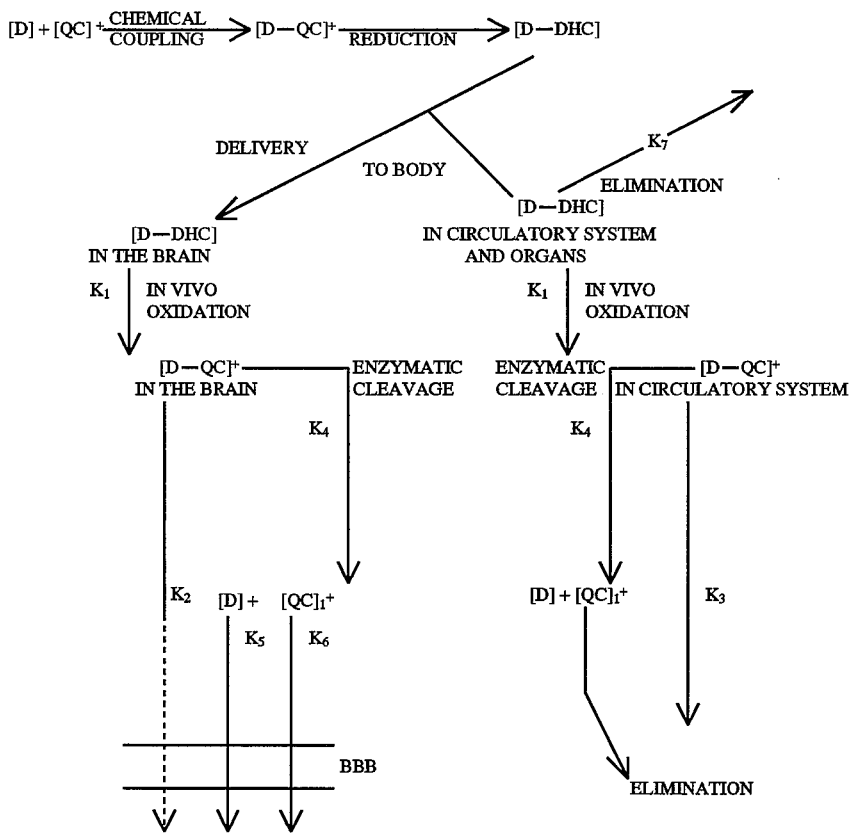

According to the scheme in Science, a drug [D] is coupled to a quaternary carrier $[QC]^+$ and the $[D\text{-}QC]^+$ which results is then reduced chemically to the lipoidal dihydro form [D-DHC]. After administration of [D-DHC] in vivo, it is rapidly distributed throughout the body, including the brain. The dihydro form [D-DHC] is then in situ oxidized (rate constant, $k_1$) (by the NAD⇌NADH system) to the ideally inactive original $[D\text{-}QC]^+$ quaternary salt which, because of its ionic, hydrophilic character, should be rapidly eliminated from the general circulation of the body, while the blood-brain barrier should prevent its elimination from the brain ($K_3 \gg k_2$; $k_3 \gg k_7$). Enzymatic cleavage of the $[D\text{-}QC]^+$ that is "locked" in the brain effects a sustained delivery of the

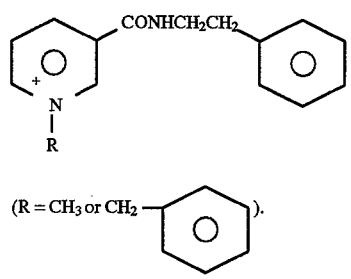

which were subsequently reduced by sodium dithionite to the corresponding compounds of the formula

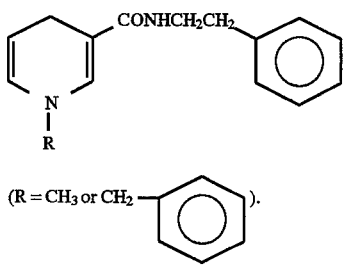

Testing of the N-methyl derivative in vivo supported the criteria set forth in Scheme A. Bodor et al. speculated that various types of drugs might possibly be delivered using the depicted or analogous carrier systems and indicated that use of N-methylnicotinic acid esters and amides and their pyridine ring-substituted derivatives was being studied for delivery of amino- or hydroxyl-containing drugs, including small peptides, to the brain. No other possible specific carriers were disclosed. Other reports of this work with the redox carrier system have appeared in *The Friday Evening Post*, Aug. 14, 1981, Health Center Communications, University of Florida, Gainesville, Fla.; *Chemical & Engineering News*, Dec. 21, 1981, pp. 24–25; and *Science News*, Jan. 2, 1982, Vol. 121, No. 1, page 7. More recently, the redox carrier system has been substantially extended in terms of possible careers and drugs to be delivered. See International Patent Application No. PCT/US83/00725, filed May 12, 1983 and published Nov. 24, 1983 under International Publication No. WO83/03968. Also see Bodor et al., *Pharmacology and Therapeutics*, Vol. 19, No. 3, pp. 337–386 (1983); and Bodor U.S. Pat. No. 4,540,564, issued Sep. 10, 1985.

The aforementioned Bodor U.S. Pat. No. 4,540,564 specifically contemplates application of the dihydropyridine⇌pyridinium salt carrier system to amino acids and peptides, particularly small peptides having 2 to 20 amino acid units. Among the amino acids and peptides mentioned in the patent are GABA, tyrosine, tryptophan, met$^5$-enkephalin, leu$^5$-enkephalin, LHRH and its analogs and others. Representative carrier-linked amino acids and peptides illustrated in the Bodor patent are the following:

| AMINO ACID/PEPTIDE | CARRIER-DRUG (QUATERNARY) | CARRIER-DRUG (DIHYDRO) |
|---|---|---|

Thus, in the depicted carrier system as applied to amino acids and peptides, the free carboxyl function is protected in an effort to prevent premature metabolism, e.g. with an ethyl ester, while the trigonelline-type carrier is linked to the amino acid or peptide through its free amino function. Oxidation of the dihydropyridine carrier moiety in vivo to the ionic pyridinium salt carrier/drug entity prevents elimination thereof from the brain, while elimination from the general circulation is accelerated, and subsequent cleavage of the quaternary carrier/drug species results in sustained delivery of the amino acid or peptide (e.g. tryptophan, GABA, leu$^5$-enkephalin, etc.) in the brain and facile elimination of the carrier moiety. This method is quite useful for delivery of amino acids; in the case of peptides, however, the typical suggested carboxyl protecting groups do not confer sufficient lipophilicity on the peptide molecule. Moreover, this approach does not address the problem of the enzymatic blood-brain barrier or suggest a means of avoiding that problem.

The third approach for delivering drugs to the brain using a redox system provides derivatives of centrally acting amines in which a primary, secondary or tertiary amine function has been replaced with a dihydropyridine/pyridinium salt redox system. These brain-specific analogs of centrally acting amines have been described in International Patent Application No. PCT/US85/00236, filed Feb. 15, 1985 and published Sep. 12, 1985 under International Publication No. WO85/03937. The dihydropyridine analogs are characterized by the structural formula

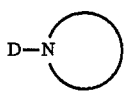

wherein D is the residue of a centrally acting primary, secondary or tertiary amine, and

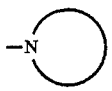

is a radical of the formula

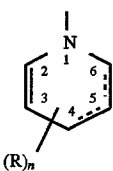

(a)

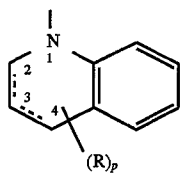

(b)

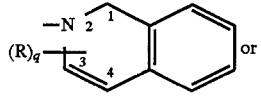

(c)

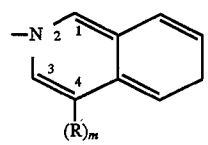

(d)

wherein the dotted line in formula (a) indicates the presence of a double bond in either the 4 or 5 position of the dihydropyridine ring; the dotted line in formula (b) indicates the presence of a double bond in either the 2 or 3 position of the dihydroquinoline ring system; m is zero or one; n is zero, one or two; p is zero, one or two, provided that when p is one or two, each R in formula (b) can be located on either of the two fused rings; q is zero, one, or two, provided that when q is one or two, each R in formula (c) can be located on either of the two fused-rings; and each R is independently selected from the group consisting of halo, $C_1$–$C_7$ alkyl, $C_1$–$C_7$ alkoxy, $C_2$–$C_8$ alkoxycarbonyl, $C_2$–$C_8$ alkanoyloxy, $C_1$–$C_7$ haloalkyl, $C_1$–$C_7$ alkylthio, $C_1$–$C_7$ alkylsulfinyl, $C_1$–$C_7$ alkylsulfonyl, —CH=NOR''' wherein R''' is H or $C_1$–$C_7$ alkyl, and —CONR'R'' wherein R' and R'', which can be the same or different, are each H or $C_1$–$C_7$ alkyl. These dihydropyridine analogs act as a delivery system for the corresponding biologically active quaternary compounds in vivo. Due to its lipophilic nature, the dihydropyridine analog will distribute throughout the body and has easy access to the brain through the blood-brain barrier. Oxidation in vivo will then provide the quaternary form, which will be "locked" preferentially in the brain. In contradistinction to the drug-carrier entities described in Bodor U.S. Pat. No. 4,540,564 and related publications, however, there is no readily metabolically cleavable bond between drug and quaternary portions, and the active species delivered is not the original drug from which the dihydro analog was derived, but rather is the quaternary analog itself.

The aforementioned International Publication No. WO85/03937 contemplates application of its analog system to amino acids and small peptides, e.g., the enkephalins, tryptophan, GABA, LHRH analogs and others. Illustrated redox analogs include the following:

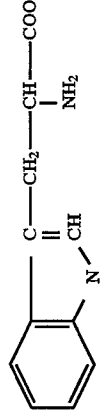

In the depicted analog system as applied to amino acids and peptides, the free carboxyl function is thus protected to prevent premature metabolism while the dihydropyridine⇌pyridinium salt type redox system replaces the free amino function in the amino acid or peptide.

As described in International Publication No. WO85/03937, the chemical processes for preparing the redox analog derivatives replace any free amino function in the selected drug with the redox analog system. When these processes are applied to amino acids, they provide a redox amino acid which no longer contains a free amino function for linkage to another amino acid or peptide via a peptide bond (—CONH—). Such an analog amino acid can thus only be used to prepare a peptide having the analog amino acid located at the peptide's N-terminus. This limits use of the redox analog amino acids in peptide synthesis. Moreover, as noted hereinabove, this approach is not designed to ultimately deliver the original peptide to the brain, since there is no cleavable bond between peptide and quaternary portions; rather, the redox portion in this approach becomes an inherent, essentially inseparable pan of a new peptide analog. Furthermore, this approach does not address the problem of the enzymatic blood-brain barrier or suggest a means for avoiding the premature degradation caused by the highly active neuropeptide degrading enzymes.

The fourth redox approach is designed to provide redox amino acids which can be used to synthesize peptides having a redox analog system inserted at a variety of locations in the peptide chain, including non-terminal positions, and has been described in Bodor U.S. Pat. No. 4,888,427, issued Dec. 19, 1989. These amino acids contain a redox system appended directly or via an alkylene bridge to the carbon atom adjacent to the carboxyl carbon. The peptides provided by U.S. Pat. No. 4,888,427 have an amino acid fragment of the formula

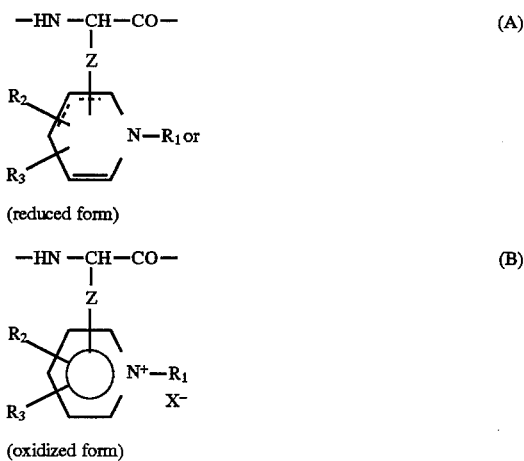

incorporated therein at a non-critical position in the peptide chain, i.e., at a position which is not critical to the pharmacological effect of the peptide. In structures (A) and (B) above, Z is either a direct bond or $C_1$-$C_6$ alkylene and can be attached to the heterocyclic ring via a ring carbon atom or via the ring nitrogen atom; $R_1$ is $C_1$-$C_7$ alkyl, $C_1$-$C_7$ haloalkyl or $C_7$-$C_{12}$ aralkyl when Z is attached to a ring carbon atom; $R_1$ is a direct bond when Z is attached to the ring nitrogen atom; $R_2$ and $R_3$, which can be the same or different, are selected from the group consisting of hydrogen, halo, cyano, $C_1$-$C_7$ alkyl, $C_1$-$C_7$ alkoxy, $C_2$-$C_8$ alkoxycarbonyl, $C_2$-$C_8$ alkanoyloxy, $C_1$-$C_7$ haloalkyl, $C_1$-$C_7$ alkylthio, $C_1$-$C_7$ alkylsulfinyl, $C_1$-$C_7$ alkylsulfonyl, —CH=NOR''' wherein R''' is hydrogen or $C_1$-$C_7$ alkyl, and —CONR'R'' wherein R' and R'', which can be the same or different, are each hydrogen or $C_1$-$C_7$ alkyl; or one of $R_2$ and $R_3$ together with the adjacent ring carbon atom forms a benzene ring fused to the heterocyclic ring, which benzene ring may optionally bear one or two substituents, which can be the same or different, selected from the group consisting of hydroxy, protected hydroxy, halo, cyano. $C_1$-$C_7$ alkyl, $C_1$-$C_7$ alkoxy, $C_2$-$C_8$ alkoxycarbonyl, $C_2$-$C_8$ alkanoyloxy, $C_1$-$C_7$ haloalkyl. $C_1$-$C_7$ alkylthio, $C_1$-$C_7$ alkylsulfinyl, $C_1$-$C_7$ alkylsulfonyl, —CH=NOR''' wherein R''' is hydrogen or $C_1$-$C_7$ alkyl, and —CONR'R'' wherein R' and R'', which can be the same or different, are each hydrogen or $C_1$-$C_7$ alkyl; the dotted lines indicate that the fragment of formula (A) or (B) contains a 1,4- or 1,6-dihydropyridine, a 1,4- or 1,2-dihydroquinoline, or a 1,2-dihydroisoquinoline ring system; and wherein X⁻ is the anion of a non-toxic pharmaceutically acceptable acid. The final redox peptide of U.S. Pat. No. 4,888,427 preferably contains a total of 2 to 20 amino acid units. Typically, except for the presence of at least one redox amino acid fragment of structure (A) or (B) and the possible protection of terminal amino and carboxyl functions, the structure of the redox peptide is identical to that of a known, naturally occurring bioactive peptide or of a known bioactive synthetic peptide (particularly one which is an analog of a naturally occurring bioactive peptide).

It is apparent from the foregoing, that the fourth redox approach, like the third approach discussed above, is not designed to ultimately deliver the original peptide to the brain because there is again no cleavable bond between peptide and quaternary portions. Again, the redox system becomes an integral part of a new peptide analog, not a means for ultimately delivering the original peptide to the brain. Still further, this approach also does not address the problem of the enzymatic blood-brain barrier or suggest a means for avoiding deactivation of the peptide by enzymes before it achieves its therapeutic objective.

SUMMARY AND OBJECTS OF THE INVENTION

Accordingly, a major object of the present invention is the provision of a new approach for delivering peptides to the brain using a redox system.

Another object of the invention is to avoid deactivation of peptides by enzymes before the peptides achieve their therapeutic objective.

Yet another object of the invention is to provide a means for "molecular packaging" of peptides which will address the problems of the physical blood-brain barrier as well as the problems of the enzymatic blood-brain barrier.

Another object of the invention is to design a system which will be broadly applicable to the delivery of pharmacologically active peptides by sequential metabolism.

These objects are achieved by placing a pharmacologically active peptide in a molecular environment which disguises its peptide nature. This environment provides a biolabile, lipophilic function to penetrate the blood-brain barrier by passive transport; a dihydropyridine-type redox moiety for targeting the peptide to the brain and providing "lock-in" as the pyridinium salt; and an amino acid or di- or tripeptide spacer between redox moiety and peptide designed to enhance the sequential metabolism of the "molecularly packaged" peptide.

Consistent with the foregoing, the present invention provides "packaged" peptide systems of the formula

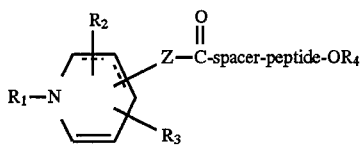

wherein Z is either a direct bond or $C_1$–$C_6$ alkylene and can be attached to the heterocyclic ring via a ring carbon atom or via the ring nitrogen atom; $R_1$ is $C_1$–$C_7$ alkyl, $C_1$–$C_7$ haloalkyl or $C_7$–$C_{12}$ aralkyl when Z is attached to a ring carbon atom; $R_1$ is a direct bond when Z is attached to the ring nitrogen atom; $R_2$ and $R_3$, which can be the same or different, are selected from the group consisting of hydrogen, halo, cyano, $C_1$–$C_7$ alkyl, $C_1$–$C_7$ alkoxy, $C_2$–$C_8$ alkoxycarbonyl, $C_2$–$C_8$ alkanoyloxy, $C_1$–$C_7$ haloalkyl, $C_1$–$C_7$ alkylthio, $C_1$–$C_7$ alkysulfinyl, $C_1$–$C_7$ alkylsulfonyl, —CH=NOR''' wherein R''' is hydrogen or $C_1$–$C_7$ alkyl, and —CONR'R'' wherein R' and R'', which can be the same or different, are each hydrogen or $C_1$–$C_7$ alkyl; or one of $R_2$ and $R_3$ together with the adjacent ring carbon atom forms a benzene ring fused to the heterocyclic ring, which benzene ring may optionally bear one or two substituents, which can be the same or different, selected from the group consisting of hydroxy, protected hydroxy, halo, cyano, $C_1$–$C_7$ alkyl, $C_1$–$C_7$ alkoxy, $C_2$–$C_8$ alkoxycarbonyl, $C_2$–$C_8$ alkanoyloxy, $C_1$–$C_7$ haloalkyl, $C_1$–$C_7$ alkylthio, $C_1$–$C_7$ alkylsulfinyl, $C_1$–$C_7$ alkylsulfonyl, —CH=NOR''' wherein R''' is hydrogen or $C_1$–$C_7$ alkyl, and —CONR'R'' wherein R' and R'', which can be the same or different, are each hydrogen or $C_1$–$C_7$ alkyl; the dotted lines indicate that the compound of formula (I) contains a 1,4- or 1,6-dihydropyridine, a 1,4- or 1,2-dihydroquinoline, or a 1,2-dihydroisoquinoline ring system; "spacer" is an L-amino acid unit or a di- or tripeptide consisting of 2 or 3 L-amino acid units, the N-terminal amino acid of said spacer being bonded to the depicted carbonyl carbon via an amide bond; and "peptide" is a pharmacologically active peptide having 2 to 20 amino acid units, the N-terminal amino acid of said peptide being bonded to the C-terminal amino acid of said spacer via a peptide bond, the C-terminal amino acid of said peptide having an esterified carboxyl function —COOR$_4$ wherein R$_4$ is $C_8$–$C_{22}$ alkyl, $C_8$–$C_{22}$ alkenyl, $C_6$–$C_{30}$ polycycloalkyl —$C_pH_{2p}$— wherein p is 0, 1, 2 or 3, or $C_6$–$C_{30}$ polycycloalkenyl —$C_pH_{2p}$— wherein p is defined as above.

The non-toxic pharmaceutically acceptable salts of the compounds of formula (I) are also within the ambit of this invention.

The molecularly packaged peptides of formula (I) are the reduced, dihydropyridine forms of the new redox system provided by the present invention, and the form intended for administration.

The present invention further provides novel quaternary intermediates to the peptides of formula (I), which intermediates have the structural formula

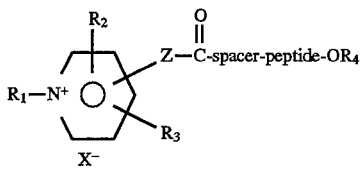

wherein Z, $R_1$, $R_2$, $R_3$, "spacer", "peptide" and $R_4$ are defined as above and $X^-$ is the anion of a non-toxic pharmaceutically acceptable acid. In addition to being chemical intermediates to the corresponding dihydropyridine final products of formula (I), the quaternaries of formula (II) are produced in vivo by enzymatically mediated oxidation of the reduced form (I). The resultant polar conjugate is trapped ("locked-in") behind the lipoidal blood-brain barrier. Over time, cleavage of the lipophilic ester from the oxidized form of the system by esterase or lipase enzymes (which affords the corresponding quaternary conjugates in which the —OR$_4$ group has been replaced with an —OH group, which are likewise "locked in" the brain and which may exert characteristic peptide-like activity) and enzymatic cleavage of the targetor-spacer portion from the peptides results in release of active peptides in the brain.

BRIEF DESCRIPTION OF THE DRAWINGS

Other objects and advantages of the present invention will be apparent from the following detailed description and accompanying drawings, in which.

DETAILED DESCRIPTION OF THE INVENTION AND THE PREFERRED EMBODIMENTS

Figure 1:
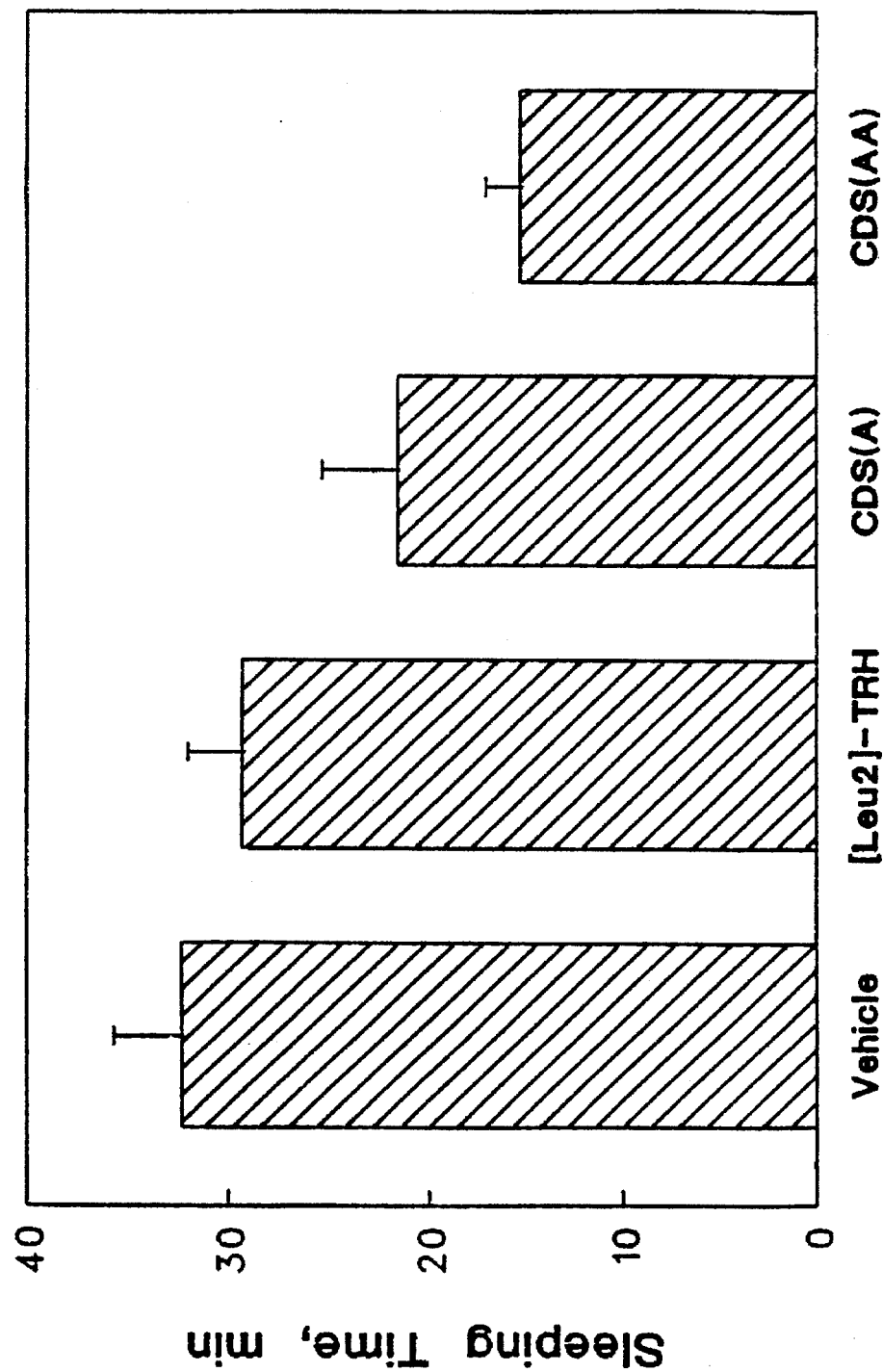
FIG. 1 is a bar graph depicting the effect on methohexital-induced sleeping time in mice in minutes for two representative "packaged" TRH-type peptides of the invention, CDS (A) and CDS(AA), for a TRH analog, [Leu2]-TRH, and for the vehicle following intravenous injection.

More particularly in accord with the present invention, the following definitions are applicable:

The term "lipoidal" as used herein is intended to mean lipid-soluble or lipophilic.

The term "$C_1$–$C_6$ alkylene" as used herein encompasses bivalent radicals of the type —(CH$_2$)$_n$— wherein n is 1 to 6, as well as the corresponding branched chain groups, e.g., methylene, ethylene, propylene, trimethylene, 1,2-butylene, 2,3-butylene, tetramethylene and the like. Preferably, $C_1$–$C_6$ alkylene is —(CH$_2$)$_n$— wherein n is 1 to 4.

The term "halo" encompasses fluoro, chloro, bromo and iodo.

The term "$C_1$–$C_7$ alkyl" includes straight and branched lower alkyl radicals having up to seven carbon atoms. When $R_2$ and/or $R_3$ are $C_1$–$C_7$ alkyl, they are preferably methyl or ethyl. When $R_1$ is $C_1$–$C_7$ alkyl, it is preferably methyl.

The term "$C_1$–$C_7$ alkoxy" includes straight and branched chain lower alkoxy radicals having up to seven carbon atoms. When $R_2$ and/or $R_3$ are $C_1$–$C_7$ alkoxy, they are preferably methoxy or ethoxy.

The term "$C_2$–$C_8$ alkoxycarbonyl" designates straight and branched chain radicals of the formula

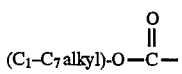

wherein the $C_1$–$C_7$ alkyl group is defined as above. When $R_2$ and/or $R_3$ are alkoxycarbonyl, they are preferably ethoxycarbonyl or isopropoxycarbonyl.

The term "$C_2$–$C_8$ alkanoyloxy" designates straight and branched chain radicals of the formula

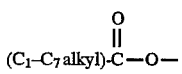

wherein the $C_1$–$C_7$ alkyl group is defined as above. When $R_2$ and/or $R_3$ are alkanoyloxy, they are preferably acetoxy, pivalyloxy or isobutyryloxy.

The term "$C_1$–$C_7$ haloalkyl" designates straight and branched chain lower alkyl radicals having up to seven carbon atoms and bearing one to three halo substituents (F, Cl, Br or I), which can be the same or different. Specific examples of the contemplated monohaloalkyl and polyhaloalkyl groups include chloromethyl, dichloromethyl, trichloromethyl, bromomethyl, fluoromethyl, difluoromethyl, trifluoromethyl, 1-fluoroethyl, 1-chloroethyl, 2-chloroethyl, 2,2,2-trichloroethyl, 2,2,2-trifluoroethyl, 1,2-dichloroethyl, 1-chloropropyl, 3-chloropropyl, 1-chlorobutyl, 1-chloropentyl, 1-chlorohexyl, 4-chlorobutyl and the like. Preferably, the haloalkyl group contains 1 or 2 carbon atoms and bears 1 to 3 halogen substituents, e.g. chloromethyl or trifluoromethyl.

The term "$C_1$–$C_7$ alkylthio" includes straight and branched chain radicals of the type

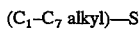

wherein $C_1$–$C_7$ alkyl is defined as before. When $R_2$ and/or $R_3$ are alkylthio, they are preferably methylthio.

The terms "$C_1$–$C_7$ alkylsulfinyl" and "$C_1$–$C_7$ alkylsulfonyl" designate radicals of the formulas

and

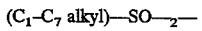

respectively, wherein $C_1$–$C_7$ alkyl is defined as before. When $R_2$ and/or $R_3$ are alkylsulfinyl or alkylsulfonyl, methylsulfinyl and methylsulfonyl are preferred.

When $R_2$ and/or $R_3$ are —CH=NOR''', they are preferably —CH=NOH or —CH=NOCH$_3$.

When $R_2$ and/or $R_3$ are —CONR'R'', they are preferably —CONH$_2$ or —CON(CH$_3$)$_2$.

The term "$C_7$–$C_{12}$ aralkyl" as used herein designates radicals of the type

wherein the aryl portion is phenyl or naphthyl and the alkylene portion, which can be straight or branched, can contain up to 6 carbon atoms, e.g., methylene, ethylene, propylene, trimethylene, 1,2-butylene, 2,3-butylene, tetramethylene and the like. When $R_1$ is aralkyl, it is preferably benzyl.

The expression "non-toxic pharmaceutically acceptable salts" as used herein generally includes the non-toxic salts of compounds of formula (I) formed with non-toxic, pharmaceutically acceptable inorganic or organic acids HX. For example, the salts include those derived from inorganic acids such as hydrochloric, hydrobromic, sulfuric, sulfamic, phosphoric, nitric and the like; and the salts prepared from organic acids such as acetic, propionic, succinic, glucolic, stearic, lactic, malic, tartaric, citric, ascorbic, pamoic, maleic, hydroxymaleic, phenylacetic, glutamic, benzoic, salicyclic, sulfanilic, fumaric, methanesulfonic, toluenesulfonic and the like. The expression "anion of a non-toxic pharmaceutically acceptable acid" as used herein, e.g., in connection with structure (II), is intended to include anions of such organic or inorganic acids HX.

The expression "hydroxyl protective group" as used herein is intended to designate a group (Y) which is inserted in place of a hydrogen atom of an OH group or groups in order to protect the OH group(s) during synthesis and/or to improve lipoidal characteristics and prevent premature metabolism of the OH group(s) prior to the compound's reaching the desired site in the body. The expression "protected hydroxy substituent" designates an OY group wherein Y is a "hydroxyl protective group" as defined above. Preferably, however, the redox portion of the molecule does not bear either a hydroxy or protected hydroxy group. Such protective groups are, on the other hand, frequently used during synthesis of the "spacer-peptide" section of the molecule and occasionally are retained in the final product if it contains a particularly vulnerable hydroxy function.

Typical hydroxyl protective groups contemplated by the present invention are acyl groups and carbonates. When the hydroxyl protective group is acyl (i.e., when it is an organic radical derived from a carboxylic acid by removal of the hydroxyl group), it preferably represents an acyl radical selected from the group consisting of alkanoyl having 2 to 8 carbon atoms; alkenoyl having one or two double bonds and 3 to 8 carbon atoms;

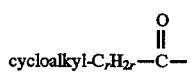

wherein the cycloalkyl portion contains 3 to 7 ring atoms and r is zero, one, two or three; phenoxyacetyl; pyridinecarbonyl; and

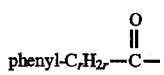

wherein r is zero, one, two or three and phenyl is unsubstituted or is substituted by 1 to 3 alkyl each having 1 to 4 carbon atoms, alkoxy having 1 to 4 carbon atoms, halo, trifluoromethyl, dialkylamino having 2 to 8 carbon atoms or alkanoylamino having 2 to 6 carbon atoms.

When the acyl group is alkanoyl, there are included both unbranched and branched alkanoyl, for example, acetyl, propionyl, butyryl, isobutyryl, valeryl, isovaleryl, 2-methylbutanoyl, pivalyl (pivaloyl), 3-methylpentanoyl, 3,3-dimethylbutanoyl, 2,2-dimethylpentanoyl and the like. Pivalyl, isobutyryl and isovaleryl are especially preferred.

When the acyl group is alkenoyl, there are included, for example, crotonyl, 2,5-hexadienoyl and 3,6-octadienoyl.

When the acyl group is

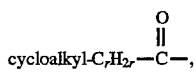

there are included cycloalkanecarbonyl and cycloalkanealkanoyl groups wherein the cycloalkane portion can optionally bear 1 or 2 alkyl groups as substituents, e.g., cyclopropanecarbonyl, 1-methylcyclopropanecarbonyl, cyclopropaneacetyl, α-methylcyclopropaneacetyl, 1-methylcyclopropaneacetyl, cyclopropanepropionyl, α-methylcyclopropanepropionyl, 2-isobutylcyclopropanepropionyl, cyclobutanecarbonyl, 3,3-dimethylcyclobutanecarbonyl, cyclobutaneacetyl, 2,2-dimethyl-3-ethylcyclobutaneacetyl, cyclopentanecarbonyl, cyclohexaneacetyl, cyclohexanecarbonyl, cycloheptanecarbonyl and cycloheptanepropionyl. Cyclohexanecarbonyl is especially preferred.

When the acyl group is pyridinecarbonyl, there are included picolinoyl (2-pyridinecarbonyl), nicotinoyl (3-pyridinecarbonyl) and isonicotinoyl (4-pyridinecarbonyl).

When the acyl group is

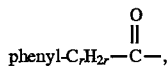

there are included, for example, benzoyl, phenylacetyl, α-phenylpropionyl, β-phenylpropionyl, p-toluyl, m-toluyl, o-toluyl, o-ethylbenzoyl, p-tert-butylbenzoyl, 3,4-dimethylbenzoyl, 2-methyl-4-ethylbenzoyl, 2,4,6-trimethylbenzoyl, m-methylphenylacetyl, p-isobutylphenylacetyl, β-(p-ethylphenyl)propionyl, p-anisoyl, m-anisoyl, o-anisoyl, m-isopropoxybenzoyl, p-methoxyphenylacetyl, m-isobutoxyphenylacetyl, m-diethylaminobenzoyl, 3-methoxy-4-ethoxybenzoyl, 3,4,5-trimethoxybenzoyl, p-dibutylaminobenzoyl, 3,4-diethoxyphenylacetyl, β(3,4,5-trimethoxyphenyl)propionyl, o-iodobenzoyl, m-bromobenzoyl, p-chlorobenzoyl, p-fluorobenzoyl, 2-bromo-4-chlorobenzoyl, 2,4,6-trichlorobenzoyl, p-chlorophenylacetyl, α-(m-bromophenyl)propionyl, p-trifluoromethylbenzoyl, 2,4-di(trifluoromethyl)benzoyl, m-trifluoromethylphenylacetyl, β-(3-methyl-4-chlorophenyl)propionyl, p-dimethylaminobenzoyl, p-(N-methyl-N-ethylamino)benzoyl, o-acetamidobenzoyl, m-propionamidobenzoyl, 3-chloro-4-acetamidophenylacetyl, p-n-butoxybenzoyl, 2,4,6- triethoxybenzoyl, β-(p-trifluoromethylphenyl)propionyl, 2-methyl-4-methoxybenzoyl, p-acetamidophenylpropionyl and 3-chloro-4-ethoxybenzoyl.

When the hydroxyl protective group is a carbonate grouping, it has the structural formula

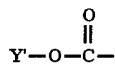

i.e., it is an organic radical which can be considered to be derived from a carbonic acid by removal of the hydroxyl group from the COOH portion. Y' preferably represent alkyl having 1 to 7 carbon atoms; alkenyl having one or two double bonds and 2 to 7 carbon atoms;

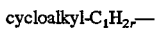

wherein the cycloalkyl portion contains 3 to 7 ring atoms and r is zero, one, two or three; phenoxy; 2-, 3-, or 4-pyridyl; or

wherein r is zero, one, two or three and phenyl is unsubstituted or is substituted by 1 to 3 alkyl each having 1 to 4 carbon atoms, alkoxy having 1 to 4 carbon atoms, halo, trifluoromethyl, dialkylamino having 2 to 8 carbon atoms or alkanoylamino having 2 to 6 carbon atoms. Most preferably, Y' is $C_1-C_7$ alkyl, particularly ethyl or isopropyl.

The term "$C_8-C_{22}$ alkyl" as used herein for $R_4$ represents the alkyl portion of saturated fatty alcohols, usually straight chain, for example, octyl, decyl, lauryl, myristyl, cetyl and stearyl.

The term "$C_8-C_{22}$ alkenyl" as used herein for $R_4$ represents the alkenyl portion of unsaturated fatty alcohols, for example, oleyl, linoleyl and linolenyl.

The polycycloalkyl-$C_pH_{2p}$— radicals represented by $R_4$ are bridged or fused saturated alicyclic hydrocarbon systems consisting of two or more rings, optionally bearing one or more alkyl substituents and having a total of 6 to 30 carbon atoms in the ring portion, including the possible alkyl substituents but not including the carbon atoms in the —$C_pH_{2p}$— portion. The corresponding bridged or fused unsaturated alicyclic hydrocarbon systems are intended by the term "$C_6-C_{30}$ polycycloalkenyl —$C_pH_{2p}$—". In both cases, p is preferably 0, 1 or 2. Such polycycloalkyl and polycycloalkenyl radicals are exemplified by adamantyl (especially 1- or 2-adamantyl), adamantylmethyl (especially 1-adamantylmethyl), adamantylethyl (especially 1-adamantylethyl), bornyl, norbonyl, (e.g., exo-norbornyl or endo-norbornyl), norbornenyl (e.g., 5-norbornen-2-yl), norbornylmethyl (e.g., 2-norbornylmethyl) and norbornylethyl (e.g., 2-norbornylethyl), decahydronaphthyl (e.g., cis or trans decahydronaphthyl-2-yl), 6,6-dimethylbicyclo [3.1.1] hept-2-en-2-ethyl, (±)-(3-methylnorborn-2-yl)methyl, 1,3,3-trimethyl-2-norbornyl and 5-norbornene-2-methyl; and by radicals of the type

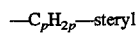

where p is defined as above but is preferably zero, and "steryl" is the residue of a steroidal alcohol, i.e., the portion which would remain after removal of the hydroxy group therefrom. Such residues are introduced into the formula (I) or (II) compounds, or more preferably their synthetic precursors, by reacting the carboxyl group of what will ultimately be the C-terminal amino acid of the peptide with the selected alcohol; for example, in the case of the steryl residues, with an alcohol of the androstane, pregnane or cholestane series. The following structures are representative:

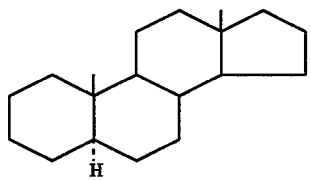

androstanes/androstenes
-$\Delta^5$-3β, 17 β-diol
-$\Delta^{16}$-3 α-ol
-3α-ol-17-one
-3β-ol-17-one

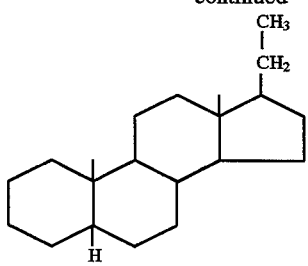

pregnanes/pregnenes
-3α, 20-diol
-3α-ol-20-one
-Δ⁴-21-ol-3,11-dione
-Δ⁴-17α, 20, 21-triol-3-one
-Δ⁵-3β-ol-20-one

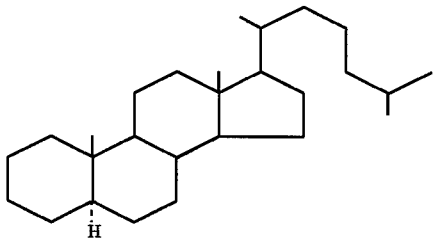

cholestanes/cholestenes
-3β-ol
-Δ⁵-3β-ol (cholesterol)

Other suitable steryl groups $R_4$ can be derived from sitosterols ($\alpha_1$-sitosterol, β-sitosterol, γ-sitosterol). Preferably, the steroid from which the steryl group is derived is fairly innocuous, i.e., pharmacologically inactive and naturally occurring. However, in selected instances, an active steroid, particularly a naturally occurring active steroid, may be selected. For example, it is now recognized that estrogen may be useful in the treatment of neurodegenerative diseases; thus, where the "peptide" portion of the compounds of this invention is intended for use in such disease states, an $R_4$ group derived from an estrogen (such as estrodiol, estriol or estrone) may be especially suitable. When the selected steroidal alcohol has more than one hydroxyl function, a mixture of products will typically result although reaction may occur primarily at one location, e.g., the 17-position in the case of the aforenoted estrogens. It is therefore often preferred to select a steroidal starting material which contains only one reactive hydroxyl function. Also within the ambit of the definition of $R_4$ herein are residues of alcohols which assume steroidal conformations; for example, in addition to the residue of the steroid ergosterol, the residue of its active product calciferol (Vitamin $D_2$) may be utilized; in addition to the residue of the steroid 7-dehydrocholesterol, the residue of its active product cholecalciferol (Vitamin $D_3$) may be selected as an $R_4$ group herein. Other specific alcohols to be employed to generate the $R_4$ group in formulas (I) and (II) and their precursors are noted later in this description.

Especially preferred compounds of the present invention are the "packaged" peptides of formula (I) in which the portion of the molecule has one of the following structures:

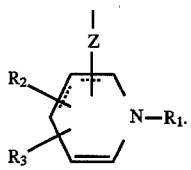

portion of the molecule has one of the following structures:

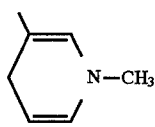
(a)

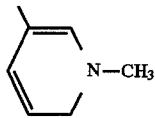
(b)

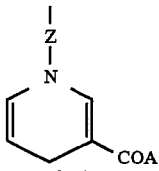
(c)

A: preferably
—NH₂ or
—O($C_1$–$C_7$alkyl)

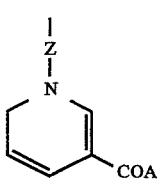
(d)

A: defined with (c)

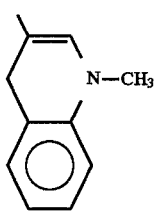
(e)

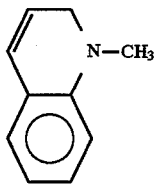
(f)

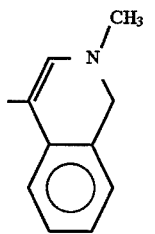
(g)

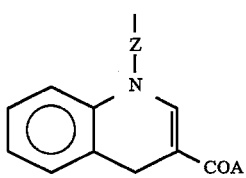

A: defined with (c)

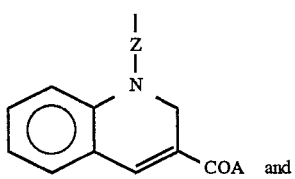

A: defined with (c)

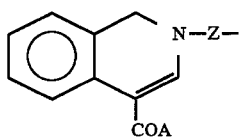

A: defined with (c)

In the above structures, (a), (b), (e), (f) and (g), Z in formula (I) is a direct bond; in the remaining structures, Z is preferably —(CH$_2$)— or —(CH$_2$)$_2$—. —COA is preferably —CONH$_2$ or —COOC$_2$H$_5$. The corresponding quaternary salts of formula (II) have the partial structures:

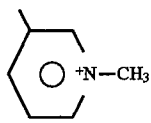

(a'/b')

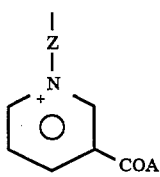

(c'/d')

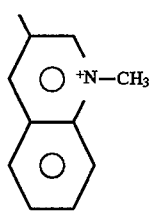

(e'/f')

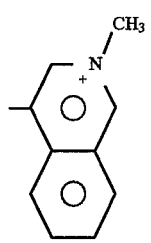

(g')

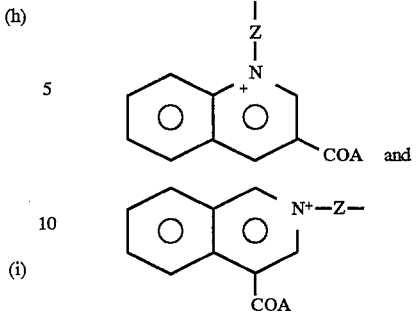

(h)

(i)

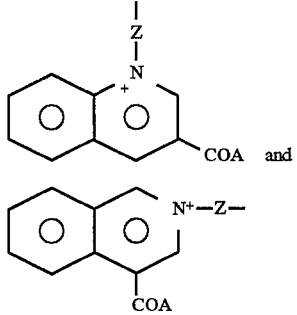

(h'/i')

(j')

wherein Z is preferably as defined with structures (a) through (j).

The expression "carboxyl protective group" as used herein is intended to designate a group (W) which is inserted in place of a hydrogen atom of a COOH group or groups in order to protect the COOH group(s) during synthesis and/or to improve lipoidal characteristics and prevent premature metabolism of said COOH group or groups prior to the compound's reaching the desired site in the body, but excluding the C-terminal position in formulas (I) and (II), at which location an R$_4$ group has been incorporated. Typical of such other carboxyl protective groups W are the groups encompassed by Y' above, especially C$_1$–C$_7$ alkyl, particularly ethyl, isopropyl and t-butyl. Such groups are not intended for use in place of R$_4$, as they are ineffective. Contrariwise, groups as defined by R$_4$ hereinabove can of course be used at additional locations, since these are especially lipophilic groups intended for use in vivo. However, it is not ordinarily necessary to use such group other than at the C-terminal location. Usually, carboxyl protecting for other positions are solely for protection during synthesis, and then only the usual synthetic requirements will generally apply.

Carboxyl protecting groups for use in peptide synthesis are well-known to those skilled in the art. See, for example, M. Bodanszky, *Principles of Peptide Synthesis*, Springer-Verlag, New York 1984, Ives U.S. Pat. No. 4,619,915 and the various publications on peptide chemistry referred to in the Ives patent. See also *Methoden der Organischen Chemie*, Houben-Weyl, Volume 15/1 for protecting groups and Volume 15/2 for methods of peptide synthesis. Representative carboxyl protecting groups for synthetic purposes include various silyl esters (e.g., trialkylsilyl and trihalosilyl esters), alkyl esters (e.g., tert-butyl esters), benzyl esters and the other carboxyl protecting groups mentioned in the Ives patent.

The expression "amino protective group" as used herein is intended to designate a group which is inserted in place of a hydrogen atom of an amino group or groups in order to protect the amino group(s) during synthesis. Appropriate amino protecting groups are known in the art and are described, for example, in the Bodanszky, Ives and Houben-Weyl references cited above. Representative amino protecting groups for synthetic use include acyl groups such as tert-butoxycarbonyl, benzyloxycarbonyl, benzoyl, acetyl and the like. Yet other conventional amino protecting groups for use in synthesis are described in the literature, e.g., in the Bodanszky publication and Ives patent referred to hereinabove.

The various protecting groups for hydroxyl, carboxyl and amino functions discussed above can be substituted for the hydroxyl, carboxyl and amino functions in the instant peptides or their precursor molecules by methods well-known in the art. Methods for chemical removal of the protecting groups (when such are not to be retained in the pharmaceutically useful end product) are likewise well-known to those skilled in the art. Typically, amine protecting groups are chemically removed by acidolysis (acid hydrolysis) or hydrogenation, depending on the particular protecting group employed. Hydroxyl and carboxyl protecting groups are typically removed chemically by acid or base hydrolysis. Protecting groups which are incorporated in the pharmaceutical end product must be amenable to hydrolytic or metabolic cleavage in vivo.

The "spacer" portion of the compounds of the invention is composed of from 1 to 3 L-amino acid units. Each unit is a naturally occurring L-amino acid. Any natural amino acid may be present as each of the 1 to 3 units, which may be the same or different; however, those which have excess reactive functional groups beyond those needed to attach to the redox moiety at one end and the rest of the peptide at the other may be disadvantageous as compared to the neutral amino acids (e.g., glycine, alanine, valine, leucine, isoleucine, phenylalanine, proline, tryptophan, asparagine and glutamine). Preferred amino acid segments are alanine, proline, glycine and phenylalanine. Preferred spacers include Ala, Ala-Ala, Ala-Pro, Pro, Pro-Pro and Pro-Ala. Spacers utilizing alanine and proline segments are particularly preferred because there are peptidases which specifically cleave between alanine and an adjacent amino acid and between proline and an adjacent amino acid. For example, alanine-aminopeptidase and proline-endopeptidase facilitate cleavage of the pharmacologically active peptide from a spacer having those amino acids, in addition to numerous less specific degrading enzymes for which any of the "packaged" peptides serve as substrates.

The "peptide" portion of the compounds of the invention is a pharmacologically active peptide; this is typically a known, naturally occurring bioactive peptide (including a bioactive fragment of a known, naturally occurring peptide) or a known bioactive synthetic peptide (particularly one which is an analog of a naturally occurring bioactive peptide). In any case, the peptide has 2–20 amino acid units. Naturally, in order for the brain specificity/sustained in-brain activity of the compounds of formula (I) to be of value, the peptide which is molecularly "packaged" into a formula (I) compound should exert a useful central activity, i.e., it should exert a significant pharmacological action in the central nervous system such that it may be used as a drug, that is, for the diagnosis, cure, mitigation, treatment or prevention of disease or in the enhancement of desirable physical or mental development and conditions in man or animals, or it should be convertible in vivo to a peptide having a useful central activity.

Appropriate known peptides for derivation/"packaging" in accord with the present invention include naturally occurring peptides such as kyotorphin, TRH, met$^5$-enkephalin, leu$^5$-enkephalin, vasopressin, oxytocin, neurotensin, ACTH fragments, peptide T, substance P, angiotensin and LH-RH, and/or their biologically active fragments or synthetic analogs.

It will be apparent from the structures of the natural peptides and their analogs, that in some cases the peptides may not have a free amino group on the N-terminus for attachment of the redox-spacer portions of formula (I) and/or the peptides may not have a free carboxyl group on the C-terminus for esterification to the corresponding bulky ester grouping. In such cases, appropriate modification of the peptide molecule may be made to make it amenable to molecular "packaging" without substantial loss of activity. Typical modifications are discussed hereinbelow in conjunction with specific peptides.

In the following discussion of peptides suitable for "packaging" in accord with the present invention, the conventional peptide representation (amino terminus on left, carboxyl terminus on right) will be used, as will the conventional abbreviations for the individual amino acid units (Phe for phenylalanine, Gly for glycine, Gln for glutamine etc.). Insofar as concerns configuration, in this general discussion the configuration of optically active amino acids will be assumed to be L unless otherwise specified.

Kyotorphin is an endogenous dipeptide of the structure H-Tyr-Arg-OH which has analgesic properties. It has been found to stimulate the release of enkephalin. The corresponding dipeptides in which one or both amino acids has/have the D-configuration also have activity. Kyotorphin and its D-amino acid containing analogs are suitable for molecular "packaging" in accord with the present invention without modification of the basic peptide structure.

Thyrotropin releasing hormone (TRH) is a tripepride of the formula PyroGlu-His-Pro-NH$_2$. It is the primary neurotrophic hormone for TSH secretion and it plays other roles in nervous system physiology. It is known to have analeptic activity, reducing pentobarbital-induced sleeping time as well as ethanol-induced sleeping. It has been shown to have positive effects on memory in patients with probable Alzheimer's disease and may be used in treating mental depression and amyotrophic lateral sclerosis. TRH does not have free amino and carboxyl termini. However, conversion of the analog [SEQ. ID NO. 1] pGlu-His-Pro-Gly to TRH has been previously demonstrated. Glutamine has been shown to be the precursor of the N-terminal pyroglutamyl residue. Thus, the analog [SEQ. ID NO. 2] Gln-His-Pro-Gly becomes a variation suitable for molecular "packaging" herein. Similarly, the TRH analog, PyroGlu-Leu-Pro-NH$_2$ can be modified to Gln-Leu-Pro-Gly so that it can be molecularly "packaged" in accord with the present invention. Since the His residue of TRH is not essential for CNS activity, analogs in which it has been replaced, e.g., with leucine, are preferred for use herein.

The enkephalins are two naturally occurring pentapeptides belonging to the endorphin class. Met$^5$-enkephalin has the structure [SEQ. ID NO. 4]

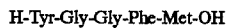

while Leu$^5$-enkephalin has the structure [SEQ. ID NO. 5]

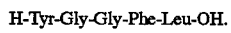

The most important property of the enkephalins is their morphine-like analgesic action. They also have a variety of effects on memory, and thus may be useful in treating Alzheimer's disease and other neurodegenerative disorders.

Some peptides slightly larger than the enkephalins with intrinsic opiate activity have also been identified. These include Met$^5$-enkephalin-Arg$^6$ and Met$^5$-enkephalin-Lys6, which are believed to be potential precursors of Met$^5$-enkephalin; and Met$^5$-enkephalin-Arg$^6$-Phe$^7$, which has high affinity for K-opiate receptors.

Moreover, many enkephalin analogs have been synthesized (e.g., FK-33-824, Ly 127623/metkephamid, Wy-42, 896) and structure/activity relationships have been analyzed. See, in particular, J. S. Morley, *Annu. Rev. Pharmacol.* 20: 81–110 (1980), incorporated by reference herein in its entirety and relied upon. While virtually every position in the enkephalin chain allows some variation without loss of activity, some positions allow much more variation than other. Thus, in the case of N-terminal substitution, activity can be maintained in the same range by addition of an L-amino acid. The Gly$^2$ position appears to be particularly amenable to variation, and replacement with a D-amino acid often has been found to lead to a marked increase in potency and/or longer biological half-life. Also, structural/conformational changes at the Met$^5$/Leu$^5$ position, i.e., replacing Met$^5$ or Leu$^5$ with a different amino acid (L or D), have afforded analogs which are invariably active, although increases in potency as the result of such changes are modest. In addition, contraction or extension at the C-terminus has afforded active analogs. Thus, many enkephalin analogs exist which can be molecularly "packaged" in accord with the present invention. The analogs in which Gly$^2$ has been replaced with a D-amino acid and Met$^5$/Leu$^5$ has been replaced with a D-amino acid are of particular interest, e.g., [SEQ. ID NO. 6] H-Tyr-D-Ala-Gly-Phe-D-Leu-OH.

Vasopressin and oxytocin are cyclic peptides which differ from each other in only two amino acids. All mammalian oxytocin (OXT) has the structure [SEQ. ID NO. 7]

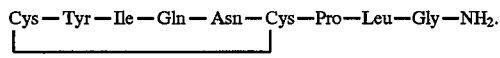

Most vasopressin is arginine-vasopressin (AVP), which has the structure [SEQ. ID NO. 8]

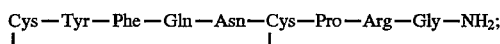

swine vasopressin (SVP) is also known as lysine-vasopressin and has the structure [SEQ. ID NO. 9]

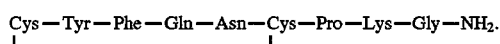

Vasopressin appears to enhance retention of learned responses and to enhance attention and memory. Both oxytocin and vasopressin may be involved in pain mechanisms. In vasopressin, residues 2, 3 and 5 seem to be fairly critical for activity, especially asparagine at 5. Most of the activity in vasopressin and oxytocin seems to be in the covalent ring structure. Removing the C-terminal glycinamide appears to eliminate most peripheral effects (such as on blood pressure) but not to affect behavior. Behaviorally active fragments include H-Pro-Arg-Gly-NH$_2$, H-Lys-Gly-NH$_2$, AVP$_{1-7}$ (pressinamide), OXT$_{1-8}$, OXT$_{1-7}$, OXT$_{1-6}$, Pro-Leu-Gly-NH$_2$ and Leu-Gly-NH$_2$. Thus, in the case of vasopressin and its analogs, the C-terminal Gly-NH$_2$ will be replaced with glycine or the chain will be shortened so that leucine or proline becomes the C-terminal amino acid in order to adapt these peptides to "packaging". While the amino acids at 8 and 9 can be removed, shortening to 6 or 7 amino acids appears to cause a change in activity, at least in the case of oxytocin, where OXT$_{1-7}$ and OXT$_{1-6}$ affect memory differently from OXT. In the case of vasopressin, shortening to 7 amino acids (des-Gly$^9$-Lys$^8$- or des-Gly$^9$-Arg$^8$-vasopressin) reduces peripheral effects while still markedly facilitating effects on memory. Thus, a particularly interesting vasopressin fragment for molecular "packaging" herein is [SEQ. ID NO. 10]

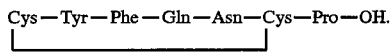

For the various types of memory processes which respond to vasopressin and other neuropeptides, see D. DeWied, J. M. van Ree, Life Sci 22, 975–985 (1983).

Neurotensin (NT) is a basic tridecapeptide of the formula [SEQ. ID NO. 11]

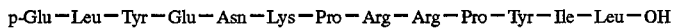

which has a variety of hormone-like activities. It has been shown to induce hypotension. It also acts as a CNS neurotransmitter and appears to be a very potent analgesic. The carboxy terminal leucine moiety appears to be essential for binding and the arginine residues at 8 and 9 also are essential for binding and biological activity. Very little variation as positions 11, 12 and 13 seems to be possible. Xenopsin, an octapeptide which shares many properties with neurotensin, has the structure [SEQ. ID NO. 12]

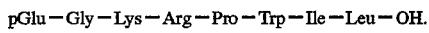

Other potent neurotensin analogs include D-Tyr$^{11}$-NT and D-Phe$^{11}$-NT. Thus, neurotensin and its analogs need to be modified at the N-terminus, typically by replacing p-Glu with glutamine, in order to be adapted to the molecular "packaging" provided by the present invention.

ACTH, or adrenocorticotropic hormone, has complex behavioral activities involving learning, memory, motivation, arousal and attention. It has 39 amino acids, but its essential structure is believed to be ACTH$_{4-7}$, with phenylalanine in position 7 playing a key role in behavioral effects. Human ACTH$_{1-39}$ has the structure [SEQ. ID NO. 13]:

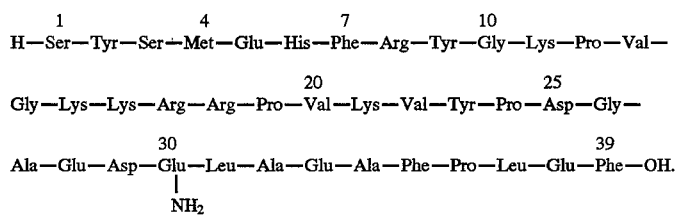

Active fragments include ACTH$_{4-10}$ and ACTH$_{4-7}$, with ACTH$_{4-7}$ being the shortest peptide found to give the typical behavioral effects of ACTH. A very active ACTH$_{4-9}$ analog, Org 2766, has the structure [SEQ. ID NO. 14]

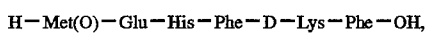

which has an oxidized methionine at 4, D-lysine at 8 in place of arginine, and phenylalanine at 9 in place of tryptophan. It shows 1000 fold potentiation, with dissociation of behavioral effects from endocrine metabolic and opiate-like activities; in clinical studies, it has been found to significantly improve mood in aged subjects. Other active analogs include D-Phe⁷-ACTH$_{1-10}$, D-Phe⁷-ACTH$_{4-7}$ and D-Phe⁷-ACTH$_{4-10}$, although in some ways these analogs behave oppositely from the natural L-forms. While all of the aforementioned fragments and analogs have suitable N- and C-termini for molecular "packaging", preferred fragments and analogs are ACTH$_{4-10}$, ACTH$_{4-7}$, the ACTH$_{4-9}$ analog Org 2766 and D-Phe⁷-ACTH$_{4-10}$.

Peptide T is an octapeptide with anti-AIDS activity. Substance P is an undecapeptide which acts as a vasodilator and a depressant, and can produce analgesia and hyperalgesia. It plays an important role in nervous system function. Substance P has the structure [SEQ. ID NO. 15]

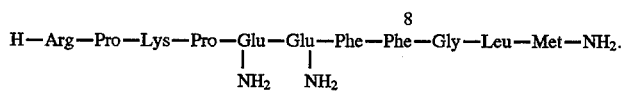

It appears that most structural variation can occur at positions 1 to 6, with some variation also possible at 8. Active analogs include physalaemin, which has the structure [SEQ. ID NO. 16]

pGlu—Ala—Asp—Pro—Asn—Lys—Phe—Tyr—Gly—Leu—Met—NH₂;

eledoisin, which has the structure [SEQ. ID NO. 17]

pGlu—Pro—Ser—Lys—Asp—Ala—Phe—Ile—Gly—Leu—Met—NH₂;

and kossinin, which has the structure [SEQ. ID NO. 18]

Asp—Val—Pro—Lys—Ser—Asp—Gln—Phe—Val—Gly—Leu—Met—NH₂.

In Substance P and all of the aforementioned analogs, it is of course necessary to change the C-terminal Met-NH₂ to Met-OH in order to adapt these peptides to "packaging". Analogs such as physalaemin and eledoisin also need to be modified at the N-terminus, e.g., by replacing pGlu with Gln (glutamine) to adapt them to molecular "packaging".

Moreover, a series of retro-inverso C-terminal hexapeptide analogs of Substance P has been recently described by Verdini et at., U.S. Pat. No. 4,638,046, dated Jan. 20, 1987, incorporated by reference herein and relied upon. Verdini et al. describe compounds of the formula

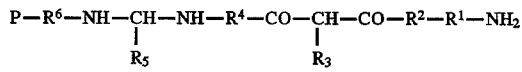

in which P is a hydrogen atom, a linear or branched aliphatic alkyl group with 1–6 carbon atoms, or a saturated or unsaturated linear or branched chain aliphatic acyl group such as formyl, acetyl, propionyl, n-butyryl, isobutyryl, n-valeryl, isovaleryl, hexanoyl, isohexanoyl, heptanoyl, octanoyl, crotonoyl, methacryloyl, acryloyl; or a substituted acyl group such as hydroxyacetyl, 2-hydroxypropionyl, 3-hydroxypropionyl, aminoacetyl, 4-hydroxyphenylacetyl, 4-hydroxyphenylpropionyl, 2-aminopropionyl, 3-aminopropionyl, O-ethylmalonyl, ethoxyformyl, methoxyacetyl, 3-methoxypropionyl, 3-ethoxypropionyl, chloroacetyl, dichloroacetyl, 2-chloropropionyl, 3-chloropropionyl, 2,3-dichloropropionyl, bromoacetyl, 4-hydroxy-3,5-diiodophenylacetyl, 3-oxobutyryl, 3-oxovaleryl, 4-oxovaleryl, methylthioacetyl, 3-methylthiopropionyl, ethylthioacetyl, 3-ethylthiopropionyl, nicotinoyl, 4-aminobutyryl, N$^\alpha$-[(1-(9-adenyl)β-D-ribofuranuronosyl)], N$^\alpha$-[(1-(9-hypoxanthyl)-β-D-ribofuranuronosyl]; or a group such as benzyloxycarbonyl, tert-butyloxycarbonyl, tert-amyloxycarbonyl, isobomyloxycarbonyl, adamantyloxycarbonyl, or chloro or nitro-substituted benzyloxycarbonyl;

R¹ is a residue of methionine, methionine sulphoxide, methionine sulphone, selenomethionine, leucine, norleucine, valine or norvaline;

R² is a residue of leucine, norleucine, valine, norvaline, alanine or isoleucine;

R³ is a hydrogen atom or methyl;

R⁴ is an amino acid residue of D configuration such as phenylalanine, tryptophan, tyrosine, valine, norvaline, leucine, norleucine, isoleucine, serine or derivatives, threonine or derivatives, histidine or derivatives, methionine, methionine-S-methyl, methionine sulphone, arginine or derivatives, lysine or derivatives, ornithine or derivatives, 2,4-diaminobutyric acid or derivatives, 2,3-diaminopropionic acid or derivatives, glutamic acid or aspartic acid or their suitable derivatives;

R⁵ is a hydrogen atom or the side-chain of amino acids such as phenylalanine, tyrosine, 4-chlorophenylalanine, O-benzyltyrosine (or their acetyl, cyclopentyl, tert-butyloxycarbonyl or 4-hydroxyphenylacetyl derivatives);

R⁶ is an amino acid residue such as glutamine or derivatives, pyroglutamic acid, alanine, tyrosine, lysine or derivatives, proline, N-formyl-proline, β-alanine, N-acetyl-β-alanine, glycine, desaminophenylalanine, desaminoaspartic acid, methyldesaminoaspartic acid, or glutamic acid esters represented by the general formula

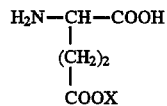

in which X is methyl, ethyl, methoxyethyl or methoxy (ethoxy)$_n$ethyl wherein n=1, 2 or 3.

The Verdini et al. analogs show variations possible in the amino acids corresponding to positions 6, 7 and 9–11 of Substance P, substantial variations at position 8 of Substance P ($R^4$ of Verdini et al.) using a wide variety of D amino acid residues, and the ability to delete the first five amino acids in Substance P without loss of activity. To adapt the Verdini et la. analogs to molecular "packaging" herein, the $P-R_6$ portion of the molecule should be selected such that the N-terminal amino acid has a free primary or secondary amine group for addition of the redox-spacer portion, and the C-terminal $R^1-NH_2$ group should be converted to $R^1-OH$ for addition of the bulky lipophilic ester portion.

A group of biologically active heptapeptides has been recently described by deCastiglione et al., U.S. Pat. No. 4,567,162, dated Jan. 28, 1986, incorporated by reference herein and relied upon. These peptides are said to display activity on the central nervous system and to be useful in promoting growth activity and improving feed efficiency in animals. The compounds have the general formula [SEQ. ID NO. 19]

wherein:

X represents a hydrogen atom or a terminal nitrogen protecting group of acyl, aliphatic urethane, aromatic urethane, alkyl or aralkyl type;

A represents a neutral L-α-amino acid residue; and

Y represents a hydroxy group, an amino group or a group of the formula OR, NHR, $NR_2$ or NH—N—H—R' wherein R represents a straight chain, branched chain or cyclic (including fused or bridged rings) alkyl group having up to 11 carbon atoms which may be unsubstituted or independently substituted by a hydroxy or amino group or a halogen atom, an aralkyl group having from 7 to 14 carbon atoms or a phenyl group; and R' represents a hydrogen atom, any of the groups which R may represent, a straight chain, branched chain or cyclic aliphatic acyl group having from 1 to 11 carbon atoms which may be unsubstituted or independently substituted by a hydroxy or an amino group or a halogen atom, an aromatic acyl group which may be unsubstituted or independently substituted by a hydroxy or amino group or a halogen atom, a straight chain, branched chain or cyclic aliphatic urethane type group having from 3 to 11 carbon atoms, or an aromatic urethane type group.

Thus, a significant amount of variation is possible in the structure of the seventh, or terminal amino acid, A. To adapt the deCastiglione et al. compounds to molecular "packaging", those peptides should be selected wherein X is hydrogen and Y is —OH.

Angiotensin is a pressor substance. Angiotensin I, a decapeptide, is converted to the active pressor agent, angiotensin II, by splitting off the C-terminal His-Leu residues. The octapeptide II differs among species at position 5 (Val or Ile). The active angiotensin is hypotensive and may increase the effectiveness of endogenous norepinephrine. These peptides have the following structures [SEQ. ID NO. 20–21]:

Angiotensin I:

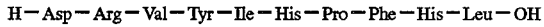

Angiotensin II:

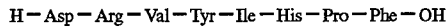

and do not need to be modified at either N- or C-terminus in order to be molecularly "packaged".

LH-RH, or GnRH, is the luteinizing hormone-releasing factor. It is the neurohumoral hormone produced in the hypothalamus which stimulates secretion of LH and FSH, which in turn regulate functioning of the gonads (by stimulating production of steroid hormones) and regulate gamete production and maturation. LH-RH is a decapeptide having the structural formula [SEQ. ID NO. 22]

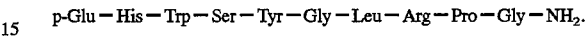

The N- and C-termini can be modified to glutamine and glycine, respectively, in order for LH-RH to be "packed" in accord with the present invention.

Agonist analogs of LH-RH may be used to control fertility in two different ways. Thus, low doses of LH-RH analogs can be used to stimulate ovulation in the female as well as spermatogenesis and androgen production it the male. Larger doses of LH-RH analogs, especially long-acting, highly potent analogs, paradoxically block ovulation and suppress spermatogenesis. In domestic animals, the latter effect promotes weight gain and generally acts as a sterilant. Antagonistic analogs of LH-RH, i.e., analogs which are antagonistic to the normal function of LH-RH, may be used as male or female contraceptives, in the treatment of endometriosis and precocious puberty in females and in the treatment of prostatic hypertrophy in males. Basically, the antagonist analogs are used to inhibit the production of gonadotropins and sex hormones, which is essentially the same as the high dose, paradoxical effect of the agonist analogs.

It is now well-known that the glycine residue in the 6-position of LH-RH can be replaced by a variety of D-amino acids to give LH-RH agonists and antagonists of much greater potency than the natural hormone itself. Other changes which have resulted in substantial increase or retention of activity include eliminating $Gly-NH_2$ at the 10-position to give a nonapeptide as an alkyl-, cycloalkyl- or fluoroalkylamide; replacing $Gly-NH_2$ at the 10-position with an α-azaglycine amide; replacing Leu at the 7-position with N-methyl-leucine; replacing Trp at the 3-position with 3-(1-naphthyl)-L-alanyl or with 3-(2-naphthyl)-L-alanyl; and replacing Tyr at the 5-position with phenylalanyl or with 3-(1-pentafluorophenyl)-L-alanyl. These analogs need to be modified as noted for LH-RH above in order to be adapted to molecular "packaging".

Numerous LH-RH analogs, most frequently nonapeptides and decapeptides, have been developed to date. For example, Nestor et al., U.S. Pat. No. 4,530,920, dated Jul. 23, 1985, incorporated by reference herein in its entirety and relied upon, provides nonapeptide and decapeptide agonist analogs of LH-RH which have the formula [SEQ. ID NO. 23]

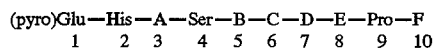

and the pharmaceutically acceptable salts thereof, wherein:

A is tryptophyl, phenylalanyl, 3-(1-naphthyl)-L-alanyl or 3-(2-naphthyl)-L-alanyl;

B is tyrosyl, phenylalanyl or 3-(1-pentafluoro-phenyl)-L-alanyl;

C is an amino acyl residue selected from the group consisting of the radicals represented by the following structural formulas:

(a)

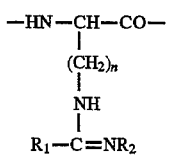

wherein n is 1 to 5;

R₁ is alkyl of 1 to 12 carbon atoms, —NRR₃ wherein R is hydrogen or alkyl of 1 to 4 carbon atoms, R₃ is hydrogen, alkyl of 1 to 12 carbon atoms, cycloalkyl, fluoroalkyl, phenyl, benzyl, —(CH₂)$_n$-morpholino or —(CH₂)$_n$N(R₄)₂ wherein n is 1 to 5 and R₄ is lower alkyl;

R₂ is hydrogen or R₃; or R₁ and R₂ comprise a ring represented by the following structural formulas:

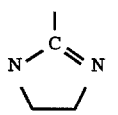

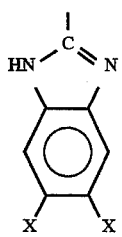

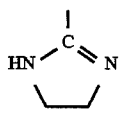

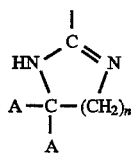

wherein n is 1 to 7; A is hydrogen, alkyl of 1 to 6 carbon atoms or cycloalkyl; and X is halo or A; or (b)

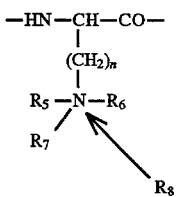

wherein R₅ is alkyl of 1 to 6 carbon atoms, benzyl, phenylethyl, cyclohexyl or cyclopentyl; R₆, R₇ and R₈ are hydrogen or alkyl of 1 to 4 carbon atoms; and n is the integer 2–5; or (c) a substituent of the formula

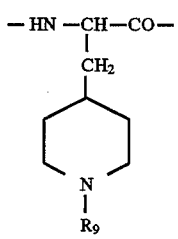

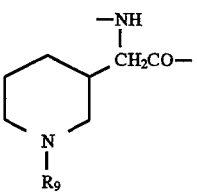

wherein R₉ is hydrogen, alkyl of 1 to 12 carbon atoms, phenyl or phenylloweralkyl;

D is leucyl, isoleucyl, nor-leucyl, N-methyl-leucyl or tryptophanyl;

E is arginyl or leucyl; and

F is glycinamide or —NH—R¹, wherein

R¹ is lower alkyl, cycloalkyl, fluoro lower alkyl or —NH—CO—NH—R² wherein R² is hydrogen or lower alkyl. To adapt the Nestor et al. analogs to molecular packaging, the N-terminal pyroGlu can be replaced with glutamine and the C-terminal Pro-F with Pro-OH.

Exemplary antagonist analogs of LH-RH are provided by Rivier et al. U.S. Pat. No. 4,565,804, dated Jan. 21, 1986 and Rivier et al. U.S. Pat. No. 4,569,927, dated Feb. 11, 1986, both incorporated by reference herein in their entirety and relied upon. The '804 peptides have the structure [SEQ. ID NO. 24]

X—R₁—(W)D—Phe—R₃—R₄—R₅—R₆(V)—R₇—Arg—Pro—R₁₀ wherein X is hydrogen or an acyl group having 7 or less carbon atoms; R₁ is dehydro-Pro, Pro, D-pGlu, D-Phe, D-Trp or β-D-NAL; W is F, Cl, Cl₂Br, NO₂ or C$^α$MeCl; R₃ is D-Trp, (N$^m$For)D-Trp or D-Trp which is substituted in the 5- or 6-position with NO₂, NH₂, OCH₃, F, Cl, Br or CH₃; R₄ is Ser, Orn, AAL or aBu; R₅ is Tyr, (3F)Phe, (2F)Phe, (3I)Tyr, (3CH₃)Phe, (2CH₃)Phe, (2CH₃)Phe, (3Cl)Phe or (2Cl)Phe; R₆ is D-Lys, D-Orn or D-Dap; V is arg-R', R")$_n$(X), with n being 1 to 5 and R' and R" being H, methyl, ethyl, propyl or butyl; R₇ is Leu, NML, Nle or Nva; and R₁₀ is Gly—NH₂, D—Ala—NH₂ or NH-Y, with Y being lower alkyl, cycloalkyl, fluoro lower alkyl or

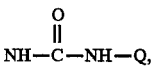

where Q is H or lower alkyl. To adapt the '804 peptides to molecular "packaging" herein, those compounds in which X at the N-terminus is hydrogen will be selected and then the C-terminal R₁₀ group in those compounds will be modified to Gly—OH or D—Ala—OH.

In the '804 peptides, the expression "β-D-NAL" means the D-isomer of alanine, substituted by naphthyl on the β-carbon, or 3-D-NAL. Preferably, the β-carbon is attached at the 2-position of naphthalene (β-D-2NAL), but β-D-1NAL may also be used. "(C$^α$Me-4Cl)Phe" means phenylalanine substituted at the para position with chloro, the α-carbon being methylated. "Dap" means α,β-diaminopropionic acid, or β-aminoalanine. "NML" means $N^\alpha CH_3$-L-Leu. "AAL" means β-amino-Ala or Dap, and "aBu" means α,γ-diaminobutyric acid, either of which or Orn may be present in the 4-position. DehydroPro is preferably at position 1 when Ser is not present at position 4. "$R_6$(arg-R',R")$_n$(X)" means the D-amino acid in the main chain, which through its side chain amino function also forms pan of the arginine-containing peptide side chain.

The '927 peptides have the structure [SEQ. ID NO. 25]

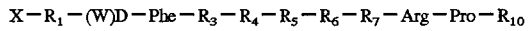

wherein X is hydrogen or an acyl group having 7 or less carbon atoms; $R_1$ is dehydro-Pro, D-pGlu, D-Phe, D-Trp or β-D-NAL; W is F, Cl, $Cl_2Br$, $NO_2$ or $^\alpha MeCl$; $R_3$ is ($N^{in}$For) D-Trp or D-Trp which is substituted in the 5- or 6-position with $NO_2$, $NH_2$, $OCH_3$, F, Cl, Br or $CH_3$; $R_4$ is Ser, Orn, AAL or aBu; $R_5$ is Tyr, Arg, (3F)Phe, (2F)Phe, (3I)Tyr, (3CH$_3$)Phe, (2CH$_3$)Phe, (3Cl)Phe or (2Cl)Phe; $R_6$ is A(4NH$_2$)D-Phe, D-Lys, D-Orn, D-Har, D-His, (4gua)D-Phe, D-Tyr, a D-isomer of lipophilic amino or D-arg; $R_7$ is Leu, NML, Nle or Nva; and $R_{10}$ is Gly-NH$_2$, D-Ala-NH$_2$ or NH-Y, with Y being lower alkyl, cycloalkyl, fluoro lower alkyl or

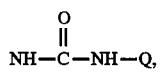

where Q is H or lower alkyl, provided however that when $R_5$ is Arg, $R_6$ is D-Tyr. The various terms are as defined with the '804 peptides. To adapt the '927 peptides to molecular "packaging" herein, the compounds will be selected wherein X is hydrogen and the $R_{10}$ group in those compounds will be modified to glycine or D-alanine.

It is clear from the Nestor et al. and Rivier et at. patents that the amino acid in the 6-position of the LH-RH peptide chain is very amenable to replacement by numerous D-amino acids, including unnatural amino acids which have sizeable side chains. These patents aim confirm the extent of other permissible structural changes discussed hereinabove for LH-RH analogs, e.g., at the 3-, 5- and 7-positions. Any such analogs which can be molecularly "packaged", or which can be structurally modified so that they can be molecularly "packaged", are intended for use herein.

In general, the peptides provided by the present invention are prepared by sequential addition of one or more amino acids or protected amino acids, with the redox system being either first added to an amino acid which is then added to the growing spacer-peptide chain, or else added directly to the spacer-peptide after that portion has been completed. Methods for sequential addition of amino acids to form peptides, utilizing protecting groups where appropriate, are well-known in the art. An excellent summary of such methods, including both solid phase synthesis and synthesis in solution, in contained in Nestor et al. U.S. Pat. No. 4,530,920, which is incorporated in reference herein in its entirety and relied upon. See also SOLID PHASE PEPTIDE SYNTHESIS, second edition, John Morrow Stewart and Janis Dillaha Young, Pierce Chemical Company, Rockford, Ill., 1984.

Peptides provided by the present invention can also be prepared by segment condensation methods described in the literature, e.g., in the Bodanszky and Houben-Weyl references cited above.

The redox portion of the compounds of formulas (I) and (II) is typically introduced after the remainder of the molecule is complete or nearly complete. When the reminder of the molecule is complete, it can be represented by the formula

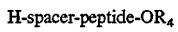 (III)

wherein the structural variables are as defined hereinabove. To afford the compounds in which Z is a direct bond and is attached to a ring carbon atom, that intermediate is typically reacted with an acid of the formula

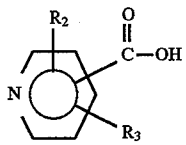 (IV)

wherein $R_2$ and $R_3$ are as defined hereinabove, or the corresponding acid chloride or anhydride. The resultant intermediate of the formula

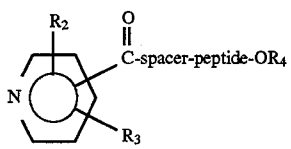 (V)

wherein the structural variables are defined as before is then quaternized with a reactant of the formula

 (VI)

wherein X is an anion of a non-toxic pharmaceutically acceptable acid and $R_1$ is $C_1$-$C_7$ alkyl, $C_1$-$C_7$ haloalkyl or $C_7$-$C_{12}$ aralkyl, to afford the desired quaternary salt of formula (II). Variations of this method are described in the EXAMPLES hereinafter.

Alternatively, to prepare the compounds in which Z is $C_1$-$C_6$ alkylene attached to a ring nitrogen atom and $R_1$ is a direct bond, the peptide intermediate

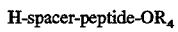 (III)

is reacted with a compound of the formula

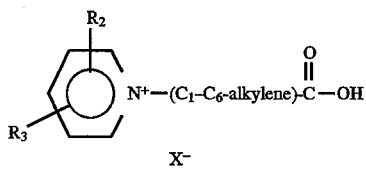 (VII)

wherein the structural variables are defined as before, to afford the corresponding quaternary salt of formula (II).

The various starting materials (IV), (VI) and (VII) employed in the processes described above are commercially available or can be prepared by known methods. The processes described above can be appropriately modified to afford other compounds of the invention, as will be apparent to those of ordinary skill in the art.

When an anion is desired which is different from the one obtained by one of the processes described above, the anion in the quaternary salt of formula (II) may be subjected to anion exchange via an anion exchange resin or, more conveniently, by use of the method of Kaminski et al., Tetrahedron, Vol. 34, pp. 2857-2859 (1978). According to the Kaminski et al. method, a methanolic solution of an HX acid will react with a quaternary ammonium halide to produce the methyl halide and the quaternary .X salt.

The quaternary salts of formula (II) can be reduced to form the corresponding dihydro derivatives of formula (I).

Reduction of the quaternary salts of formula (II) to the corresponding dihydro derivatives of formula (I) is usually conducted at a temperature from about −10° C. to room temperature, for a period of time from about 10 minutes to 3 hours, conveniently at atmospheric pressure. The process is conducted in the presence of a suitable reducing agent, preferably an alkali metal dithionite such as sodium dithionite, an alkali metal borohydride such as sodium borohydride or lithium aluminum borohydride, or a more reactive dihydropyridine such as 1-benzyl-1,2-dihydroisonicotinamide.

Sodium dithionite reduction is conveniently carried out in an aqueous solution, e.g., aqueous methylene chloride, in the presence of base, e.g., sodium bicarbonate, and, in the case of pyridinium and quinolinium starting materials, generally affords a preponderance of 1,4-dihydro isomer. The dihydro product is usually insoluble in water and thus can be readily separated from the sodium dithionite reaction medium.

In the case of sodium borohydride reduction, an organic reaction medium is typically employed, e.g., a lower alkanol such as methanol, an aqueous alkanol or other protic solvent. For pyridinium and quinolinium starting materials, sodium borohydride reduction typically affords a preponderance of the 1,6-dihydropyridine and 1,2-dihydroquinoline isomers, respectively.

Other useful reducing agents include dihydropyridines which are more reactive than the quaternary salts which are to be reduced. A particularly suitable reagent of this type is the highly reactive 1-benzyl-1,2-dihydroisonicotinamide, which can be used for selective reduction of the quaternary salts by a direct hydride transfer reaction under neutral conditions [Nuvole et at., *J. Chem. Research*, 1984, (S), 356]. Thus, for example, pyridinium and quinolinium salts of the invention can be regioselectively reduced to the corresponding 1,4-dihydropyridines and 1,4-dihydroquinolines, respectively, utilizing 1-benzyl-1,2-dihydroisonicotinamide as the reducing agent, typically in a suitable organic reaction medium, e.g., anhydrous methanol. Other possible reducing agents of the reactive dihydropyridine type include ribosyl N-methyl dihydronicotinamide (derived from NADH).

The methods for synthesizing the amino acids and peptides of the present invention have already been discussed hereinabove, and are shown in detail in the EXAMPLES which follow. In some cases, the methods of peptide synthesis can be simplified by utilizing commercially available bioactive peptides and their fragments. SIGMA® CHEMICAL COMPANY, Post Office Box 14508, St. Louis, Mo. 63178 US has a large number of such products available; some of those which may be useful in preparing the instant redox peptides include, for example angiotensin II, neurotensin fragment 1-6, neurotensin fragment 1-8, neurotensin fragment 8-13, Substance P fragment 1-4, Substance P fragment 4-11, Substance P fragment 5-11 and Substance P fragment 7-11.

In a specific embodiment of the present invention, molecular "packaging" has been used for two enkephalin analogs, [D-Ala$^2$]-Leu-enkephalin and [D-Ala$^2$]-[D-Leu$^5$]-enkephalin, in order to circumvent both the physical blood-brain barrier and the enzymatic blood-brain barrier and deliver the peptide by sequential metabolism. The Scheme below illustrates a preferred embodiment of the system where YAGLF represents [D-Ala$^2$]-[D-Leu$^5$]-enkephalin, i.e., [SEQ. ID NO. 26] Tyr-D-Ala-Gly-Phe-D-Leu, or [D-Ala$^2$]-Leu-enkephalin, i.e., [SEQ. ID NO. 27] Tyr-D-Ala-Gly-Phe-Leu. In the case of compound (B), it is of course the quaternary cation, not necessarily the particular salt thereof shown in the EXAMPLES, which is found in vivo; the anion may be any anion present in vivo.

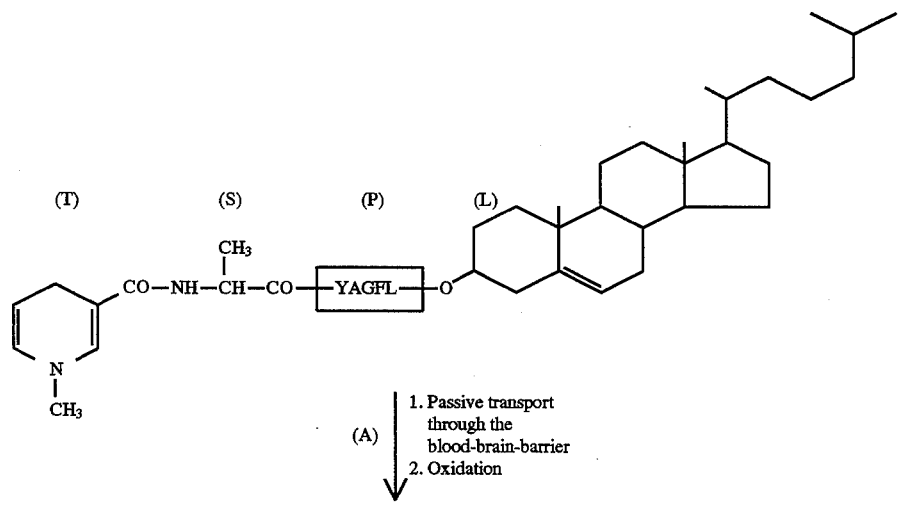

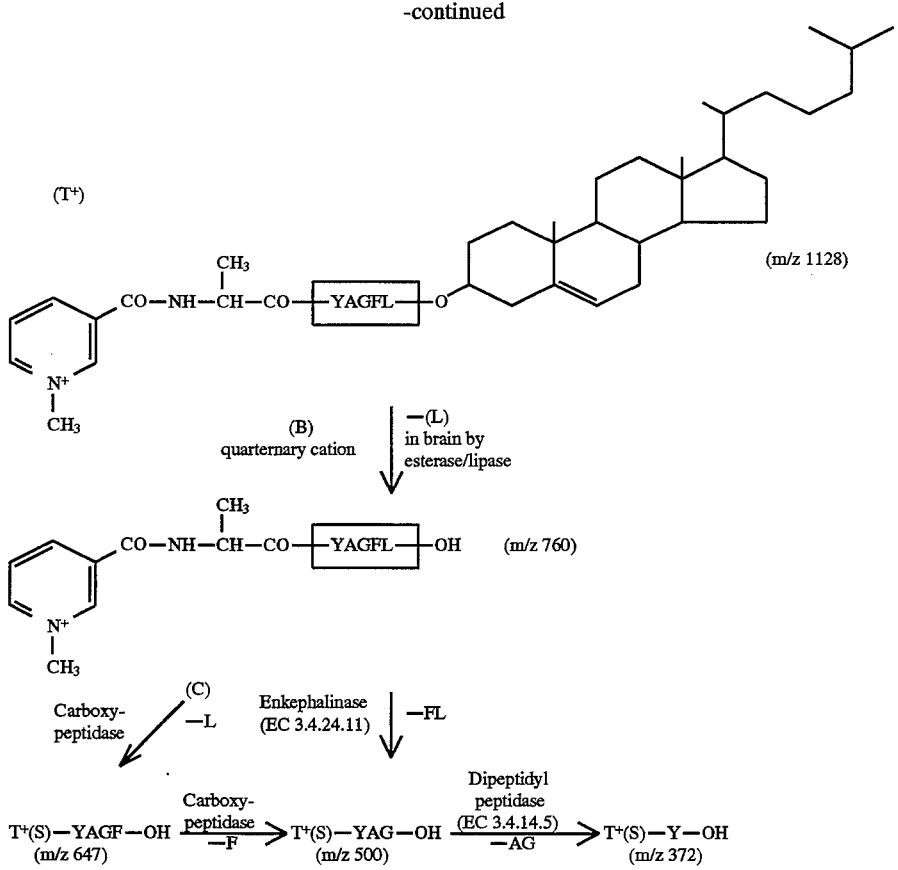

As is apparent from the Scheme above, both the COOH-terminus and the $NH_2$-terminus of the molecule have been modified in such a way as to increase the lipid solubility of the peptide, and also to prevent cleavage by the BBB aminopeptidases. Additionally, the representative 1,4-dihydrotrigonellinate redox targetor (T) exploits the unique architecture of the BBB which allows for the influx of the lipid soluble neutral form, but is not permeable to the positively charged form. The redox targetor has proved to be widely applicable for brain-targeting of a variety of substances as noted hereinabove, and its attachment alone results in brain-specific delivery for small molecules.

The enkephalins are sensitive to cleavage by endopeptidases at the $Gly^3$-$Phe^4$ peptide bond. Cholesteryl, a bulky and lipophilic steroidal moiety (L), provides a representative ester function that increases the lipid solubility and also hinders the C-terminal portion of the peptide from being recognized by peptide-degrading enzymes. This part of the molecule is, however, labile toward esterase or lipase, which permits its removal after delivery. The lipases or esterases expose the peptide unit that can interact with specific receptors, or that may serve as a substrate for various neuropeptide processing and degrading enzymes. A spacer function (S) is also incorporated in order to preserve the integrity of the peptide unit by spatially separating the important segment of the molecule [SEQ. ID NO. 28] (YAGFL) from the targetor (T). This spacer may be another amino acid residue or residues as defined hereinabove. The selection of an L-alanyl spacer is justified based on the suggested involvement of alanyl aminopeptidase in the enkephalinergic transmission in the CNS. In essence, the peptide unit in this delivery system appears as a perturbation on the bulky molecule dominated by the lipophilic steroidal portion and the targetor, which also prevents recognition by the peptidases.

This approach has been evaluated by using electrospray ionization mass spectrometry, which provides the specificity necessary to monitor the biotransformation processes that occur after delivery. In vivo distribution studies with rats as experimental models (described in detail below) have shown that, upon systemic administration, the modified peptide can partition by passive, nonsaturable transport into the brain which is inaccessible to the unmanipulated compound. At this first step, the modified peptide simply enters the brain because of its lipoidal nature. The targetor moiety, however, undergoes an enzyme-mediated oxidation analogous to the endogenous $NAD(P)H \rightleftharpoons NAD(P)^+$ coenzyme associated with numerous oxidoreductases and cellular respiration. This redox reaction converts the dihydrotrigonellinate to the hydrophilic, membrane-impermeable trigonellinate ion; thus, it remains trapped behind the BBB, as shown by the presence of m/z 1128, compound (B), cation, in the electrospray ionization mass spectrum of the brain extract. Oxidation of compound (A) in the periphery, on the other hand, results in its rapid secretion from the body, since the pyridinium salt, compound (B), is easily eliminated by the kidney and bile. Consequently, no detectable amount of the trigonellinates was found in the blood samples collected 5 to 10 minutes after systemic administration.

The removal of the cholesteryl group (L) by esterase or lipase occurs subsequent to or simultaneously with the brain-targeting enzymatic oxidation. The targetor-peptide conjugate, compound (C), occurs at 500 to 700 pmole per gram brain tissue 15 minutes after the intravenous administration of the modified peptide. However, a half-life of about 40 to 60 minutes was observed for the conjugate of [$D$-$Ala^2$]-Leu-enkephalin, which indicates its processing or degradation by peptidases. The fate of the targetor-peptide conjugate compound (C) has been investigated with an appropriate in vitro experiment described below. As with the [D-Ala$^2$]-Leu-enkephalin analog, the neutral endopeptidase or enkephalinase is most probably the major degrading enzyme for the peptide conjugate, and the action of other peptidases (carboxypeptidase, dipeptidyl peptidase) can also be reasonably assigned. The conjugate of the [D-Ala$^2$]-[D-Leu$^5$]-enkephalin exhibits increased resistance to the carboxypeptidases and to the enkephalinase.

Figure 3:
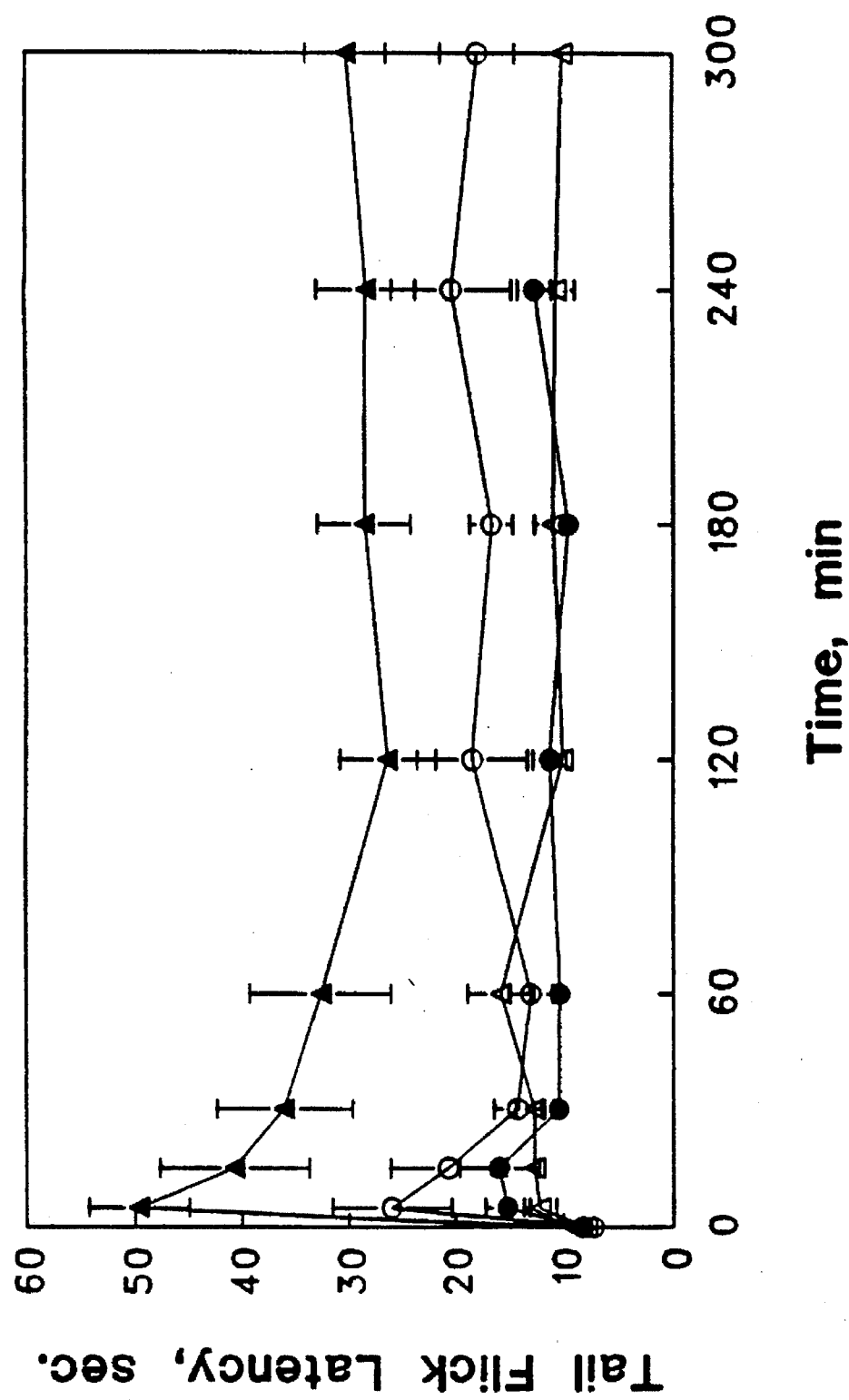
FIG. 3 is a graph plotting the tail flick latency in rats in seconds, against time in minutes, following intravenous administration of a representative "packaged" enkephalin-type peptide of the invention, at 5 mg/kg (o) and at 10 mg/kg (▲), the corresponding "unpackaged" enkephalin analog at 5 mg/kg (Δ) [equimolar to the 10 mg/kg dose of the "packaged" peptide] and the vehicle control (●)
Figure 4:
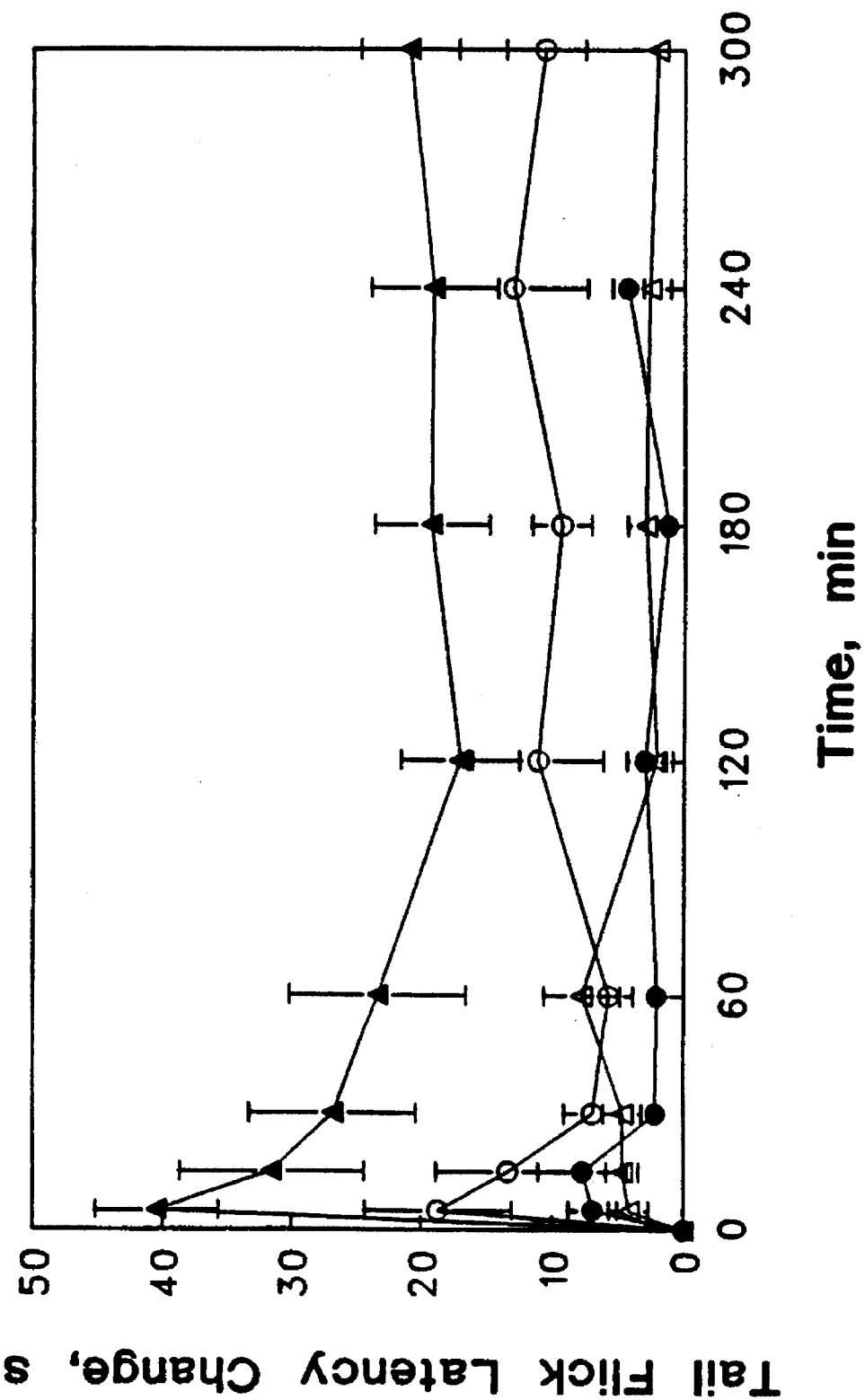
FIG. 4 is a graph plotting the tail flick latency change in rats in seconds, against time in minutes, for the same pharmacological test as in FIG. 3, the symbols having the same meaning as given for FIG. 3 above.
Figure 5:
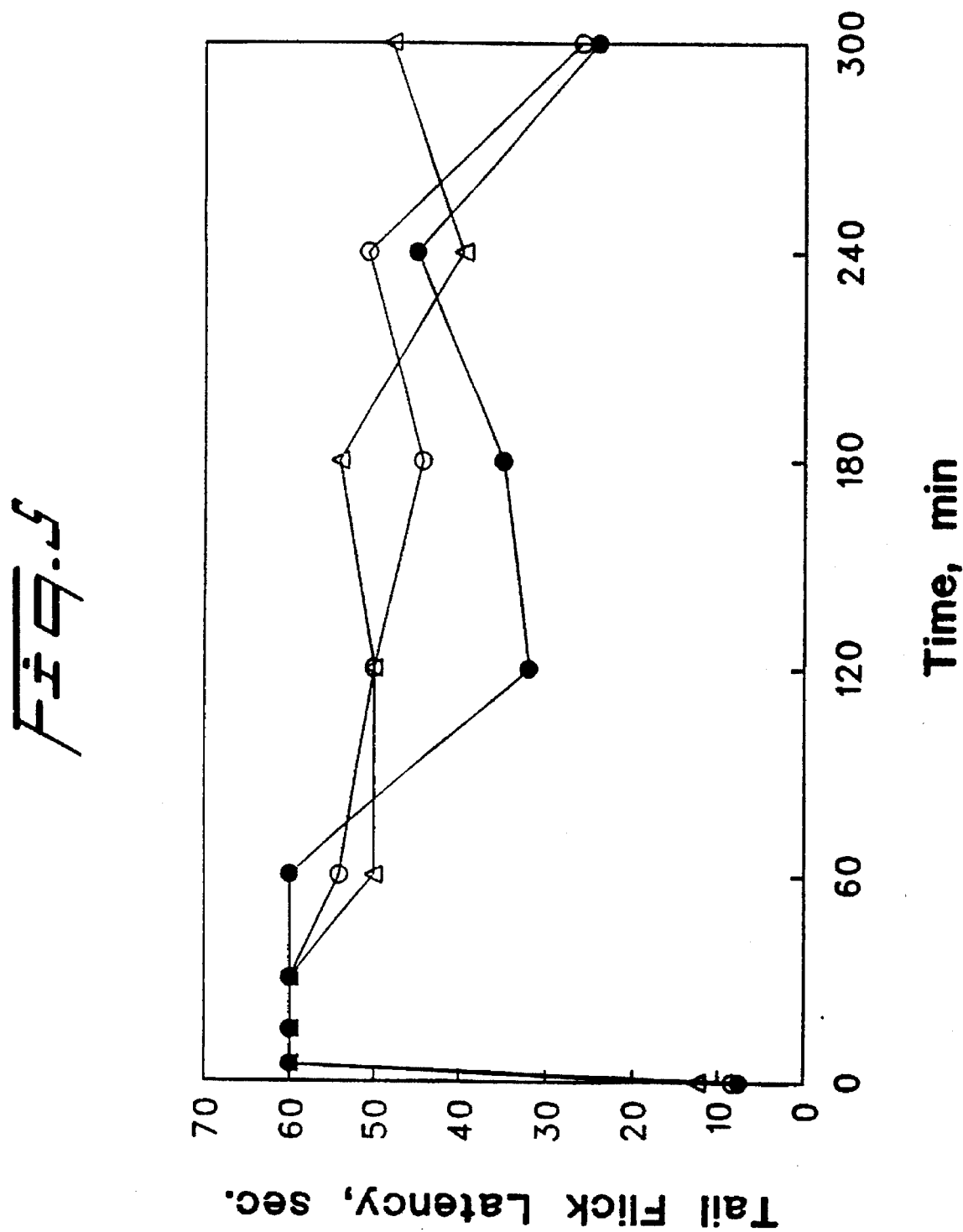
FIG. 5 is a graph plotting the tail flick latency in rats in seconds, against time in minutes, following intravenous administration of 10 mg/kg of the representative "packaged" enkephalin in three representative rats (●, o and Δ) of the group of ten rats tested, showing consistent response for a prolonged period of time.

A significant and prolonged increase in the latency of the tail-flick response, a measure of the central analgesic activity, of the experimental animals after the intravenous injection of the modified peptide (A) has been observed. The test procedure is described hereinbelow following the EXAMPLES, and the results are shown in Tables 5–8 and FIGS. 3–5 for (A) where [SEQ. ID NO. 27] YAGFL is [D-Ala$^2$]-[D-Leu]-enkephalin; i.e., Compound (64) in the EXAMPLES. The targetor-peptide conjugates (C), such as compound (70), are weak opioids. The 50 percent inhibitory concentration (IC$_{50}$) measured with [$^3$H]diprenorphine-based competitive assay is about 10$^{-7}$M, an order of magnitude less than the IC$_{50}$ of about 10$^{-8}$M for the enkephalin analogs. At the measured 500 to 700 pmol/g tissue concentration, even these weak opioids exert significant analgesic activity. The enkephalin analog may also be released slowly from the targetor-peptide conjugate in vivo, and contribute to the CNS activity. No analgesia was observed after the intravenous administration of the unmanipulated enkephalins, which are membrane-impermeable and unprotected toward various peptide-degrading enzymes, nor after the injection of the partially conjugated (either with the targetor or with cholesteryl) peptides. Modification of the spacer (S) function may allow for the peptidolytic release of the parent peptide from the conjugate at a desired rate, depending on the therapeutic objective.

Thus, in the Scheme for brain delivery of peptides by sequential metabolism depicted above, the "packaged" molecule, compound (A), with its peptide nature disguised, enters the CNS by passive transport without proteolytic degradation due to its high lipophilicity. The targetor (T) function is converted by enzymatic oxidation (NAD+ →NADH coenzyme) to the compound (B) cation possessing a membrane impermeable ionic group (T$^+$). The biolabile lipophilic protection is cleaved by esterase or lipase, and the relatively stable, locked-in targetor-peptide conjugate, compound (C), may interact with specific receptors and be processed by peptidases. The protected molecules in the Scheme were obtained by a solution-phase, sequential deprotection-coupling procedure (t-butoxycarbonyl chemistry) starting with the leucine cholesterate, and finally coupling (DCC) with nicotinic acid. Compound (B) was prepared by the subsequent quaternization with dimethyl sulfate, and its reduction with sodium dithionite yielded compound (A). As an analytic standard and the subject of in vitro evaluation, compound (C) was obtained by solid-phase peptide synthesis. The resin-bound peptide [SEQ. ID NO. 29] (AYAGFL) was coupled with nicotinic acid, then quaternized (dimethyl sulfate), cleaved from the support by hydrogen fluoride, and finally purified by preparative reversed-phase liquid chromatography. The compounds prepared have been fully characterized by chromatography and mass spectrometry (fast atom bombardment and electrospray ionization). For further synthetic details, see the EXAMPLES hereinafter.

Detection of the peptide conjugates in the brain tissue by electrospray ionization mass spectrometry was carried out after systemic administration of compound (A). Sprague-Dawley rats weighing 200 to 300 g were used as experimental models. The delivery system, compound (A), dissolved in a vehicle consisting of ethanol and 50% w/w hydroxypropyl-β-cyclodextrin (1:1) vehicle was injected intravenously through the tail vein at a 20 mg/kg dose. After killing the animals by decapitation, the brain tissue was collected and homogenized in cold 1M acetic acid. After centrifuging for 15 minutes at 12,500 g, the supernatant was removed and passed through Supelclean LC-18 cartridges. The poorly retained compounds were eluted with 3% (v/v) acetic acid, and the sample was collected by eluting with 70% methanol plus 30% water containing 3% (v/v) acetic acid. The solvent was removed under a dry nitrogen stream, and the reconstituted (in 50% methanol plus 50% water containing 3% acetic acid) sample was analyzed by electrospray ionization mass spectrometry at 5 μl/minute flow rate. In the sample collected 15 minutes after intravenous administration of compound (A) for [D-Ala$^2$]-Leu-enkephalin, compound (B) cation (mass-to-charge ratio, m/z, 1128) can be detected and compound (C) (m/z 760) is present in an estimated 500–700 picomole/g tissue level. Quantification was based on comparing the peak intensity to that obtained from the brain sample of an untreated animal spiked with a known amount of compound (C). In tissue collected 1, 2 and 4 hours after systemic administration, compound (B) cation can no longer be identified, and the quantity of compound (C) is proportionally (with approximately 40 to 60 minute half-life) decreased with time.

The targetor-peptide conjugate compound (C) is processed by the brain peptidases similarly to the unmanipulated compound, [D-Ala$^2$]-Leu-enkephalin. Compound (C) (30 nmol) was added to one ml rat brain homogenate (20%, w/w, in pH 7.4 Tris buffer), and the mixture was incubated at 37° C. Aliquots (250 t l) were removed 0.5 and 2 hours after incubation, and electrospray ionization mass spectra were obtained after sample preparation identical to that described above. Proteolytic cleavages are identified by the m/z of the products, and the corresponding structures are shown in the Scheme.

It is clear from the foregoing and the in vivo data presented hereinbelow, that this method, which is based on a chemical delivery system, has been shown useful for the brain delivery of peptides. By overcoming the obstacles represented by the physical and enzymatic blood-brain barriers, the promise of biologically active peptides to become a future generation of high-efficiency neuropharmaceuticals may be realize.

Further illustrations of the general applicability of the molecular "packaging" approach of the present invention are given below.

Reaction Schemes I through V below show schematically the syntheses of representative peptides of the invention and intermediates thereto. These and related compounds are described in EXAMPLES 1–24 hereinafter. The peptide final products are chemical delivery systems for the brain-enhanced delivery of the Thyrotropin-Releasing Hormone (TRH) analog, PyroGlu-Leu-ProNH$_2$. PyroGlu-Leu-ProNH$_2$ is a Thyrotropin-releasing Hormone (TRH, Pyroglu-His-ProNH$_2$) analog with elevated CNS activity and decreased hormonal potency which is considered to be advantageously applicable in the treatment of mental depression. However, this peptide does not enter the central nervous system (CNS) due to its hydrophilic character and because of the presence of the peptidolytic enzymes in the lipoidal blood-brain barrier (BBB).

A novel strategy has been developed in accord with the present invention to achieve brain-delivery of a peptide conjugate. A TRH analog, Gln-Leu-Pro-Gly, was placed in a molecular environment that disguises its peptide nature and provides biolabile, lipophilic functions to penetrate the blood-brain barrier by passive transport. The design also incorporates a 1,4-dihydrotrigonellinate targetor that undergoes an enzymatically-mediated oxidation to a hydrophilic, membrane impermeable trigonellinate salt. The post-delivery enzymatic reactions (through cholesterol hydrolases and esterases) provide a polar targetor-peptide conjugate that is trapped behind the lipoidal BBB and deposited in the CNS. The conjugate is a substrate for numerous peptide processing/degrading enzymes including dipeptidyl dipeptidase, postproline cleavage enzyme, carboxypeptidase P, pyroglutamyl peptidase, glutamine-peptide cyclase and the glycine-directed amidase. Through sequential enzymatic processing/degrading, the final target peptide, PyroGlu-Leu-ProNH$_2$, should be released in pharmacologically significant amount in the brain.

In Schemes I through V and EXAMPLES 1–24 which follow, abbreviations generally follow IUPAC-IUB recommendations as published in *J. Biol. Chem.* 264, 668–673 (1989). Other abbreviations include: AA, amino acid; Boc, t-butyloxycarboxyl; DCC, 1,3-dicyclohexylcarbodiimide; DCU, 1,3-dicyclohexylurea; DIEA, N,N-diisopropylethylamine; DMAP, 4-dimethylaminopyridine; HOBt, 1-hydroxybenzotriazole; TFA, trifluoroacetic acid; cholesteryl ester, the ester of the 3-hydroxy group of cholesterol with the carboxylic acid function of the C-terminal amino acid. All amino acids in this group of reaction schemes/EXAMPLES are L-configuration. Abbreviations follow the recommendations of the IUPAC-IUB Commission on Biological Nomenclature as given in *Eur. J. Biochem.* 138, 9–37 (1964).

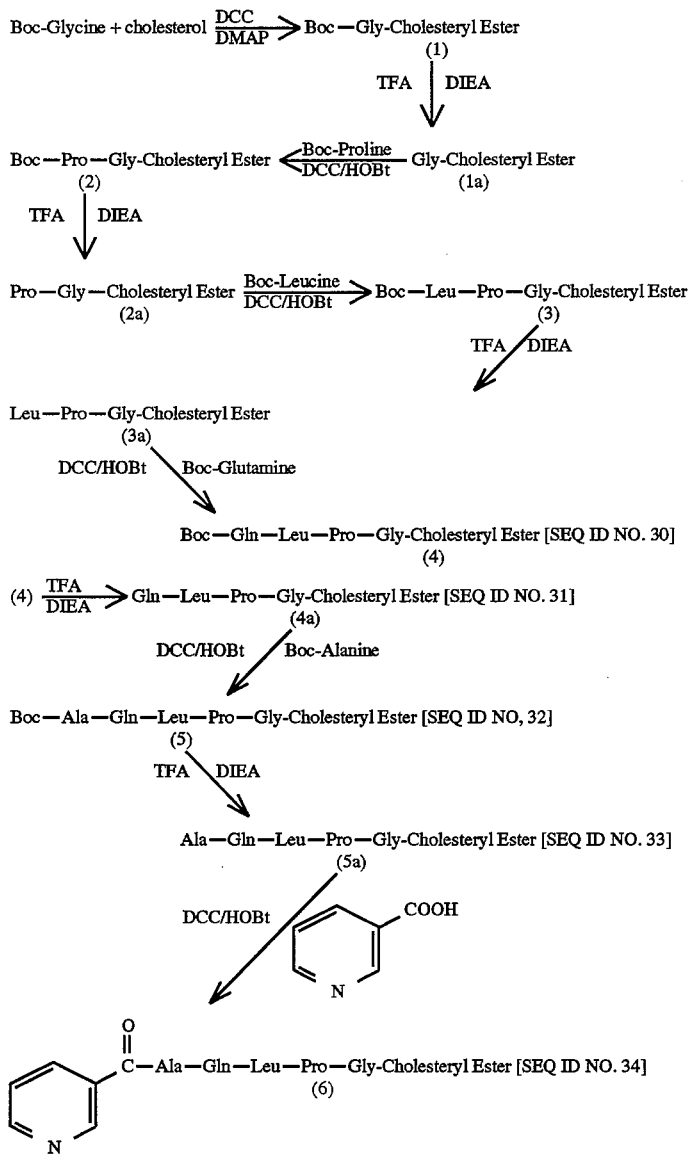

-continued
Scheme I
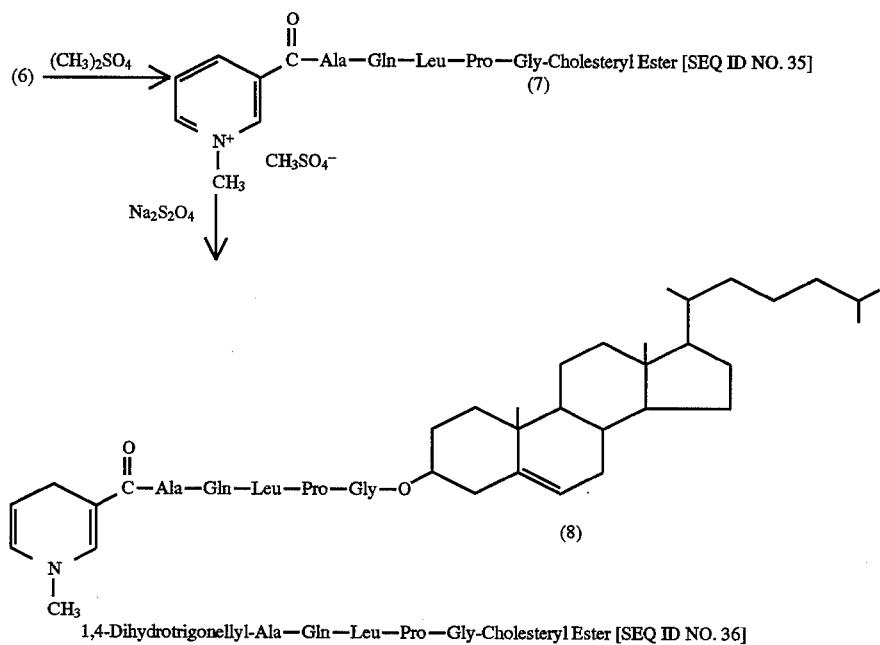
1,4-Dihydrotrigonellyl-Ala—Gln—Leu—Pro—Gly-Cholesteryl Ester [SEQ ID NO. 36]
Scheme II
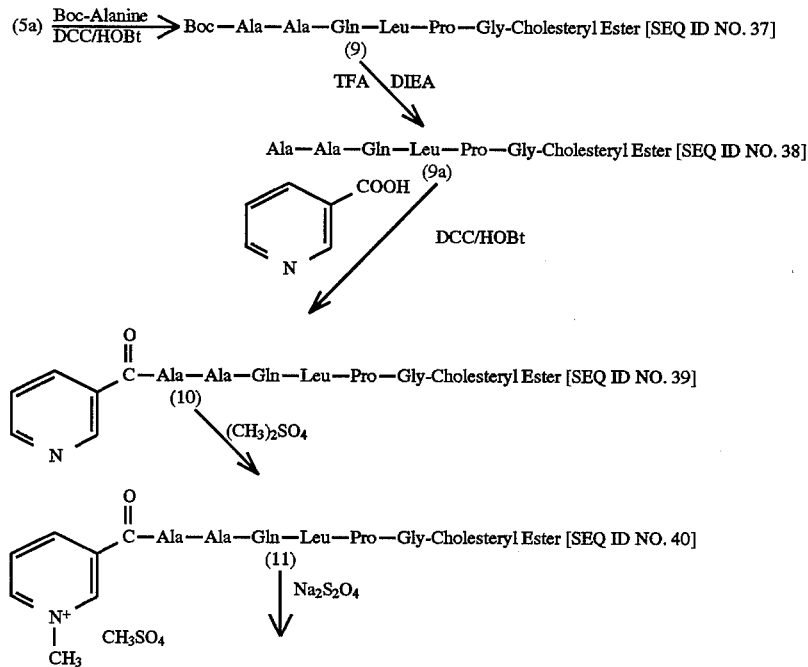

-continued
Scheme II

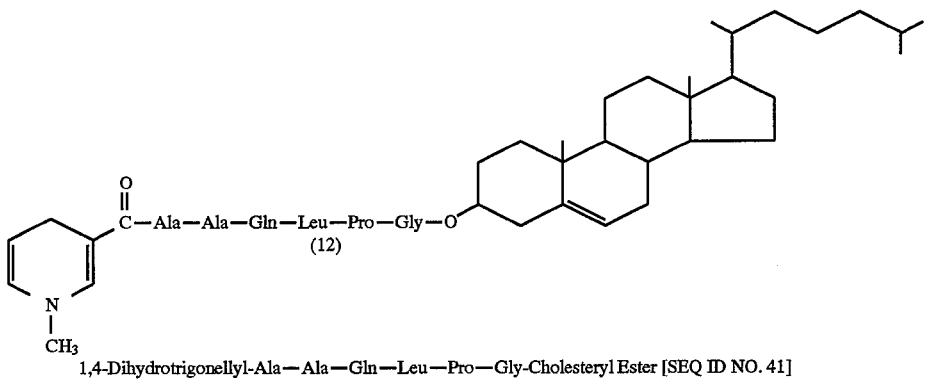

1,4-Dihydrotrigonellyl-Ala—Ala—Gln—Leu—Pro—Gly-Cholesteryl Ester [SEQ ID NO. 41]

This reaction scheme can be readily modified by substituting Boc-Proline for the Boc-Alanine utilized in the first step. This results in a series of compounds like (9), (9a), (10), (11) and (12) above, except that the "Ala-Ala" spacer is replaced with a "Pro-Ala" spacer. The final product is 1,4-dihydrotrigoneilyl-Pro-Ala-Gln-Leu-Pro-Gly-cholesteryl ester [SEQ. ID NO. 42].

Scheme III

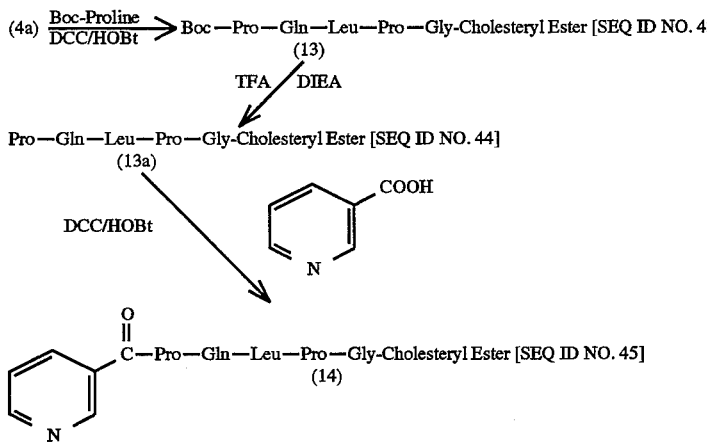

Scheme IV

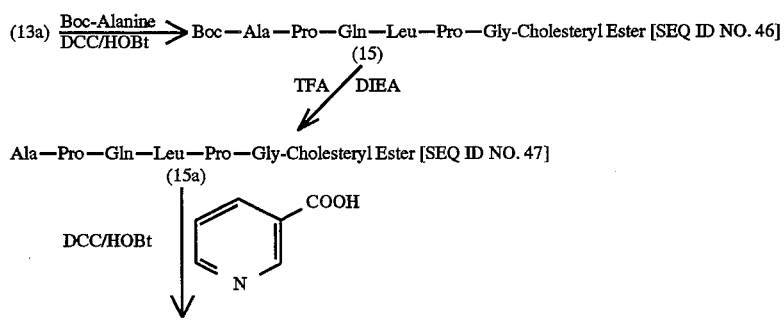

-continued
Scheme IV

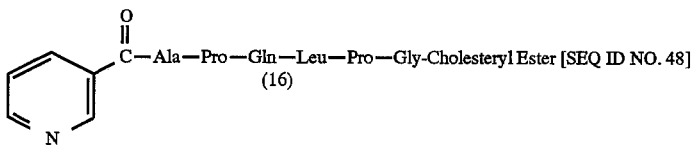

Scheme V

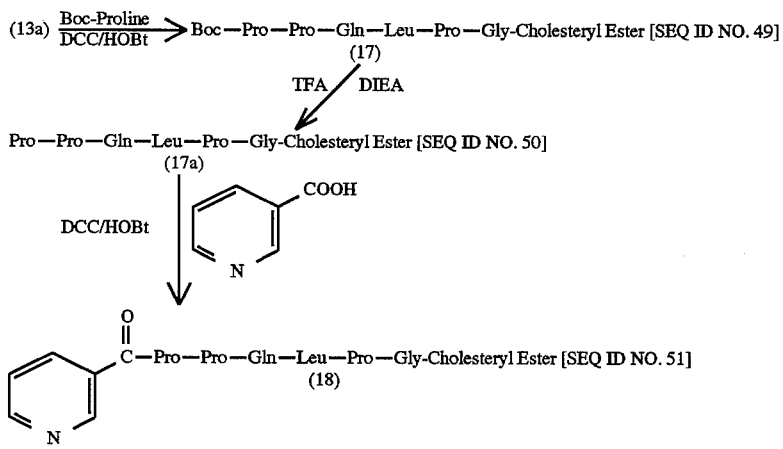

As depicted in Schemes I through V, to prepare the Boc-glycine cholesteryl ester (1), Boc-Glycine was esterified with the 3-hydroxyl group of cholesterol (Cholest-5-en-3-ol) with dicyclohexylcarbodiimide (DCC) as alehydrating agent and dimethylaminopyridine (DMAP) as a catalyst, the Boc protecting group of (1) was removed with TFA/methylene chloride (50:50) and the obtained glycine cholesteryl ester trifluoroacetate was neutralized with N,N-diisopropylethylamine (DIEA) to give (1aa). The N-Boc protected dipeptidyl cholesteryl ester (2) was prepared by directly coupling (1a) with Boc-Proline using the DCC/HOBt method. This strategy was used to synthesize the different peptide cholesteryl ester intermediates (5), (9), (13), (15), (17) in a stepwise fashion in solution. After deprotection with TFA, all the above intermediates were coupled to nicotinic acid separately to get the different nicotinoyl peptide cholesteryl esters (6), (10), (14), (16), (18). The N-alkylations of (6), (10) in order to obtain the respective quaternary salts (7), (11) were performed with dimethylsulfate in methylene chloride with a few drops of methanol present, and the reductions to the corresponding 1,4-dihydropyridine derivatives (8), (12) were performed by using sodium dithionite as reducing agent in a mixture of methanol and aqueous sodium bicarbonate.

In all cases before the N-alkylation step, the intermediates were purified by chromatography. In order to avoid side reactions, the N-methylations were performed at room temperature (20°–25° C.) with a slight excess of alkylating agent. The reductions with sodium dithionite were accomplished by cooling at 0°–5° C. in oxygen-free conditions at a pH of approximately 7. The quaternary salts are fairly stable when isolated, but the dihydropyridine derivatives are easily oxidized or hydroxylated and in acid conditions react readily with water. The dihydropyridine derivatives (8), (12) were proved to be the 1,4-isomers by their typical UV maxima at approximately 360 nm, as opposed to the corresponding quaternary salts (7), (11) which show UV maxima at approximately 260 nm.

The reactions summarized above are described in more detail in the EXAMPLES which follow, which are for the purpose of illustration and are in no way limitative of the invention. In these EXAMPLES, all chemicals used were reagent grade. All solvents were from Fisher Scientific. Proton NMR measurements were made on a Varian T-90 NMR spectrometer with $CDCl_3$ as solvent and tetramethylsilane (TMS) as the internal calibrant. Melting points were taken on a Fisher-Johns melting point apparatus and are uncorrected. Electrospray Ionization Mass Spectras were made on a Kratos MFC500Mass spectrometer. Thin layer chromatography (TLC) determinations were carried out on silica gel coated plastic or foil EM Science DC-plates coated to a thickness of 0.2 mm with silica gel 60 containing Florescent (254) indicator. Elemental analyses of compounds synthesized were performed by Atlantic Microlab, Inc., Atlanta, Ga.

Cholesterol was purchased from the Sigma Chemical Co., St. Louis, Mo. All of the blocked amino acids were purchased from Bachera (US), Torrance, Calif., and Sigma Chemical Co., St. Louis, Mo.

EXAMPLE 1

Preparation of Boc-Gly-Cholesteryl Ester (1):

Boc-Glycine (10 g, 0.057 mol), cholesterol (14.72 g, 0.038 mol) and DMAP (4.66 g, 0.038 mol) in methylene chloride (200 ml) were stirred at 0° C. for 30 minutes, a solution of DCC (6.21 g, 0.03 mol) in 50 ml of methylene chloride was added and the mixture was allowed to stand at room temperature for 48 hours. The formed dicyclohexylurea (DCU) was filtered off and the filtrate was diluted with methylene chloride, and washed successively with citric acid (5%, 5×100 ml), saturated sodium bicarbonate (5×100 ml), and distilled water (5×100 ml), then dried over sodium sulfate and evaporated to give a solid. Silica gel column chromatography, CHCl$_3$/MeOH (100:1), afforded a white solid. Yield: 14.46 g, 70%. TLC, CHCl$_3$/MeOH (99:1), R$_f$=0.61; m.p. 115°–116° C. $^1$HMR (CDCl$_3$): 5.30 (brm, 1H), 4.40–4.95 (m, 1H), 3.9 (d, 2H), 0.70–2.40 (m, 52H).

EXAMPLE 2

Preparation of Boc-Pro-Gly-Cholesteryl Ester (2):

Boc-Glycine cholesteryl ester (1 ) (14.40 g, 0.026 mol) in methylene chloride (22.5 ml) was stirred with TFA (25 ml) for 60 minutes and the solvents removed in vacuo. Boc-Pro-OH (6.83 g, 0.032 mol) was treated with HOBt (5.62 g, 0.0416 mol) and DCC (9.92 g, 0.048 mol) in DMF (15 ml) and chloroform (30 ml) at 0° C. for 10 minutes and then at room temperature for 60 minutes. The TFA salt prepared above in methylene chloride (50 ml) was added and DIEA was used to adjust the pH to neutrality. After 60 minutes, the reaction mixture was filtered, diluted with methylene chloride, and washed successively with citric acid (5%, 3×100 ml), saturated sodium bicarbonate (3×100 ml), and distilled water (3×100 ml), then dried over sodium sulfate and evaporated to give a solid. Silica gel column chromatography, CHCl$_3$/MeOH (100:1), afforded a white solid (14.48 g, 85.6%). TLC, CHCl$_3$/MeOH (99:1), R$_f$=0.25; NMR (CDCl$_3$): 5.30 (brm, 1H), 4.5–4.9 (brm, 1H), 4.20 (m, 1H), 3.95 (m, 2H), 3.3–3.7 (brm, 2H), 0.7–2.4 (m, 56H).

EXAMPLE 3

Preparation of Boc-Leu-Pro-Gly-Cholesteryl Ester (3):

Boc-Pro-Gly--cholesteryl ester (2) (10 g, 0.0156 mol) was deblocked with TFA as described above. Boc-Leu-OH (4.33 g, 0.0187 mol) was treated with HOBt (3.285 g, 0.024 mol) and DCC (5.8 g, 0.028 mol) in DMF (8 ml) and chloroform (40 ml) at 0° C. for 10 minutes and then at room temperature for 60 minutes. The TFA salt prepared above in methylene chloride (50 ml) was added and DIEA was used to adjust the pH to neutrality. After 60 minutes the reaction mixture was filtered, diluted with methylene chloride, and washed successively with citric acid (5%, 3×80 ml), saturated sodium bicarbonate (3×80 ml), and distilled water (3×80 ml), then dried over sodium sulfate and evaporated to give a solid. Silica gel column chromatography, CHCl$_3$/MeOH (98:2), afforded a white solid (9.71 g, 82.5%). CHCl$_3$/MeOH (90:10), R$_f$=0.65; NMR (CDCl$_3$): 5.30 (m, 1H), 4.90 (m, 1H), 4.5–4.9 (brm, 2H), 4.20 (t, 1H), 3.95 (t, 2H), 3.4–3.8 (brm, 2H), 0.7–2.4 (m, 65H).

EXAMPLE 4

Preparation of [SEQ ID NO. 30] Boc-Gln-Leu-Pro-Gly-Cholesteryl Ester (4):

Boc-Leu-Pro-Gly-cholesteryl ester (3) (9.71 g, 0.0129 mol) was deblocked with TFA as described above. Boc-Gln (3.80 g, 0.0155 mol) was treated with HOBt (2.71 g, 0.020 mol) and DCC (4.79 g, 0.023 mol) in DMF (20 ml) and chloroform (100 ml) at 0° C. for 10 minutes and then at room temperature for 60 minutes. The TFA salt prepared above in methylene chloride (50 ml) was added and DIEA was used to adjust the pH to neutrality. After 150 minutes, the reaction mixture was filtered, diluted with methylene chloride, and washed successively with citric acid (5%, 3×80 ml), saturated sodium bicarbonate (3×80 ml), and distilled water (3×80 ml), then dried over sodium sulfate and evaporated to give a solid. Silica gel column chromatography, CHCl$_3$/ MeOH (92:8), afforded a white solid (4.39 g, 38.64%). CHCl$_3$/MeOH (90:10), R$_f$=0.37; EI (Electrospray Ionization) MASS (m/z, %RA) [after removing Boc with trifluoroacetic acid]: 782, 100.

EXAMPLE 5

Preparation of [SEQ ID NO. 32] Boc-Ala-Gln-Leu-Pro-Gly-Cholesteryl Ester (5):

[SEQ ID NO. 30] Boc-Gln-Leu-Pro-Gly-cholesteryl ester (4) (1 g, 1.134 mmol) was deblocked with TFA as described above. Boc-Ala-OH (0.26 g, 1.36 mmol) was treated with HOBt (0.26 g, 1.95 mmol) and DCC (0.66 g, 3.17 mmol) in methylene chloride (50 ml) at 0° C. for 10 minute g and then at room temperature for 60 minutes. The TFA salt prepared above in methylene chloride (10 ml) was added and DIEA was used to adjust the pH to neutrality. After 60 minutes the reaction mixture was filtered, diluted with methylene chloride, and washed successively with citric acid (5%, 3×80 ml), saturated sodium bicarbonate (3×80 ml), and distilled water (3×80 ml), then dried over sodium sulfate and evaporated to give a solid. Silica gel column chromatography, CHCl$_3$/MeOH (92:8), afforded a white solid (0.98 g, 86.41%). TLC, CHCl$_3$/MeOH (90:10), R$_f$=0.32; EI MASS (m/z, %RA) [after removing Boc with trifluoroacetic acid]: 853,100.

EXAMPLE 6

Preparation Of [SEQ ID NO. 34] Nicotinoyl-Ala-Gln-Leu-Pro-Gly-Cholesteryl Ester (6):

Boc[SEQ ID NO. 32]-Ala-Gln-Leu-Pro-Gly-cholesteryl ester (5) (0.66 g, 0.69 mmol) was deblocked with TFA as described above. Nicotinic Acid (0.10 g, 0.81 mmol) was treated with HOBt (0.16 g, 1.18 mmol) and DCC (0.4 g, 1.94 mmol) in methylene chloride (26 ml) and DMF (3 ml) at 0° C. for 10 minutes and then at room temperature for 60 minutes. The TFA salt prepared above in methylene chloride (10 ml) was added and DIEA was used to adjust the pH to neutrality. After 4 hours the reaction mixture was filtered, diluted with methylene chloride, and washed successively with citric acid (5%, 3×70 ml), saturated sodium bicarbonate (3×70 ml), and distilled water (3×70 ml), then dried over sodium sulfate and evaporated to give a solid. Silica gel column chromatography, CHCl$_3$/MeOH (90:10), afforded a white solid (0.15 g, 75%). TLC, CHCl$_3$/MeOH (88:12), R$_f$=0.33; m.p. 160°–165° C. (dec). EI MASS (m/z, %RA): 958(M)$^+$, 74; 1006(M+Na)$^+$, 100; Anal. calc. for C$_{54}$H$_{87}$O$_{10}$N$_7$: C 65.23, H 8.62, N 9.86. Found: C 65.24, H 8.62, N 9.82.

EXAMPLE 7

Preparation of [SEQ ID NO. 35] Trigonellyl-Ala-Gln-Leu-Pro-Gly-Cholesteryl Ester Methylsulfate (7):

[SEQ ID NO. 34] Nicotinoyl-Ala-Gln-Leu-Pro-Gly-cholesteryl ester (6) (0.15 g, 0.157 mmol) was dissolved in 5 ml of methylene chloride and 0.3 ml methanol, 0.065 g (0.516 mmol) of dimethyl sulfate was added and the mixture was allowed to stand for 54 hours at room temperature, the solvent was removed in vacuo and the solid was washed several times with ethyl ether, and recrystallized from methylene chloride and ethyl ether. EI MASS (m/z, %RA): 973, 100; UV (MeOH): $_{max}$265 nm.

EXAMPLE 8

Preparation of [SEQ ID NO. 36] 1,4-Dihydrotrigonellyl-Ala-Gln-Leu-Pro-Gly-Cholesteryl Ester (8):

Trigonellyl-Ala-Gln-Leu-Pro-Gly-cholesteryl ester methylsulfate (7) (0.1 g, 0.1 mmol) was dissolved in 50% aqueous methanol solution (10 ml), sodium bicarbonate (0.06 g, 0.71 mmol) and sodium dithionite (0.08 g, 0.46 mmol) were added and the mixture was allowed to remain at 0° C. for 2 hours and then extracted with 30 ml of methylene chloride. The organic layer was washed with deaerated water several times, then vacuumed to dryness and freeze-dried, affording 70 mg (yield: 70%) of fine yellowish powder. UV (MeOH) nm: 265, 348. This compound reduces methanolic $AgNO_3$ solution slowly at room temperature and the solution obtained shows the UV spectrum of the corresponding quaternary derivative [UV (MeOH): $_{max}$265 nm].

EXAMPLE 9

Preparation of [SEQ ID NO. 37] Boc-Ala-Gln-Leu-Pro-Gly-Cholesteryl Ester (9):

[SEQ ID NO. 32] Boc-Ala-Gln-Leu-Pro-Gly-O-cholesterol ester (5) (1.34 g, 1.406 mmol) was deblocked with TFA as described above. Boc-Ala-OH (0.32 g, 1.69 mmol) was treated with HOBt (0.33 g, 2.44 mmol) and DCC (0.81 g, 3.92 mmol) in methylene chloride (10 ml) at 0° C. for 10 minutes and then at room temperature for 60 minutes. The TFA salt prepared above in methylene chloride (10 ml) was added and DIEA was used to adjust the pH to neutrality. After 60 minutes the reaction mixture was filtered, diluted with methylene chloride, and washed successively with citric acid (5%, 3×80 ml), saturated sodium bicarbonate (3×80 ml), and distilled water (3×80 ml), then dried over sodium sulfate and evaporated to give a solid. Silica gel column chromatography, $CHCl_3$/MeOH (90:10), afforded a white solid (1.17 g, 81.25%). TLC, $CHCl_3$/MeOH (90:10), $R_f$=0.25; EI MASS (m/z, %RA) [after deprotection by trifluoroacetic acid]: 924 (M+H)$^+$, 100; 947 (M+Na)$^+$, 88.

EXAMPLE 10

Preparation of [SEQ ID NO. 39] Nicotinoyl-Ala-Ala-Gln-Leu-Pro-Gly-Cholesteryl Ester (10):

[SEQ ID NO. 37] Boc-Ala-Ala-Gln-Leu-Pro-Gly-cholesteryl ester (9) (1.17 g, 1.14 mmol) was deblocked with TFA as described above, Nicotinic Acid (0.169 g, 1.37 mmol) was treated with HOBt (0.265 g, 1.96 mmol) and DCC (0.66 g, 3.19 mmol) in methylene chloride (10 ml) and DMF (4 ml) at 0° C. for 10 minutes and then at room temperature for 60 minutes. The TFA salt prepared above in methylene chloride was added and DIEA was used to adjust the pH to neutrality, After 60 minutes the reaction mixture was filtered, diluted with methylene chloride, and washed successively with citric acid (5%, 3×30 ml), saturated sodium bicarbonate (3×30 ml), and distilled water (3×30 ml), then dried over sodium sulfate and evaporated to give a solid. Silica gel column chromatography, $CHCl_3$/MeOH (85:15), afforded a white solid (0.46 g, 39.25%). TLC, $CHCl_3$/MeOH (88:12), $R_f$=0.42; m.p. 169°-172° C.(dec). EI MASS (m/z, %RA): 1029 (M+H)$^+$, 94; 1052 (M+Na)$^+$, 50.

EXAMPLE 11

Preparation of [SEQ ID NO. 40] Trigonellyl-Ala-Ala-Gln-Leu-Pro-Gly-Cholesteryl Ester Methylsulfate (11):

[SEQ ID NO. 39] Nicotinoyl-Ala-Ala-Gln-Leu-Pro-Gly-cholesteryl ester (10) (0.10 g, 0.097 mmol) was dissolved in 5 ml of methylene chloride. Two drops of methanol and 1 ml of dimethyl sulfate were added and the mixture was kept for 54 hours at room temperature. The solvent was removed in vacuo and the solid was washed several times with ethyl ether, and recrystallized from methylene chloride and ethyl ether. EI MASS (m/z, %RA): 1044 (M+H) +, 100; UV (MeOH): $_{max}$268 nm.

EXAMPLE 12

Preparation of [SEQ ID NO. 41] 1,4-Dihydrotrigonellyl-Ala-Ala-Gln-Leu-Pro-Gly-Cholesteryl Ester (12):

[SEQ ID NO. 40] Trigonellyl-Ala-Ala-Gln-Leu-Pro-Gly--cholesteryl ester methylsulfate (11) (0.115 g, 0.11 mmol) was dissolved in 50% aqueous methanol solution (30 ml), sodium bicarbonate (0.07 g, 0.83 mmol) and sodium dithionite (0.09 g, 0.52 mmol) were added. The mixture was allowed to remain at 0° C. for 2 hours, then was extracted with 30 ml of methylene chloride. The organic layer was washed with deaerated water several times, then vacuumed to dryness and freeze-dried to afford 40 mg (yield: 34.78%) of yellowish fine powder. UV (MeOH) nm:268, 347. This compound reduces methanolic $AgNO_3$ solution slowly at room temperature and the solution obtained shows the UV spectrum of the corresponding quaternary derivative [UV (MeOH): 268 nm].

EXAMPLE 13

Preparation of [SEQ ID NO. 43] Boc-Pro-Gln-Leu-Pro-Gly-Cholesteryl Ester (13):

[SEQ ID NO. 30] Boc-Gln-Leu-Pro-Gly-cholesteryl ester (4) (1.77 g, 1.14 mmol) was deblocked with TFA as described above. Boc-Pro-OH (0.52 g, 2.41 mmol) was treated with HOBt (0.47 g, 3.45 mmol) and DCC (1.16 g, 5.62 mmol) in methylene chloride (20 ml) at 0° for 10 minutes and then at room temperature for 60 minutes. The TFA salt prepared above in methylene chloride (25 ml) was added and DIE was used to adjust the pH to neutrality. After 60 minutes the reaction mixture was filtered, diluted with methylene chloride, and washed successively with citric acid (5%, 3×50 ml), saturated sodium bicarbonate (3×50 ml), and distilled water (3×50 ml), then dried over sodium sulfate and evaporated to give a solid. Silica gel column chromatography, $CHCl_3$/MeOH (95:5), afforded a white solid (1.66 g, 84.7%). EI MASS (m/z, %RA): 879(M+H)$^+$, 100; 1007 (M+K)$^+$, 98.

EXAMPLE 14

Preparation of [SEQ ID NO. 45] Nicotinyl-Pro-Gln-Leu-Pro-Gly-Cholesteryl Ester (14):

[SEQ ID NO. 43] Boc-Pro-Gln-Leu-Pro-Gly-cholesteryl ester (13) (0.4 g, 0.41 mmol) was deblocked with TFA as described above. Nicotinic Acid (0.06 g, 0.49 mmol) was treated with HOBt (0.095 g, 0.7 mmol) and DCC (0.24 g, 1.16 mmol) in methylene chloride (20 ml) and DMF (2 ml) at 0° C. for 10 minutes and then at room temperature for 60 minutes. The TFA salt prepared above in methylene chloride (13 ml) was added and DIEA was used to adjust the pH to neutrality. After 60 minutes the reaction mixture was filtered, diluted with methylene chloride, and washed successively with citric acid (5%, 3×30 ml), saturated sodium bicarbonate (3×30 ml), and distilled water (3×30 ml), then dried over sodium sulfate and evaporated to give a solid. Silica gel column chromatography, $CHCl_3$/MeOH (50:50), afforded a white solid (0.28 g, 69.6%). TLC, $CHCl_3$/MeOH (88:12), $R_f$=0.36; EI MASS (m/z, %RA): 984 (M+H)$^+$, 100; 1007 (M+Na)$^+$, 30.

EXAMPLE 15

Preparation of [SEQ ID NO. 46] Boc-Ala-Pro-Gln-Leu-Pro-Gly-Cholesteryl Ester (15):

[SEQ ID NO. 43] Boc-Pro-Gln-Leu-Pro-Gly-cholesteryl ester (13) (0.6 g, 0.61 mmol) was deblocked with TFA as described above. Boc-Ala-OH (0.14 g, 0.74 mmol) was treated with HOBt (0.14 g, 1.04 mmol) and DCC (0.35, 1.69 mmol) in methylene chloride (16 ml) at 0° C. for 10 minutes and then at room temperature for 60 minutes. The TFA salt prepared above in methylene chloride (9 ml) was added and DIEA was used to adjust the pH to neutrality. After 60 minutes the reaction mixture was filtered, diluted with methylene chloride, and washed successively with citric acid (5%, 3×30 ml), saturated sodium bicarbonate (3×30 ml), and distilled water (3×30 ml), then dried over sodium sulfate and evaporated to give a solid. Silica gel column chromatography, $CHCl_3$/MeOH (90:10), afforded a white solid (0.41 g, 63.7% ).

EXAMPLE 16

Preparation of [SEQ ID NO. 48] Nicotinoyl-Ala-Pro-Gln-Leu-Pro-Gly-Cholesteryl Ester (16):

[SEQ ID NO. 46] Boc-Ala-Pro-Gln-Leu-Pro-Gly-cholesteryl ester (15) (0.41 g, 0.39 mmol) was deblocked with TFA as described above. Nicotinic Acid (0.058 g, 0.47 mmol) was treated with HOBt (0.091 g, 0.67 mmol) and DCC (0.226 g, 1.09 mmol) in methylene chloride (11 ml) and DMF (2 ml) at 0° C. for 10 minutes and then at room temperature for 60 minutes. The TFA salt prepared above in methylene chloride (13 ml) was added and DIEA was used to adjust the pH to neutrality. After 60 minutes the reaction mixture was filtered, diluted with methylene chloride, and washed successively with citric acid (5%, 3×40 ml), saturated sodium bicarbonate (3×40 ml), and distilled water (3×40 ml), the dried over sodium sulfate and evaporated to give a solid. Silica gel column chromatography, $CHCl_3$/MeOH (83:17), afforded a white solid (0.28 g, 68% ). TLC, $CHCl_3$/MeOH (88:12), $R_f$=0.51; m.p. 146°–147° C. EI MASS $(M+H)^+$100; 1078 $(M+Na)^+$, 84; Anal. calc. for $C_{59}H_{92}O_{10}N_8$: C 66.02, H 8.64, N 10.44. Found: C 65.49, H 8.57, N 10.41.

EXAMPLE 17

Preparation of [SEQ ID NO. 49] Boc-Pro-Pro-Gln-Leu-Pro-Gly-cholesteryl Ester (17):

[SEQ ID NO. 43] Boc-Pro-Gln-Leu-Pro-Gly-cholesteryl ester (13) (0.56 g, 0.57 mmol) was deblocked with TFA as described above. Boc-Pro-OH (0.15 g, 0.69 mmol) was treated with HOBt (0.13 g, 0.99 mmol) and DCC (0.33 g, 1.60 mmol) in methylene chloride (13 ml) at 0° C. for 10 minutes and then at room temperature for 60 minutes. The TFA salt prepared above in methylene chloride (13 ml) was added and DIEA was used to adjust the pH to neutrality. After 60 minutes the reaction mixture was filtered, diluted with methylene chloride, and washed successively with citric acid (5%, 3×30 ml), saturated sodium bicarbonate (3×30 ml), and distilled water (3×30 ml), then dried over sodium sulfate and evaporated to give a solid. Silica gel column chromatography, $CHCl_3$/MeOH (90:10), afforded a white solid (0.41 g, 63.7%). TLC, $CHCl_3$/MeOH (90:10), $R_f$=0.47.

EXAMPLE 18

Preparation of [SEQ ID NO. 52] Nicotinoyl-Pro-Pro-Gln-Leu-Pro-Gly-Cholesteryl Ester (18):

[SEQ ID NO. 49] Boc-Pro-Pro-Gln-Leu-Pro-Gly-cholesteryl ester (17) (0.33 g, 0.31 mmol) was deblocked with TFA as described above. Nicotinic Acid (0.076 g, 0.62 mmol) was treated with HOBt (0.119 g, 0.88 mmol) and DCC (0.296 g, 1.43 mmol) in methylene chloride (14 ml) and DMF (1 ml) at 0° C. for 10 minutes and then at room temperature for 60 minutes. The TFA salt prepared above in methylene chloride (20 ml) was added and DIEA was used to adjust the pH to neutrality. After 60 minutes the reaction mixture was filtered, diluted with methylene chloride, and washed successively with citric acid (5%, 3×30 ml), saturated sodium bicarbonate (3×30 ml), and distilled water (3×30 ml), then dried over sodium sulfate and evaporated to give a solid. Silica gel column chromatography, $CHCl_3$/MeOH (50:50), afforded a white solid (0.28 g, 69.6%). TLC, $CHCl_3$/MeOH (88:12), $R_f$=0.37; Anal. calc. for $C_{61}H_{94}O_{10}N_8$: C 66.64, H 8.43, N 10.19. Found: C 66.49, H 8.46, N 10.16.

EXAMPLE 19

Preparation of [SEQ ID NO. 53] Trigonellyl-Pro-Gln-Leu-Pro-Gly-Cholesteryl Ester Methylsulfate (19):

Repetition of the procedure of EXAMPLE 11, using an equivalent quantity of nicotinoyl-Pro-Gln-Leu-Pro-Gly-cholesteryl ester (14) in place of the nicotinoyl-Ala-Ala-Gln-Leu-Pro-Gly-cholesteryl ester (10) there employed affords the title compound (19), having the structural formula [SEQ ID NO. 53]

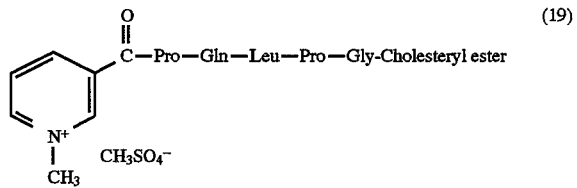

EXAMPLE 20

Preparation of [SEQ ID NO. 54] 1,4-Dihydrotrigonellyl-Pro-Gln- Leu-Pro-Gly-Cholesteryl Ester (20):

Repetition of the procedure of EXAMPLE 12, using an equivalent quantity of [SEQ ID NO. 53] trigonellyl-Pro-Gln-Leu-Pro-Gly-cholesteryl ester methylsulfate (19) in place of [SEQ ID NO. 40] the nicotinoyl-Ala-Ala-Gln-Leu-Pro-Gly-cholesteryl ester methylsulfate (11) there employed affords the title compound (20), having the structural formula[SEQ ID NO. 54]

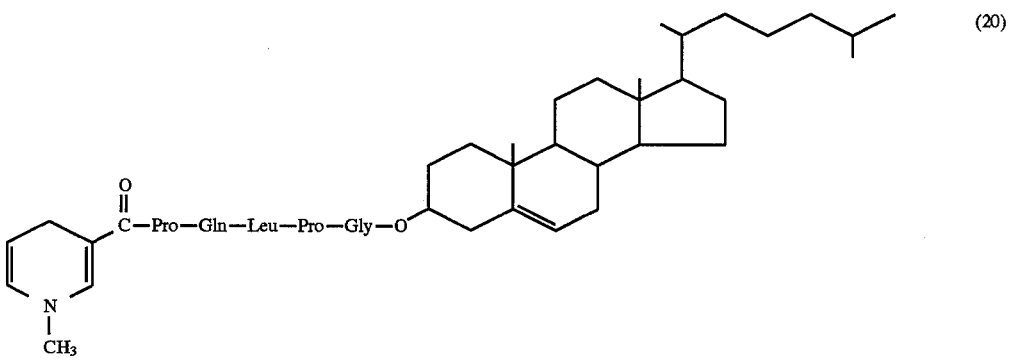

(20)

EXAMPLE 21

Preparation of [SEQ ID NO. 55] Trigonellyl-Ala-Pro-Gln-Leu-Pro-Gly-Cholesteryl Ester Methylsulfate (21):

Repetition of the procedure of EXAMPLE 11, using an equivalent quantity of [SEQ ID NO. 48] nicotinoyl-Ala-Pro-Gln-Leu-Pro-Gly-cholesteryl ester (16) in place of [SEQ ID NO. 39] the nicotinoyl-Ala-Ala-Gln-Leu-Pro-Gly-cholesteryl ester (10) there employed affords the title compound (21), having the structural formula [SEQ ID NO. 55]

Repetition of the procedure of EXAMPLE 11, using an equivalent quantity of [SEQ ID NO. 52] nicotinoyl-Pro-Pro-Gln-Leu-Pro-Gly-cholesteryl ester (18) in place of [SEQ ID NO. 39] the nicotinoyl-Ala-Ala-Gln-Leu-Pro-Gly-cholesteryl ester (10) there employed affords the title compound (23), having the structural formula [SEQ ID NO. 57]

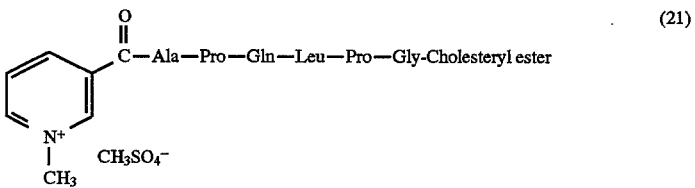

(21)

EXAMPLE 22

Preparation of [SEQ ID NO. 56] 1,4-Dihydrotrigonellyl-Ala-Pro-Gln-Leu-Pro-Gly-Cholesteryl Ester (22):

Repetition of the procedure of EXAMPLE 12, using an equivalent quantity of [SEQ ID NO. 55] trigonellyl-Ala-Pro-Gln-Leu-Pro-Glu-cholesteryl ester methylsulfate (21) in place of [SEQ ID NO. 40] the trigonellyl-Ala-Ala-Gln-Leu-Pro-Gly-cholesteryl ester methylsulfate (11) there employed affords the title compound (22), having the structural formula [SEQ ID NO. 56]

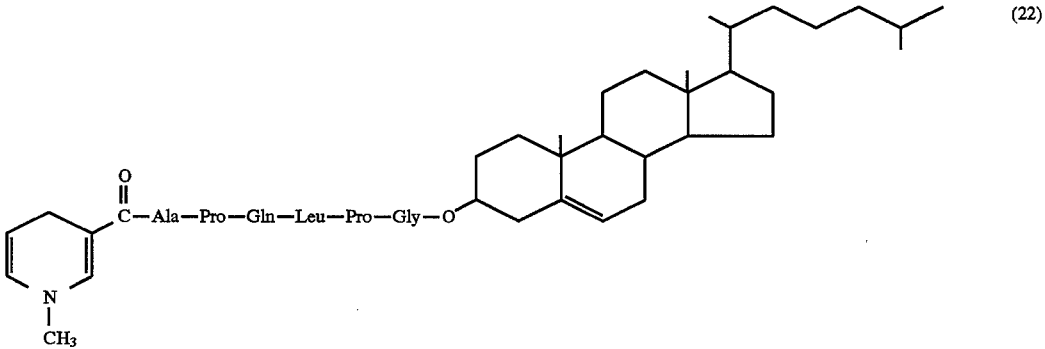

(22)

EXAMPLE 23

Preparation of [SEQ ID NO. 57] Trigonellyl-Pro-Pro-Gln-Leu-Pro-Gly-Cholesteryl Ester Methylsulfate (23):

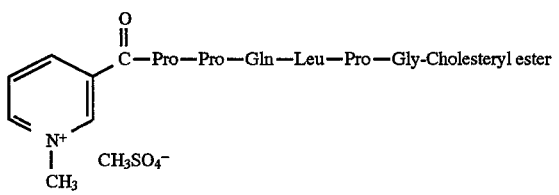

(23)

EXAMPLE 24

Preparation of [SEQ ID NO. 58] 1,4-Dihydrotrigonellyl-Pro-Pro-Gln-Leu-Pro-Gly-Cholesteryl Ester (24):

Repetition of the procedure of EXAMPLE 12, using an equivalent quantity of [SEQ ID NO. 52] trigonellyl-Pro-Pro-Gln-Leu-Pro-Gly-cholesteryl ester methylsulfate (23) in place of [SEQ ID NO. 40] the trigonellyl-Ala-Ala-Gln-Leu-Pro-Gly-cholesteryl ester methylsulfate (11) there employed affords the title compound (24), having the structural formula[SEQ ID NO. 58]

such as cholesterol at the C-terminal; and single or double spacers between redox moiety and N-terminal. One such lipophilic "molecular package" is 1,4-dihydrotrigonellyl-Ala-Tyr-Arg-cholesteryl ester, a representative kyotorphin-CDS.

In Scheme VI and EXAMPLES 25–54 which follow, abbreviations generally follow IUPAC-IUB recommendations as published in *J. Biol. Chem.* 264, 668–673 (1989). Other abbreviations include: Boc, t-butyloxycarboxyl; CDS, chemical delivery system; DCC, dicyclohexylcarbodiimide; DCU, dicyclohexylurea; DMAP, 4-dimethylaminopyridine;

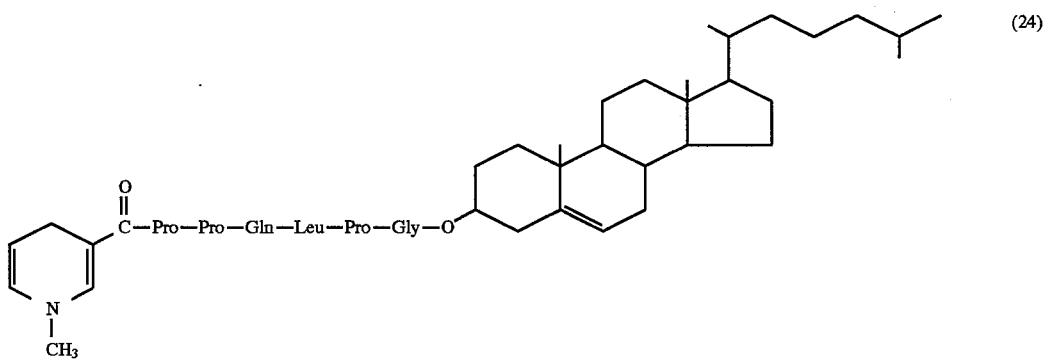

Reaction Scheme VI below depicts a representative synthesis of yet other peptides of the invention and intermediates thereto. The synthesis shown in Scheme VI and variations thereof are described in EXAMPLES 25–54 hereinafter. The peptide final products are chemical delivery systems for the brain-enhanced delivery of kyotorphin (L-tyrosyl-L-arginine), which has the structural formula

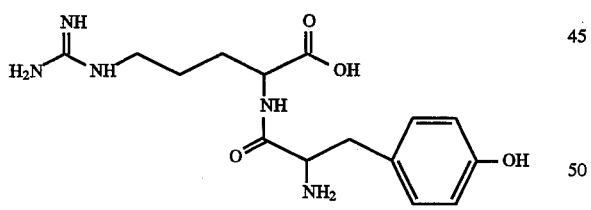

Kyotorphin is an endogenous dipeptide which exhibits analgesic action by mediation of the release of enkephalin in the brain. It may also increase the synaptosomal concentration of intracellular calcium in neuronal nerve terminals and play a neurotransmitter role. Therefore, the delivery of kyotorphin into the CNS (central nervous system) for the management of pain would be desirable. However, as with other peptides, it is difficult to deliver kyotorphin across the BBB (brain-blood barrier) and into the CNS due to the properties of the peptides: poor permeability through the BBB and metabolic instability. In accord with the present invention kyotorphin has been modified with (i) a dihydropyridine⇌pyridimium salt redox system (analogous to the endogenous NADH⇌NAD$^+$ coenzyme system) at the N-terminal; (ii) esterification with a large lipophilic moiety DMF, dimethylformamide; Et$_3$N, triethylamine; Et$_2$O, diethyl ether; Fmoc, 9-florenylmethoxycarbonyl; HOBt, N-hydroxybenzotriazole; Pmc, 2,2,5,7,8-pentamethylchroman-6-sulfonyl; TFA, trifluoroacetic acid; cholesteryl ester, the ester of the 3-hydroxy group of cholesterol with the carboxylic acid function of the C-terminal amino acid. All amino acids in Scheme VI and in EXAMPLES 25–54 are L-configuration. Abbreviations follow the recommendations of the IUPAC-IUB Commission on Biological Nomenclature as given in *Eur. J. Biochem.* 138, 9–37 (1964).

Scheme VI
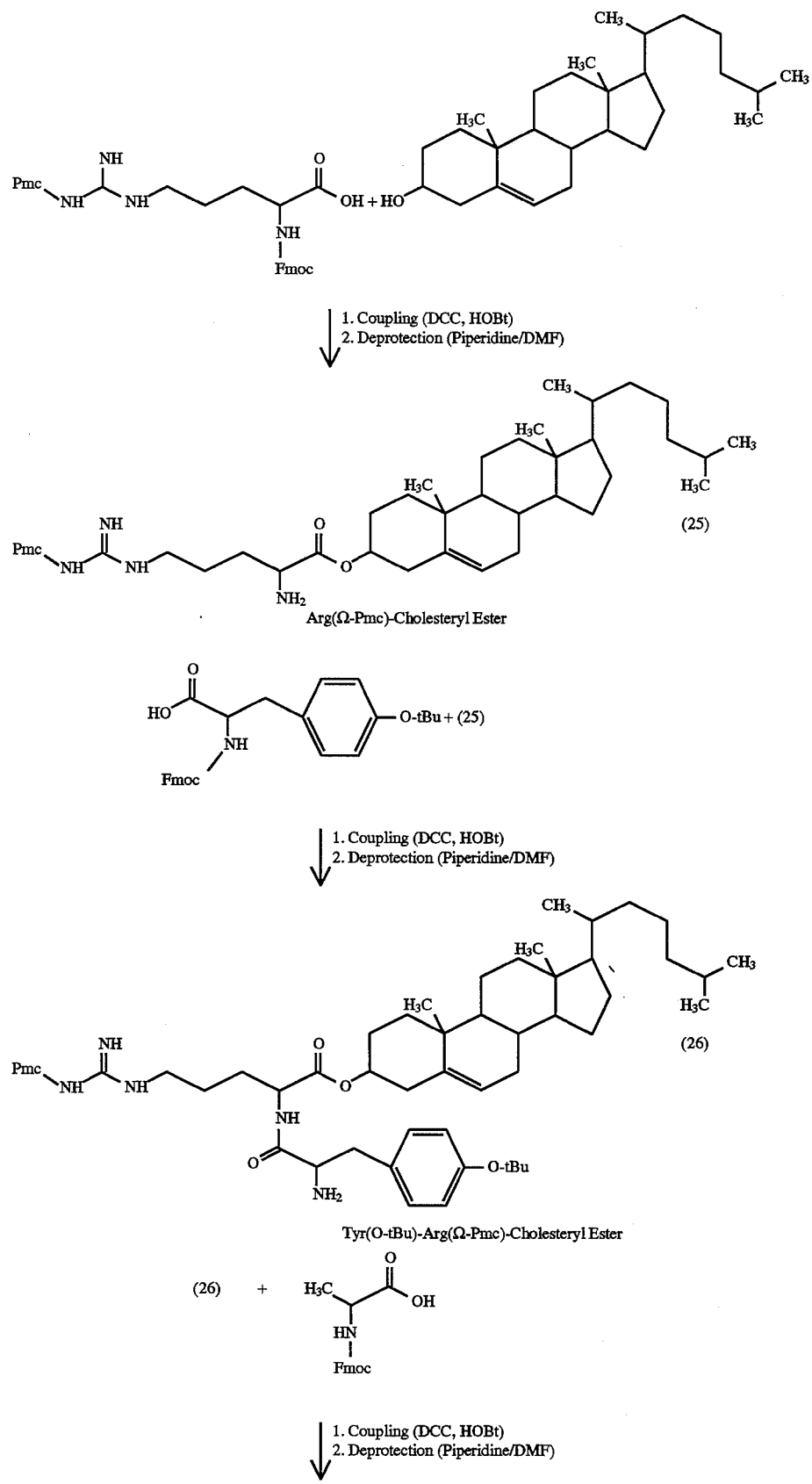

-continued
Scheme VI
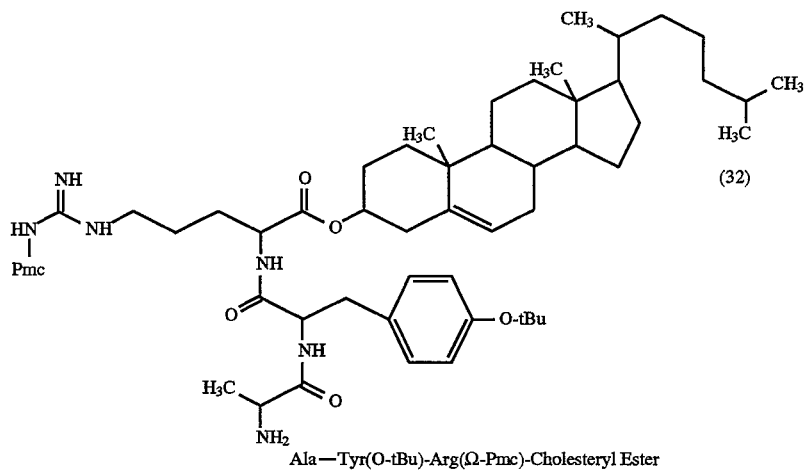
Ala—Tyr(O-tBu)-Arg(Ω-Pmc)-Cholesteryl Ester (32)
(32) + nicotinic acid
1. Coupling (DCC, DMAP)
2. Deprotection (Piperidine/DMF)
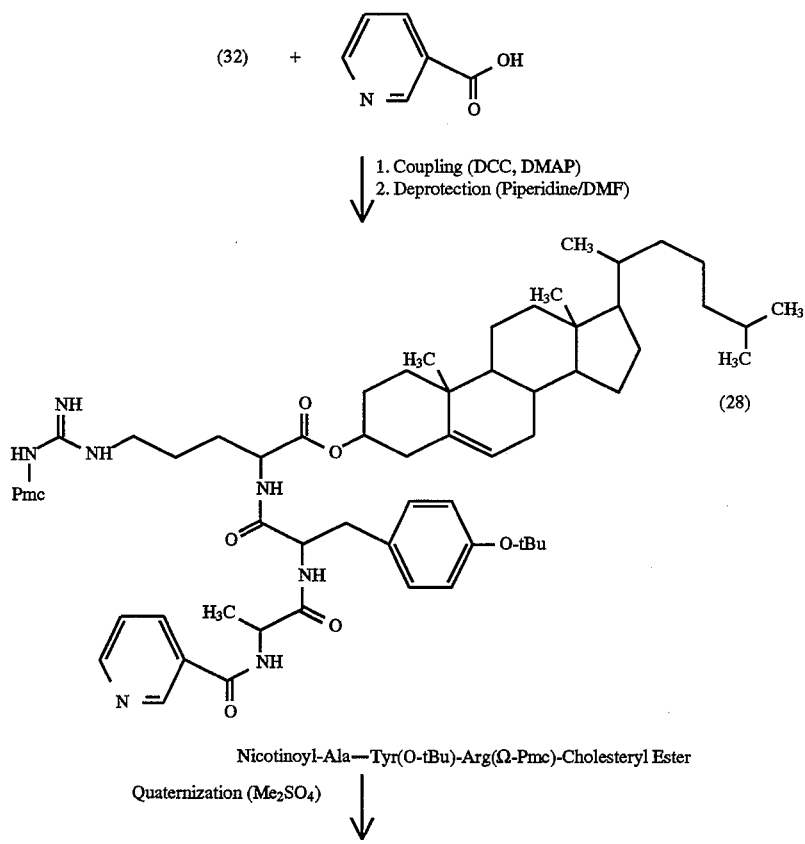
Nicotinoyl-Ala—Tyr(O-tBu)-Arg(Ω-Pmc)-Cholesteryl Ester (28)
Quaternization (Me₂SO₄)

-continued
Scheme VI
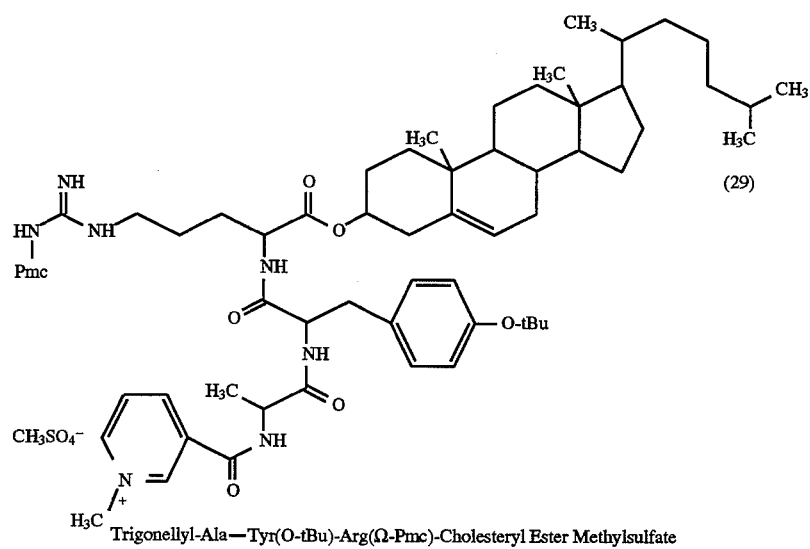
Trigonellyl-Ala—Tyr(O-tBu)-Arg(Ω-Pmc)-Cholesteryl Ester Methylsulfate (29)
Deprotection (TFA/H$_2$O)
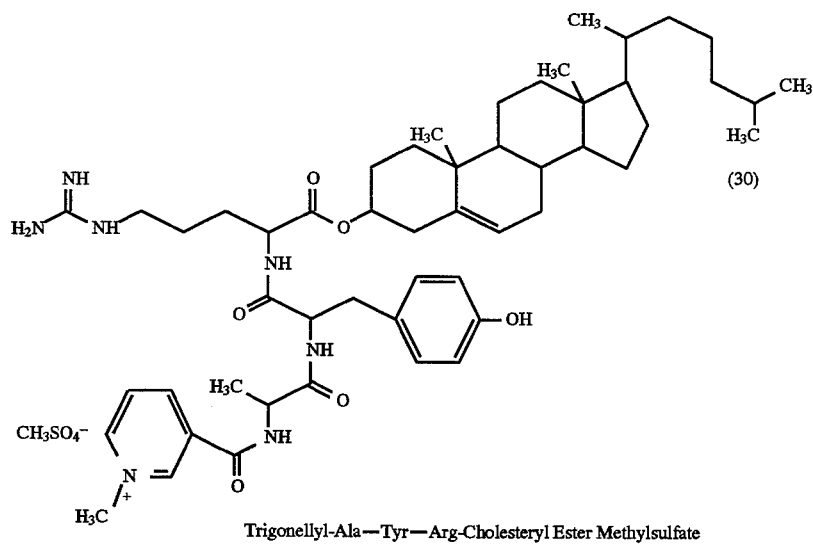
Trigonellyl-Ala—Tyr—Arg-Cholesteryl Ester Methylsulfate (30)
Reduction (Na$_2$S$_2$O$_4$)

-continued
Scheme VI

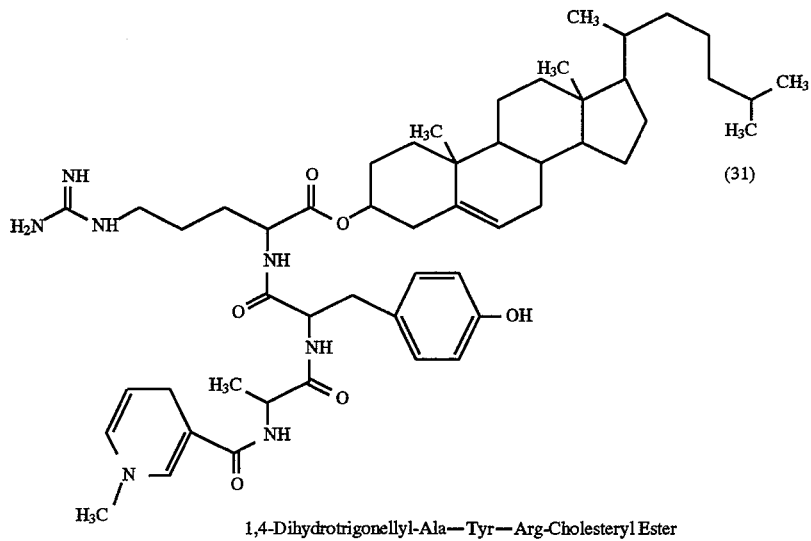

1,4-Dihydrotrigonellyl-Ala—Tyr—Arg-Cholesteryl Ester

The reactions depicted in Scheme VI above or alternative reactions are described in more detail in the EXAMPLES which follow, which are for the purpose of illustration and are in no way limitative of the invention. In these EXAMPLES, all solvents were reagent grade. Boc- and Fmoc-amino acid derivatives were peptide synthesis grade and purchased from BaChera Inc. Thin Layer Chromatography CTLC) was carried out using Merck DC-Alufolien Kiesegel (silica gel) 60 $F_{254}$ coated aluminum plates. Mass Spectra were recorded on a Vestec 200 ES spectrometer by electrospray ionization method.

EXAMPLE 25

Preparation of Arg(Ω-Pmc)-Cholesteryl Ester (25):

N-α-Fmoc-Ω-Pmc-Arg-OH (3.30 g, 5.00 mmol) was dissolved in 35 ml of $CH_2Cl_2$. Then, 2 equivalents of cholesterol (3.88 g, 10.0 mmol) dissolved in 75 ml of $CH_2Cl_2$ were added while stirring at room temperature, followed immediately by 1.2 equivalents (1.32 g, 6.0 mmol) of DCC dissolved in 15 ml $CH_2Cl_2$ and 1.4 equivalents (0.86 g, 7.0 mmol) of DMAP dissolved in 15 ml of DMF. The reaction vessel was stoppered under nitrogen and allowed to stir for 48 hours, then the DCU obtained was removed by filtration. The solvent was removed in vacuo to afford Fmoc-Arg(DPmc)-cholesteryl ester, which was dissolved in 50 ml of 1:1 piperidine/DMF and stirred at room temperature for 30 minutes. Removal of the solvent in vacuo afforded Arg(Ω-Pmc)-cholesteryl ester (25). Silica gel column chromatography was used to purify the compound. The mobile phase used was $CH_3OH/CHCl_3$ (1:9). 2.84 g (3.52 mmol) compound (25) was obtained. Therefore, the overall yield of this step was 70.4%. TLC showed 1 spot: $R_f$=0.50 in $CH_3OH/CHCl_3$ (1:19) and the mass spectrum showed one major peak center at m/z=809 (M+H$^+$) which matched the calculated molecular weight of Arg(Ω-Pmc)-cholesteryl ester and one minor peak centered at m/z=1618 (2M+H$^+$).

EXAMPLE 26

Preparation of Tyr(O-tBu)-Arg(Ω-Pmc)-Cholesteryl Ester (26):

Arg(Ω-Pmc)-cholesteryl ester (25) (2.60 g, 3.20 mmol) was dissolved in 25 ml of $CH_2Cl_2$. Then, 1.50 g (3.20 mmol) of N-α-Fmoc-(O-tBu)-Tyr-OH (1 equivalent) dissolved in 25 ml of $CH_2Cl_2$ was added while stirring at room temperature, followed immediately by 0.72 g (3.5 mmol) of DCC (1.1 equivalents) dissolved in 10 ml of $CH_2Cl_2$ and 0.54 g (4.0 mmol) of HOBt (1.25 equivalents) dissolved in 10 ml of DMF. The reaction vessel was stoppered under nitrogen and allowed to stir for 48 hours and the DCU obtained was timred off. The solvent was removed in vacuo to give Fmoc-Tyr(O-tBu)-Arg(Ω-Pmc)-cholesteryl ester. That product was dissolved in 25 ml of piperidine/DMF (1:1) and was stirred at room temperature for half an hour. Then the solvent was removed in vacuo, according Tyr (O-tBu)-Arg(Ω-Pmc)-cholesteryl ester. Silica gel column chromatography was employed to purify the compound. The mobile phase used was $CH_3OH/CHCl_3$ (1:9). 2.48 g (2.41 mmol) of compound was obtained. Therefore, the overall yield of this step was 75.4%. TLC showed 1 spot: $R_f$=0.45 in $CH_3OH/CHCl_3$ (1:9) and the mass spectrum showed one major peak center at m/z=1029 (M+H$^+$) which matched the calculated molecular weight of Tyr(O-tBu)-Arg(Ω-Pmc)-cholesteryl ester.

EXAMPLE 27

Preparation of Nicotinoyl-Ala-OH (27):

Alanine t-butyl ester (0.454 g, 2.50 mmol) was dissolved in 15 ml of $CH_2Cl_2$, then $Et_3N$ (0.252 g, 2.50 mmol) was added and the mixture was stirred for 10 minutes at room temperature. Then nicotinic acid (0.31 g, 5.0 mmol) in 8 ml of DMF and HOBt (0.43 g, 3.20 mmol) in 5 ml of DMF were added, followed by DCC (0.52 g, 3.0 mmol) in 10 ml of $CH_2Cl_2$. The mixture was stoppered and stirred overnight at room temperature. The DCU which formed was removed by filtration and the solvent was removed in vacuo. The residue was dissolved in 25 ml of $CHCl_3$ and washed successively three times with 5% acetic acid/$H_2O$, three times with 7% $NaHCO_3/H_2O$ and once with saturated NaCl solution. The organic layer was dried over anhydrous $Na_2SO_4$ for one hour, then the solvent was removed in vacuo to give nicotinoyl-alanine t-butyl ester. That product was dissolved in 25 ml of 1:1 TFA/$CHCl_3$ and was stirred at room temperature for 30 minutes. The solvent was removed in vacuo, the residue was triturated three times with $Et_2O$ and then recrystallized from $Et_2O$ to give nicotinoyl-alanine (27). TLC showed one spot, $R_f$=0.42 in 1:9 $CH_3OH/CHCl_3$. Mass spectrum showed one major peak centered at m/z=195 (M+H$^+$) which matched the calculated molecular weight. The product was obtained in 53% overall yield (0.257 g, 1.325 mmol).

EXAMPLE 28

Preparation of Nicotinoyl-Ala-Tyr(O-tBu)-Arg(Ω-Pmc)-Cholesteryl Ester (28):

Tyr(O-tBu)-Arg(Ω-Pmc)-cholesteryl ester (1.20 g, 1.17 mmol) (26) was dissolved in 25 ml of $CH_2Cl_2$. Then, one equivalent (0.22 g, 1.17 mmol) of nicotinoyl-Ala-OH(27) dissolved in 25 ml of $CH_2Cl_2$ was added while stirring at room temperature, followed immediately by 1.1 equivalents of DCC (0.26 g, 1.26 mmol) dissolved in 10 ml of $CH_2Cl_2$ and 1.27 equivalents of HOBt (0.20 g, 1.48 mmol) dissolved in 5 ml of DMF. The reaction vessel was stoppered under nitrogen and allowed to stir for 96 hours, then the DCU which formed was removed by filtration and the solvent was removed in vacuo. Silica gel column chromatography was used to purify the compound. The mobile phase used was $CH_3OH/CH_3CN/CHCl_3$ (1:1:8). 0.859 g (0.7126 mmol) compound was obtained. Therefore, the overall yield of this step was 60.9%. TLC showed 1 spot, $R_f$=0.57 in $CH_3OH/CHCl_3$ (1:9) and the mass spectrum showed one major peak centered at m/z=1205 (M+H$^+$) which matched the calculated molecular weight of nicotinoyl-Ala-Tyr(O-tBu)-Arg(Ω-Pmc)-cholesteryl ester (28).

EXAMPLE 29

Preparation of Trigonellyl-Ala-Try(O-tBu)-Arg(Ω-Pmc)-Cholesteryl Ester Methylsulfate (29):

Nicotinoyl-Ala-Tyr(O-tBu)-Arg(Ω-Pmc)-cholesteryl ester (28) (0.50 g, 0415 mmol) was dissolved in 15 ml of $CH_2Cl_2$. Then, 5 equivalents of $(CH_3)_2SO_4$ (0.26 g, 2.0 mmol) dissolved in 25 ml of $CH_2Cl_2$ was added while stirring at room temperature. The reaction vessel was stoppered and stirred overnight. The solvent was removed in vacuo and the product was triturated with $Et_2O$ 3 times and recrystallized from $Et_2O$. The mass spectrum showed one major peak centered at m/z=1219 (M$^+$) which matched the calculated molecular weight of trigonellyl-Ala-Tyr(O-tBu)-Arg(Ω-Pmc)-cholesteryl ester methylsulfate (28). That product was obtained in 98.8% yield (0.5 g).

EXAMPLE 30

Preparation of Trigonellyl-Ala-Tyr-Arg-Cholesteryl Ester Methylsulfate (30):

Trigonellyl-Ala-Tyr(O-tBu)-Arg(Ω-Pmc)-cholesteryl ester methylsulfate (29) (0.5 g) was dissolved in 25 ml of 1:1 TFA/CHCl$_3$ and stirred at room temperature for one hour. The solvent was then removed in vacuo and the residue was triturated three times with $Et_2O$, then was recrystallized from $Et_2O$ to afford 0.28 g (0.31 mmol) of trigonellyl-Ala-Tyr-Arg-cholesteryl ester methylsulfate in 75.6% yield. The mass spectrum showed that the deprotection was not completed. There were scattered peaks, although the highest peak had a m/z=896 (M$^+$) which matched the calculated molecular weight of Trigonellyl-Ala-Tyr-Arg-cholesteryl ester methylsulfate. The other peaks included (1) the compound+Pmc (2) the compound+tBu, and (3) the compound+Pmc+tBu.

EXAMPLE 31

Preparation of 1,4-Dihydrotrigonellyl-Ala-Tyr-Arg-Cholesteryl Ester (31):

Trigonellyl-Ala-Tyr-Arg-cholesteryl ester methylsulfate (0.09 g, 0.01 mmol) (30) was dissolved in 20 ml of $H_2O$, then NaHCO$_3$ (0.05 g, 0.06 mmol) and Na$_2$S$_2$O$_4$ (0.07 g, 0.04 mmol) were added in small portions while stirring at 0° C. The reaction vessel was stoppered under nitrogen and allowed to stir for 1.5 hours at 0° C. Then, 10 ml of CHCl$_3$ were added to extract the desired 1,4-dihydrotrigonellyl-Ala-Tyr-Arg-cholesteryl ester (31), which was not soluble in water. The extraction was repeated 3 times, the organic layers were combined and the solvent was removed in vacuo, to afford 0.056 g of compound (31), yield 62.2%. TLC showed 4 spots: One major spot with $R_f$=0.43, three minor spots with $R_f$ values at 0.57, 0.52, 0.50, respectively.

EXAMPLE 32

Preparation of Ala-Tyr(O-tBu)-Arg(Ω-Pmc)-Cholesteryl Ester (32):

Tyr(O-tBu)-Arg(Ω-Pmc)-cholesteryl ester (26) (2.40 g, 2.4 mmol) was dissolved in 25 ml of $CH_2C_2$. Then 1 equivalent of N-α-Fmoc-Ala-OH (0.75 g, 2.4 mmol) dissolved in 10 ml of $CH_2Cl_2$ was added while stirring at room temperature, followed immediately by 1.25 equivalents of DCC (0.60 g, 3.0 mmol) dissolved in 10 ml of $CH_2Cl_2$ and 1.25 equivalents of HOBt (0.4 g, 3.0 mmol) dissolved in 10 ml of DMF. The reaction vessel was stoppered under nitrogen and allowed to stir for 48 hours, then the DCU which was formed was removed by filtration and the solvent was removed in vacuo, to afford Fmoc-Ala-Tyr(O-tBu)-Arg(Ω-Pmc)-cholesteryl ester. That product was dissolved in 25 ml of 1:1 piperidine/DMF and stirred at room temperature for about 30 minutes. Removal of the solvent afforded the desired Ala-Tyr(O-tBu)-Arg(Ω-Pmc)-cholesteryl ester. Silica gel column chromatography was employed to purify the compound. The mobile phase used was $CH_3OH/CHCl_3$ (1:9). 2.14 g (2.0 mmol) compound was obtained. Therefore, the overall yield of this step is 81.1%. TLC showed 1 spot: $R_f$=0.48 in $CH_3OH/CHCl_3$ (1:9).

EXAMPLE 33

Preparation of [SEQ ID NO. 59] Nicotinoyl-Ala-Ala-Tyr(O-tBu)-Arg(Ω-Pmc)-Cholesteryl Ester (33):

Ala-Tyr(O-tBu)-Arg(Ω-Pmc)-cholesteryl ester (32) (1.98 g, 1.80 mmol) was dissolved in 25 ml of $CH_2Cl_2$. Then, 1.1 equivalents of nicotinoyl-Ala-OH (0.38 g, 1.95 mmol) dissolved in 25 ml of $CH_2Cl_2$ were added while stirring at room temperature, followed immediately by 1.1 equivalents of DCC (0.40 g, 2.0 mmol) dissolved in 10 ml of $CH_2Cl_2$ and 1.32 equivalents of HOBt (0.32 g, 2.37 mmol) dissolved in 5 ml of DMF. The reaction vessel was stoppered under nitrogen and allowed to stir for 96 hours. The DCU which formed was removed by filtration and the solvent was removed in vacuo. Silica gel column chromatography was employed to purify the compound. The mobile phase used was $CH_3OH/CH_3CN/CHCl_3$ (1:1:8). 1.64 g (1.29 mmol) compound was obtained. Therefore, the overall yield of this step was 71.6%. TLC showed 1 spot, $R_f$=0.55 in $CH_3OH/CHCl_3$ (1:9) and the mass spectrum showed one major peak centered at m/z=1276 (M+H$^+$) which matched the calculated molecular weight of the product [SEQ ID NO. 59] (33).

EXAMPLE 34

Preparation of [SEQ ID NO. 60] Trigonellyl-Ala-Ala-Tyr(O-tBu)-Arg(Ω-Pmc)-Cholesteryl Ester Methylsulfate (34):

The procedure of EXAMPLE 29 was substantially repeated, except that [SEQ ID NO. 59] nicotinoyl-Ala-Ala-Tyr(O-tBu)-Arg(Ω-Pmc)-cholesteryl ester (33) was used in place of [SEQ ID NO. 60] nicotinoyl-Ala-Tyr(O-tBu)-Arg(Ω-Pmc)-cholesteryl ester (28). The title quaternary salt (34) was obtained in approximately 100% yield. The mass spectrum showed one major peak center at m/z=1290 (M⁺) which matched the calculated molecular weight of [SEQ ID NO. 60] (34).

EXAMPLE 35

Preparation of [SEQ ID NO. 6] Trigonellyl-Ala-Ala-Tyr-Arg-Cholesteryl Ester Methylsulfate (35):

Trigonellyl[SEQ ID NO. 60]-Ala-Ala-Tyr(O-tBu)-Arg(Ω-Pmc)-cholesteryl ester methylsulfate (34) (1.0 g, 0.78 mmol) was dissolved in 25 ml of 19:1 TFA/H$_2$O and stirred at room temperature for one hour. The solvent was removed in vacuo and the residue was triturated three times with Et$_2$O, then recrystallized from Et$_2$O to afford the title compound [SEQ ID NO. 61] (35) in 76.9% yield (0.58 g, 0.60 mmol). The mass spectrum showed that the deprotection was completed, although there still were some very small scattered peaks. The major peak (m/z=967, M⁺) of the compound was prominent (peak area>90% of the total peak areas). It seems this deprotection method is better than the method of EXAMPLE 30.

EXAMPLE 36

Preparation of [SEQ ID NO. 62] 1,4-Dihydrotrigonellyl-Ala-Ala-Tyr-Arg-Cholesteryl Ester (36):

Repetition of the procedure of EXAMPLE 31, but substituting trigonellyl[SEQ ID NO. 61]-Ala-Ala-Tyr-Arg-cholesteryl ester methylsulfate (35) for the quaternary starting material (30) therein affords the title compound (36), having the structural formula [SEQ ID NO. 62]

The title compound is prepared using the general procedure of EXAMPLE 33, but substituting an equivalent quantity of nicotinic acid for the nicotinoyl-Ala-OH there employed.

EXAMPLE 39

Preparation of Trigonellyl-Pro-Tyr(O-tBu)-Arg-(Ω-Pmc)-Cholesteryl Ester Methylsulfate (3):

The procedure of EXAMPLE 34 is substantially repeated, using an equivalent quantity of compound (38) in place of compound (33) [SEQ ID NO. 59], to afford the title compound.

EXAMPLE 40

Preparation of Trigonellyl-Pro-Tyr-Arg-Cholesteryl Ester Methylsulfate. (40):

Repetition of the procedure of EXAMPLE 35, using an equivalent quantity of the quaternary salt (39) in place of compound (34) [SEQ ID NO. 60] affords the desired deprotected derivative (39).

EXAMPLE 41

Preparation of 1,4-Dihydrotrigonellyl-Pro-Tyr-Arg-Cholesteryl Ester (41):

The title compound is obtained by use of the procedure of EXAMPLE 36, substituting the deprotected quaternary (40) for the starting material (35) [SEQ ID NO. 61] employed therein. The product has the structural formula

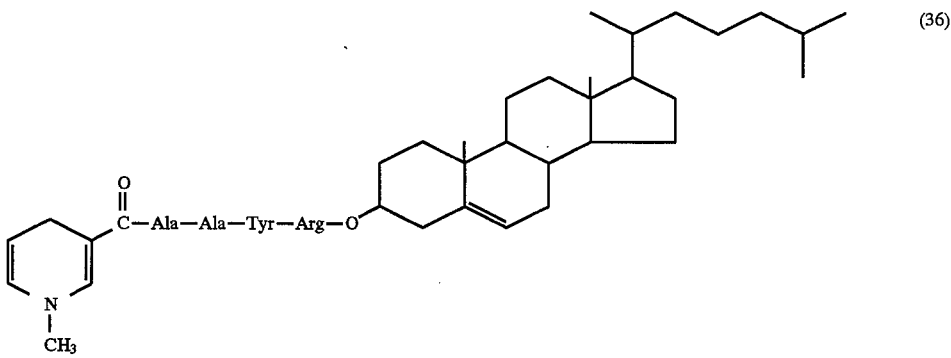

Using adaptations of the synthetic examples given above, the novel starting materials, quaternary intermediates and dihydropyridine final products indicated in the following EXAMPLES can be readily synthesized.

EXAMPLE 37

Preparation of Pro-Tyr(O-tBu)-Arg(Ω-Pmc)-Cholesteryl Ester (37):

The title compound is prepared using the general procedure of EXAMPLE 32, but substituting an equivalent quantity of Boc-Pro-OH for the N-α-Fmoc-Ala-OH there employed.

EXAMPLE 38

Preparation of Nicotinoyl-Pro-Tyr(O-tBu)-Arg-(Ω-Pmc)-Cholesteryl Ester (38):

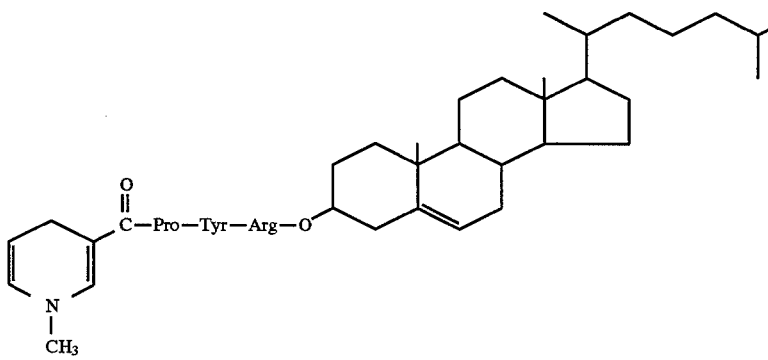

EXAMPLE 42

Preparation of Nicotinoyl-Pro-OH (42):

Proline t-butyl ester is substituted for the alanine t-butyl ester used in EXAMPLE 27 and the procedure of that EXAMPLE is substantially repeated to afford the title compound.

EXAMPLE 43

Preparation of [SEQ ID NO. 63] Nicotinoyl-Pro-Pro-Tyr(O-tBu)-Arg(Ω-Pmc)-Cholesteryl Ester (43):

Compounds (37) and (42) are reacted according to the procedure of EXAMPLE 33 to afford the title compound.

EXAMPLE 44

Preparation of [SEQ ID NO. 64] Trigonellyl-Pro-Pro-Tyr(O-tBu)-Arg(Ω-Pmc)-Cholesteryl Ester Methylsulfate (44):

The title compound is prepared by subjecting compound (43) to the quaternization reaction of EXAMPLE 34.

EXAMPLE 45

Preparation of [SEQ ID NO. 65] Trigonellyl-Pro-Pro-Tyr-Arg-Cholesteryl Ester Methylsulfate (45):

The title compound is prepared by deprotecting compound (44) [SEQ ID NO. 64] according to the method of EXAMPLE 35.

EXAMPLE 46

Preparation of [SEQ ID NO. 66] 1,4-Dihydrotrigonellyl-Pro-Pro-Tyr-Arg-Cholesteryl Ester (46):

The product of EXAMPLE 45 is subjected to the general procedure of EXAMPLE 36 to give the title compound, having the structural formula

EXAMPLE 47

Preparation of [SEQ ID NO. 67] Nicotinoyl-Ala-Pro-Tyr(O-tBu)-Arg(Ω-Pmc)-Cholesteryl Ester (47):

The title compound is prepared according to the method of EXAMPLE 33, utilizing an equivalent quantity of compound (37) in place of compound (32) [SEQ ID NO. 58] therein.

EXAMPLE 48

Preparation of [SEQ ID NO. 68] Trigonellyl-Ala-Pro-Tyr(O-tBu)-Arg (Ω-Pmc)-Cholesteryl Ester Methylsulfate (48):

Repetition of the procedure of EXAMPLE 34, using an equivalent quantity of compound (47) [SEQ ID NO. 67] in place of the compound (33) [SEQ ID NO. 59] utilized therein affords the title compound.

EXAMPLE 49

Preparation of [SEQ ID NO. 69] Trigonellyl-Ala-Pro-Tyr-Arg-Cholesteryl Ester Methylsulfate (49):

The title compound is prepared by deprotecting compound (48) [SEQ ID NO. 68] according to the procedure of EXAMPLE 35.

EXAMPLE 50

Preparation of [SEQ ID NO. 70] 1,4-Dihydrotrigonellyl-Ala-Pro-Tyr-Arg-Cholesteryl Ester (50):

Compound (49) [SEQ ID NO. 69] is subjected to the general procedure of EXAMPLE 36 to give the title compound having the structural formula [SEQ ID NO. 70]

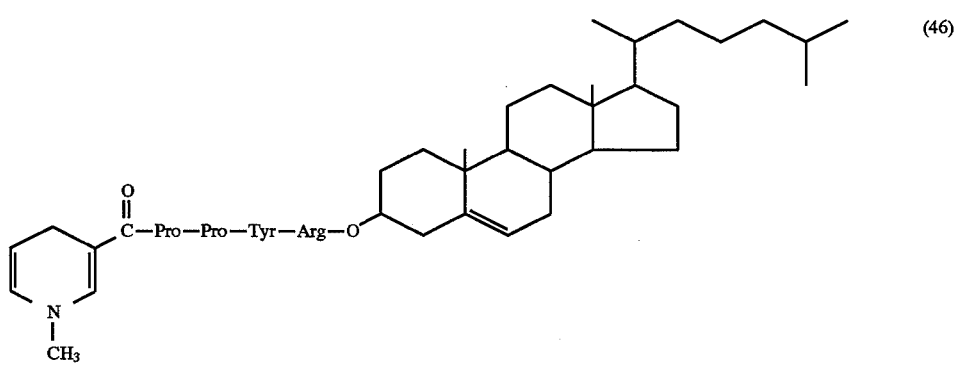

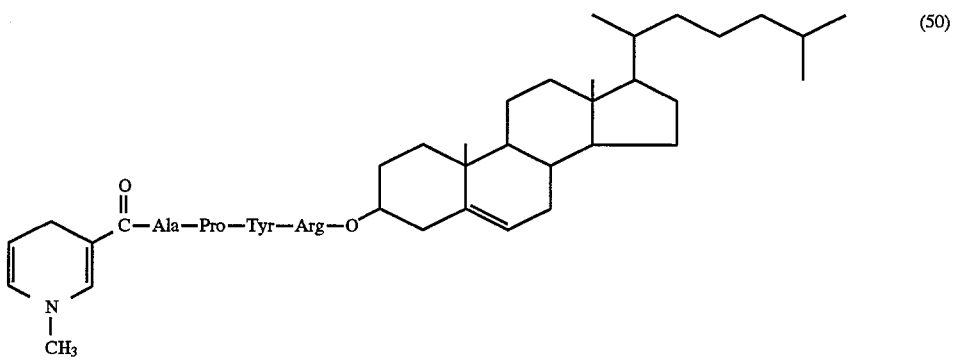

EXAMPLE 51

Preparation of [SEQ ID NO. 71] Nicotinoyl-Pro-Ala-Tyr(O-tBu)-Arg(Ω-Pmc)-Cholesteryl Ester (51):

Compounds (32) and (42) are reacted according to the procedure EXAMPLE 33 to afford the title compound.

EXAMPLE 52

Preparation of [SEQ ID NO. 72] Trigonellyl-Pro-Ala-Tyr(O-tBu)-Arg(Ω-Pmc)-Cholesteryl Ester Methylsulfate (52):

The title compound is prepared by subjecting compound (51) [SEQ ID NO. 71] to the quaternization reaction of EXAMPLE 34.

EXAMPLE 53

Preparation of [SEQ ID NO. 73] Trigonellyl-Pro-Ala-Tyr-Arg-Cholesteryl Ester Methylsulfate (53):

The title compound is prepared by deprotecting compound (52) [SEQ ID NO. 72] according to the method of EXAMPLE 35.

EXAMPLE 54

Preparation of [SEQ ID NO. 74] 1,4-Dihydrotrigonellyl-Pro-Ala-Tyr-Arg-Cholesteryl Ester (54):

The product of EXAMPLE 53 is subjected to the general procedure of EXAMPLE 36 to give the title compound, having the structural formula

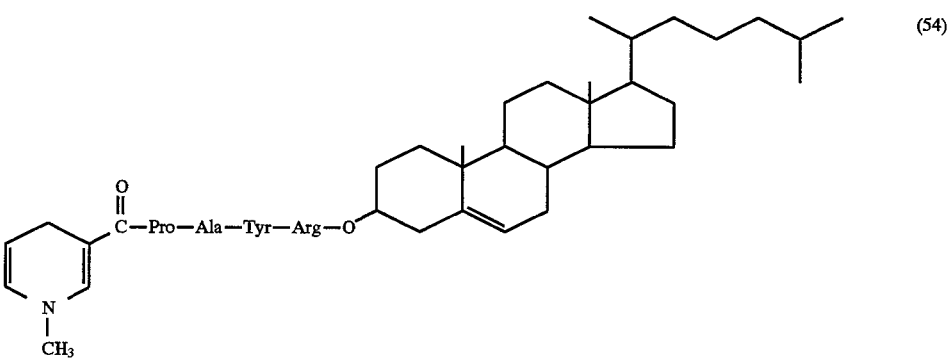

Application of the present invention to enkephalins is detailed in EXAMPLES 55–90 hereinafter, which are for the purpose of illustration only. The peptide final products are chemical delivery systems for the brain-enhanced delivery of a representative enkephalin analog, [SEQ ID NO. 75] H-Tyr-D-Ala-Gly-Phe-D-Leu-OH, also known as DADLE or D-Ala-D-Leu-enkephalin. Enkephalins (i.e., the natural enkephalins and their analogs) are of value for their morphine-like analgesic activity as well as for their beneficial effects on memory.

In EXAMPLES 55–90 which follow, abbreviations are as detailed above for the other EXAMPLES. All amino acids in the group of EXAMPLES to follow have the L-configuration except where the D-configuration is specifically indicated.

While all of the EXAMPLES which follow describe the preparation of novel compounds of the invention or intermediates thereto, certain of the compounds which could be used as intermediates were primarily prepared for comparative purposes. See EXAMPLES 65 and 70–74, which provide compounds lacking the invention's redox targetor moiety, the spacer function or the bulky lipophilic ester grouping.

EXAMPLE 55

Preparation of N-t-Boc-D-Leu-Cholesteryl Ester (55):

To an ice cold solution of 3.86 g (0.01 mol) of cholesterol in 100 ml of dichloromethane, 1.71 g (0.014 mol) of DMAP and 3.23 g (0.014 mol) of N-t-Boc-D-Leu-OH were added. To the stirred cold mixture, 2.88 g (0.014 mol) of DCC were gradually added. The mixture was kept stirring at room temperature and monitored with TLC (silica gel, ethyl acetate) until the spot corresponding to the acid almost disappeared (64 hours). The precipitated DCU was removed by filtration and washed with dichloromethane. The collected filtrate and washing were washed successively, 3 times each with 5% citric acid solution, 5% sodium bicarbonate solution and water, then dried over anhydrous sodium sulfate. The solvent was distilled on rotavap (rotary evaporator) and the residue was chromatographed (silica gel column, dichloromethane). Distillation of the product fraction gave 4.2 g (70% yield) of a solid froth which melted at 55–60 C. Trituration of the solid froth with methanol gave a white crystalline solid, m.p 108°–110° C. $^1$HMR (CDCl$_3$)

δ0.70–2.40 (m, 62H, Cholesterol skeletal and side chain protons+t-Boc); t-Boc appears as a singlet at 1.48 within the multiplet; 4.40–4.90 (m, 3H, cholest. O—C$\underline{H}$+N—C$\underline{H}$⁺(CH$_3$)$_2$—C$\underline{H}$), 5.37 (bd, 1H, cholest.=C$\underline{H}$).

EXAMPLE 56

Preparation of D-Leu-Cholesteryl Ester Trifluoroacetate (56):

To an ice cold solution of 4.2 g (0.007 mol) of compound (55) in 50 ml of dichloromethane, 15 ml of triflouroacetic acid were added. The mixture was stirred in an ice bath for 30 minutes and at room temperature for another 30 minutes, then distilled on rotavap. To the oily residue, 50 ml of dichloromethane were added and then distilled on rotavap. This process was repeated three times to obtain a pale grayish solid froth. To the solid, 50 ml of anhydrous ether were added and the solid obtained was filtered, washed with ether and dried to give 4.17 g (97.2% yield) of product, mp 215°–218° C. NMR (CDCl$_3$) δ0.80–2.87 (m, 51H, cholest. and Leu protons); 3.30–3.60 (m, 1H, (CH$_3$)$_2$—C$\underline{H}$); 3.88 (t, 1H, Leu CH$_2$—C$\underline{H}$); 4.60–4.80 (m, 1H, cholest. O—C$\underline{H}$; 5.35 (bd, 1H, cholest.=C$\underline{H}$); 7.2–8.1 (hump, 3H, N⁺H$_3$, disappear on addition of D$_2$O).

EXAMPLE 57

Preparation of N-t-Boc-Phe-D-Leu-Cholesteryl Ester (57):

To a stirred ice cold suspension of 3.17 g (5.16 mmol) of compound (56) in 50 ml of dichloromethane, 0.52 g (0.72 ml, 5.16 mmol) of triethylamine was added. To the clear mixture, 0.69 g (5.16 mmol) of 1-hydroxybenzotriazole (HOBt), 1.4 g (5.2 mmol) and 1.2 g (5.8 mmol) of DCC were added successively. The formed gel-like mixture was stirred in an ice bath for 30 minutes until the gel was broken up and a suspension was obtained. The mixture was stirred at room temperature for 20 hours, then a few drops of 20% solution of acetic acid in dichloromethane was added and stirring was continued for 15 more minutes. The mixture was filtered and the filtrate was washed successively, 3 times each, with 5% citric acid solution, 5% sodium bicarbonate solution and water. The organic extract was dried over anhydrous sodium sulfate and distilled on rotavap. The solid was chromatographed (silica gel column; CH$_2$Cl$_2$/ethyl acetate 10:0.75). The solid product obtained was dissolved in the least amount of CH$_2$Cl$_2$ and then methanol was added to separate 3.7 g of white crystalline solid of m.p. 170°–172° C. NMR (CDCl$_3$): New peaks appear to δ3.1 (d,2H,C$_6$H$_4$—C$\underline{H}_2$—CH); 7.20 (s,5H,C$_6$$\underline{H}_5$).

EXAMPLE 58

Preparation of N-t-Boc-Gly-Phe-D-Leu-Cholesteryl Ester (58):

To an ice cold solution of 3.5 g (4.68 mmol) of compound (57) in 50 ml of CH$_2$Cl$_2$ contained in a tared round bottomed (RB) flask, 15 ml of TFA were added. The mixture was stirred in an ice bath for 30 minutes and at room temperature for another 30 minutes and then distilled on rotavap. The residue was dissolved in 50 ml of CH$_2$Cl$_2$ and then dried on rotavap. This process was repeated three times until a solid froth was obtained. The flask was kept in a desiccator over KOH pellets under vacuum overnight and then weighed to determine free TFA in excess. To the solid, 50 ml of CH$_2$Cl$_2$ was added and the solution was cooled in an ice bath. To the stirred solution, an amount of TEA equivalent to the salt and TFA in excess, was added. To the mixture, 0.64 g (4.7 mmol) of HOBt, 0.82 g (4.7 mmol) of N-t-Boc-Gly-OH and 0.91 g (4.7 mmol) of DCC were added successively. The formed gel-like mixture was stirred for 2 hours in an ice bath, by which time the gel was broken up and a slurry formed instead. The mixture was stirred at room temperature for 20 hours, then a few drops of 20% solution of acetic acid in CH$_2$Cl$_2$ were added, the mixture was stirred for 15 more minutes and filtered. The filtrate was washed successively, 3 time each, with 5% citric acid solution, 5% sodium bicarbonate solution and water. The organic extract was dried over anhydrous sodium sulfate and distilled on rotavap. The crude solid product was dissolved in the least amount of CHCl$_3$ and methanol was added and the mixture was cooled to give 2.7 g (72% yield) of white crystalline solid, proved by TLC and NMR to be the pure product, m.p. 214°–216° C. NMR (CHCl$_3$) was very close to the spectrum of compound (57).

EXAMPLE 59

Preparation of [SEQ ID NO. 76] N-t-Boc-D-Ala-Gly-Phe-D-Leu-Cholesteryl Ester (59):

To an ice cold suspension of 2.5 g (3.10 mmol) of compound (58) in 50 ml of CH$_2$Cl$_2$ contained in a tared round bottomed flask, 15 ml of TFA were added. The mixture was stirred in an ice bath for 30 minutes and at room temperature for another 30 minutes and then distilled on rotavap. The residue was dissolved in 50 ml of CH$_2$Cl$_2$ and then dried on rotavap. This process was repeated three times until a solid froth was obtained. The flask was kept in a desiccator over KOH pellets under vacuum overnight and then weighed to determine free TFA in excess. To the solid, 50 ml of CH$_2$Cl$_2$ were added and the solution was cooled in an ice bath. To the stirred solution, an amount of TEA equivalent to the salt and TFA in excess, was added. To the mixture, 0.43 g (3.2 mmol) of HOBt, 0.61 g (3.22 mmol) of N-t-Boc-D-Ala-OH and 0.66 g (3.2 mmol) of DCC were added successively. The formed thick, gel-like mixture was stirred for 2 hours in an ice bath until the gel was broken up and a slurry formed instead. The mixture was stirred at room temperature for 20 hours, then a few drops of a 20% solution of acetic acid in CH$_2$Cl$_2$ were added, stirred for 15 more minutes and filtered. The filtrate was washed successively, 3 times each, with 5% citric acid solution, 5% sodium bicarbonate solution and water. The organic extract was dried over anhydrous sodium sulfate and distilled on rotavap. The crude product was chromatographed (silica gel column, CHCl$_3$/ethyl acetate 1:1) to give 1.9 g (70% yield) of solid pure compound of m.p. 175°–180° C. (dec.), proved by NMR to be the desired compound.

EXAMPLE 60

Preparation of [SEQ ID NO. 77] N-t-Boc-Tyr-D-Ala-Gly-Phe-D-Leu-Cholesteryl Ester (60):

To an ice cold suspension of 1.5 g (1.71 mmol) of compound (59) [SEQ ID NO. 76] in 50 ml of CH$_2$Cl$_2$ contained in a tared RB flask, 15 ml of TFA were added. The mixture was stirred in an ice bath for 30 minutes and at room temperature for another 30 minutes, then distilled on rotavap. The residue was dissolved in 50 ml of CH$_2$Cl$_2$ and then dried on rotavap. This process was repeated three times, at which point a grayish solid froth was obtained. The flask was kept in a desiccator over KOH pellets under vacuum overnight and then weighed to determine free TFA in excess. To the solid, 100of CHCl$_3$ were added and the solution was cooled in an ice bath. To the stirred solution, an amount of TEA equivalent to the salt and TFA in excess was added. To the mixture, 0.24 g (1.8 mmol) of HOBt, 0.51 g (1.8 mmol) of N-t-Boc-Tyr-OH and 0.37 g (1.8 mmol) of DCC were added successively. The mixture was stirred for 1 hour in an ice bath and at room temperature for 20 hours, then a few drops of a 20% solution of acetic acid in $CH_2Cl_2$ were added, stirred for 15 more minutes and filtered. The filtrate was washed successively, 3 times each, with 5% citric acid solution, 5% sodium bicarbonate solution and water. The organic extract was dried over anhydrous sodium sulfate and distilled on rotavap. The crude product was chromatographed (silica gel column, $CHCl_3$/ethyl acetate 1:1) when 1.59 g (90% yield) of solid pure compound was obtained. NMR confirmed this to be the desired compound. NMR ($CDCl_3$): In addition to the usual peaks of compound (59), a typical AA'XX' system appeared at δ 6.75–7.05 integrated for 4H (p-$C_6H_4$ of Tyr).

EXAMPLE 61

Preparation of [SEQ ID NO. 78] N-t-Boc-Ala-Tyr-D-Ala-Gly-Phe-D-Leu-Cholesteryl Ester (61):

To an ice cold suspension of 1.5 g (1.44 mmol) of compound (60) [SEQ ID NO. 77] in 50 ml of $CH_2Cl_2$ contained in a tared RB flask, 15 ml of TFA was added. The mixture was stirred in an ice bath for 30 minutes and at room temperature for another 30 minutes, then distilled on rotavap. The residue was dissolved in 50 ml of $CH_2Cl_2$ and then dried on rotavap. This process was repeated three times to afford a yellowish solid froth. The flask was kept in a desiccator over KOH pellets under vacuum overnight and then weighed to determine free TFA in excess. To the solid, 100 ml of $CH_2Cl_2$ was added and the solution was cooled in an ice bath. To the stirred solution, an amount of TEA equivalent to the salt and TFA in excess, was added. To the mixture, 0.20 g (1.5 mmol) of HOBt, 0.28 g (1.5 mmol) of N-t-Boc-Ala-OH and 0.31 g (1.5 mmol) of DCC were added successively. The mixture was stirred for 30 minutes in ice bath and at room temperature for 20 hours, then a few drops of a 20% solution of acetic acid in $CH_2Cl_2$ were added, stirred for 15 more minutes and filtered. To the filtrate, 100 ml of $CHCl_3$ were added and the mixture was washed successively, 3 times each, with 5% citric acid solution, 5% sodium bicarbonate solution and water. The organic extract was dried over anhydrous sodium sulfate and distilled on rotavap. The crude product was chromatographed (silica gel column, $CHCl_3$/ethyl acetate/$CH_3OH$ 5:10:0.5) to give 1.3 g (81% yield) of solid pure compound, m.p. 187°–190° C. (dec.). NMR confirmed this to be the desired compound.

EXAMPLE 62

Preparation of [SEQ ID NO. 79] Nicotinoyl-Ala-Tyr-D-Ala-Gly-Phe-D-Leu-Cholesteryl Ester (62):

To an ice cold suspension of 1.2 g (1.1 mmol) of compound (61) [SEQ ID NO. 78] in 25 ml of $CH_2Cl_2$ contained in a tared RB flask, 15 ml of TFA were added. The mixture was stirred in an ice bath for 30 minutes and at room temperature for another 30 minutes, then distilled on rotavap. The residue was dissolved in 25 ml of $CH_2Cl_2$ and then dried on rotavap. This process was repeated three times to give a solid froth. The flask was kept in a desiccator over KOH pellets under vacuum overnight and then weighed to determine free TFA in excess. To the solid, 15 ml of DMF and 25 ml of $CHCl_3$ were added and the solution was cooled in an ice bath. To the stirred solution, an amount of TEA equivalent to the salt and TFA in excess, was added. To the mixture, 0.16 g (1.2 mmol) of HOBt, 0.15 g (1.2 mmol) of nicotinic acid and 0.25 g (1.2 mmol) of DCC were added successively. The mixture was stirred for 30 minutes in an ice bath and at room temperature for 24 hours. Most of the solvent was then distilled off on rotavap. To the residue, 50 ml of saturated sodium chloride solution was added while stirring. The white gritty solid which separated was removed by filtration, triturated well and washed successively, 3 times each, with 5% citric acid solution, 5% sodium bicarbonate solution and water. The solid was then dried in a desiccator over $P_2O_5$. The crude product was chromatographed (silica gel column, 10% $CH_3OH$ in $CHCl_3$, to afford 0.9 g (75% yield) of solid pure compound.

EXAMPLE 63

Preparation of [SEQ ID NO. 80] Trigonellyl-Ala-Tyr-D-Ala-Gly-Phe-D-Leu-Cholesteryl Ester Methylsulfate (63):

To a solution of 0.8 g (0.7 mmol) of compound (62) [SEQ ID NO. 79] in 15 ml of DMF, 1 ml of dimethylsulfate was added. The mixture was stirred at room temperature for 24 hours. Most of the solvent was then distilled on rotavap and 25 ml of anhydrous ether were added to the residue. The sticky solid which separated was then dissolved in the least amount of methanol and precipitated with anhydrous ether. The process was repeated several times and the solid was then filtered and dried in a vacuum desiccator over $P_2O_5$ to give 0.6 g (68.5% yield). Electrospray MS proved the sample was sufficiently pure to prepare the corresponding 1,4-dihydropyridine derivative. Sample for microanalysis was prepared by double recrystallization from ethanol. UV ($CH_3OH$) $\gamma_{max}$269 nm, ($E^{1\%}{}_{1\ cm}$=44.6). Microanalysis calculated for $C_{66}H_{94}N_7O_9^+ \cdot CH_3SO_4^-$: C% 64.86, H% 7.88, N% 7.90, S% 2.58. Found: C% 64.13, H% 7.90, N% 8.01, S% 2.47.

The quaternary product (63) has the structural formula [SEQ ID NO. 80]

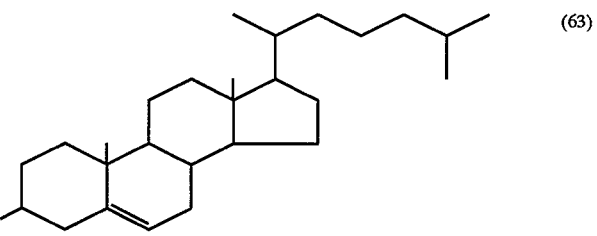

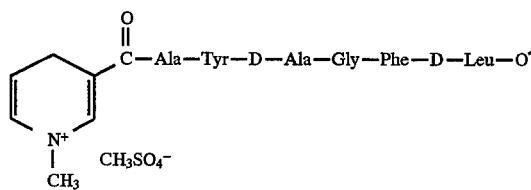

EXAMPLE 64

Preparation of [SEQ ID NO. 81] 1,4-Dihydrotrigonellyl-Ala-Tyr-D-Ala-Gly-Phe-D-Leu-Cholesteryl Ester (64):

To an ice cold solution of 0.62 g (0.5 mmol) of compound (63) [SEQ ID NO. 80] in 100 ml of 50% aqueous methanol, 0.37 g (4.4 mmol) of sodium bicarbonate and 0.52 g (3 mmol) of sodium dithionite were added slowly while stirring. The mixture was kept ice cold and under nitrogen while stirring for 2 hours. To the cold mixture, 100 ml of water and 100 ml of chloroform were added and stirring was continued for 30 minutes longer. The chloroform layer was then separated and the aqueous layer was reextracted with 50 ml of chloroform. The combined chloroform extracts were washed with cold water, dried over anhydrous magnesium sulfate and distilled on rotavap to give 0.4 g (70.8% yield) of (64) as a yellow solid. MS (electrospray) M$^+$=1129, UV (CH$_3$OH) 275 nm (E$^{1\%}_{1\,cm}$=27.15) 360 nm (E$^{1\%}_{1\,cm}$=12.93) with a ratio of A$_{275}$/A$_{360}$=2.1. Methanol solution of the product reduced alcoholic silver nitrate solution slowly at room temperature and the supernatant obtained on centrifugation showed the UV spectrum of the corresponding quaternary derivative.

The product (64) has the structural formula [SEQ ID NO. 81]

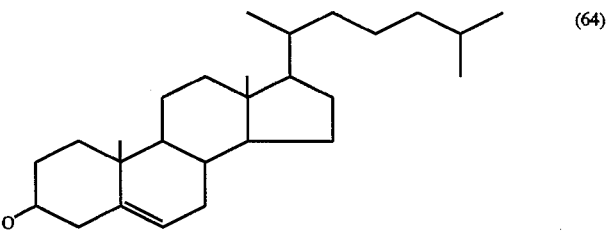

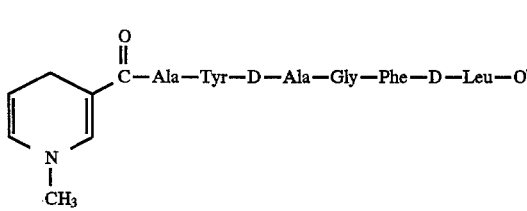

EXAMPLE 65

Preparation of [SEQ ID NO. 82] H-Tyr-D-Ala-Gly-Phe-D-Leu-Cholesteryl Ester (65):

To an ice cold solution of 0.6 g (5.7 mmol) of compound (60) [SEQ ID NO. 77] in 20 ml of methylene chloride, 9 ml of TFA were added. The mixture was stirred for 30 minutes at 0° C. and for 30 minutes at room temperature. The mixture was then distilled on rotavap, 20 ml of methylene chloride were added to the residue, the mixture was redistilled and the process was repeated three times. The semisolid residue was washed three times, each time with 30 ml of anhydrous ether. The white crystalline powder thus obtained was checked for purity with electrospray mass spectrometry. The solid was dissolved in 20 ml of chloroform, cooled in an ice bath and 0.1 ml of TEA was dropped into the solution while stirring. The mixture was washed with cold water and the organic layer was dried over anhydrous magnesium sulfate, then distilled on rotavap and dried in a vacuum desiccator. The white solid was proved by MS to be the pure product (65) [SEQ ID NO. 82].

EXAMPLE 66

Preparation of [SEQ ID NO. 83] N-t-Boc-Ala-Ala-Tyr-D-Ala-Gly-Phe-D-Leu-Cholesteryl Ester (66):

To an ice cold solution of 3.6 g (3.4 mmol) of compound (61) [SEQ ID NO. 78] in a tared flask in 50 ml of CH$_2$Cl$_2$, 25 ml of TFA were added. The mixture was stirred at 0° C. for 30 minutes and at room temperature for another 30 minutes. The mixture was distilled on rotavap, 50 ml of CH$_2$Cl$_2$ were added to the residue, and the mixture was distilled, and the process was repeated three times. The flask was weighed and the amount of TFA retained with the grayish white solid was calculated. To the solid, 100 ml of dry DMF were added and the mixture was cooled in an ice bath. To the stirred mixture, an mount of TEA equivalent to the excess TFA and the salt was dropped, followed by addition of 0.90 g (6.6 mmol) HOBt, 1.28 (6.8 mmol) N-t-Boc-Ala-OH and 1.6 g (7.8 mmol) DCC. Stirring was continued at room temperature for 48 hours. The mixture was then filtered and the filtrate was concentrated to half its volume, cooled and filtered. The filtrate was distilled on rotavap to dryness. The solid residue thus obtained was washed on a Büchner funnel with 5% citric acid solution and 5% sodium bicarbonate solution, three times each, then with water. The dried solid was shown by MS to contain a small mount of DCU as an impurity in addition to the desired product (66) [SEQ ID NO. 83] and was used as such for the next step.

EXAMPLE 67

Preparation of Nicotinoyl-Ala-Ala-Tyr-D-Ala-Gly-Phe-D-Leu-Cholesteryl Ester (67):

To an ice cold suspension of 1.7 g (1.4 mmol) of compound (66) [SEQ ID NO. 83] in 25 ml of CH$_2$Cl$_2$ contained in a tared flask, 15 ml of TFA were added. The mixture was stirred at 0° C. for 30 minutes and at room temperature for another 30 minutes, then the mixture was distilled on rotavap. To the reddish viscous liquid, 25 ml of CH$_2$Cl$_2$ was added, the mixture was distilled and the process was repeated three times. The flask was weighed and the mount of TFA retained was calculated. To the grayish solid, 50 ml of DMF were added, cooled in ice bath, and an mount of TEA equivalent to the retained TFA and the salt was added. To the cooled stirred mixture, 0.19 g (1.4 mmol) of HOBt, 0.17 g (1.4 mmol) of nicotinic acid and 0.29 g (1.4 mmol) of DCC were added. The mixture was kept stirring at room temperature for 36 hours, then filtered. The filtrate was distilled and the residue was washed well with water, 5% citric acid solution, 5% sodium bicarbonate solution and finally with water. The solid was dried and then chromatographed on silica gel using 10% CH$_3$OH in CHCl$_3$ as eluent. The solids separated from the second fraction proved by MS to contain a very small amount of dinicotinoyl derivative which could be separated by chromatography on silica using 7% CH$_3$OH in CHCl$_3$ and eluting at slow rate, to give the desired product (67) [SEQ ID NO. 84].

EXAMPLE 68

Preparation of [SEQ ID NO. 85] Trigonellyl-Ala-Ala-Tyr-D-Ala-Gly-Phe-D-Leu-Cholesteryl Ester Methylsulfate (6):

To a solution of 1.6 g (1.2 mmol) of compound (67) [SEQ ID NO. 84] in 30 ml of DMF, 2 ml of dimethylsulfate were added. The mixture was stirred at room temperature for 24 hours. Most of the solvent was then distilled on rotavap and 50 ml of anhydrous ether were added to the residue. The sticky solid which separated was then dissolved in the least amount of methanol and precipitated with about 100 ml of anhydrous ether. Ether was then decanted from the jelly mass and the process was repeated several times. The resultant solid was then separated by filtration and dried in a vacuum desiccator over $P_2O_5$ to give 1.0 g (63.5% yield). Electrospray MS proved the sample was sufficiently pure to prepare the corresponding 1,4-dihydropyridine derivative. UV $(CH_3OH)_{max}$275 nm.

The product (68) has the structural formula [SEQ ID NO. 85]

reduced alcoholic silver nitrate solution slowly at room temperature. The supernatant obtained on centrifugation showed the UV spectrum of the corresponding quaternary derivative. Obtained in this manner was compound (69), which has the structural formula [SEQ ID NO. 86]

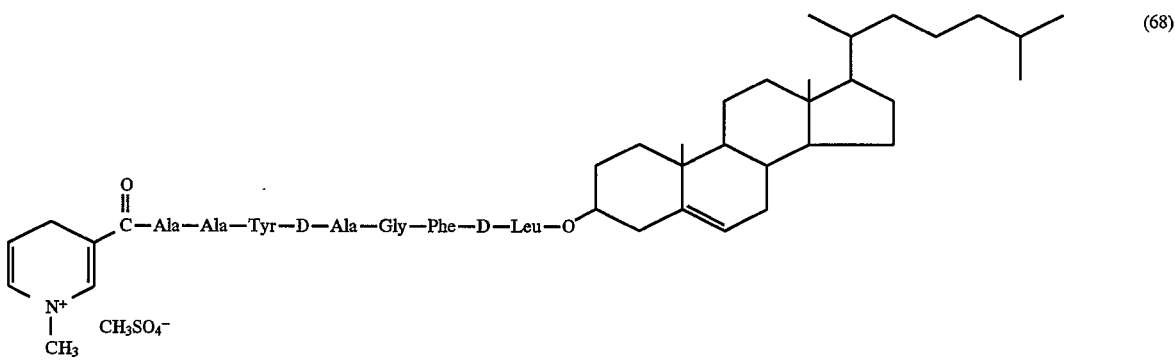

EXAMPLE 69

Preparation of [SEQ ID NO. 86] 1,4Dihydrotrigonellyl-Ala-Ala-Tyr-D-Ala-Gly-Phe-D-Leu-Cholesteryl Ester (69):

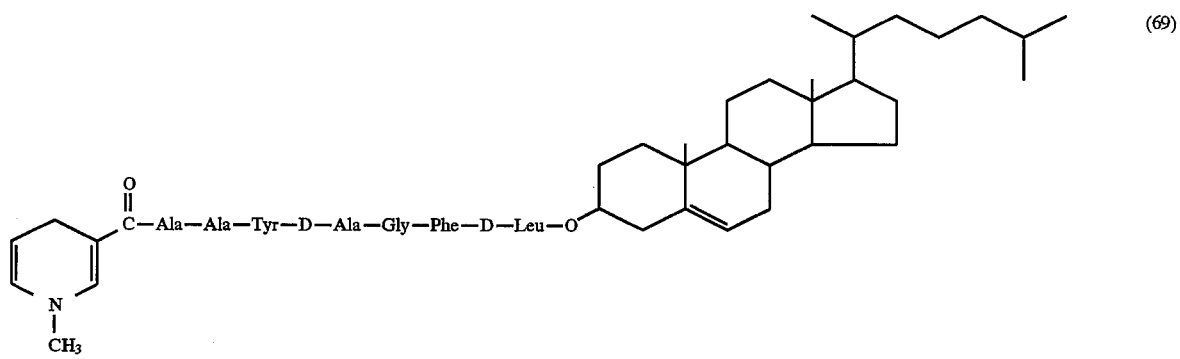

To an ice cold solution of 0.70 g (0.5 mmol) of compound (68) [SEQ ID NO. 85] in 100 ml of 40% aqueous methanol, 0.44 g (5.2 mmol) of sodium bicarbonate and 0.9 g (5.2 mmol) of sodium dithionite were added slowly while stirring. The mixture was kept ice cold and under nitrogen while stirring for 2 hours. To the cold mixture, 100 ml of water and 100 ml of chloroform were added and stirring was continued for one more hour. The thick emulsion which resulted was filtered through a sintered glass funnel and chloroform was then removed by distillation on rotavap at 20° C., from the thick filtrate. The fine yellow solid which separated was removed from the aqueous mixture by filtration, washed with pure deaerated water several times, then washed once with methanol and dried in a desiccator to give 0.4 g (66% yield) of fine yellow solid. MS (electrospray) $M^+$=1129, UV $(CH_3OH)$ 265 nm, 358 nm. $CH_3OH$ solution of the product

EXAMPLE 70

Preparation of [SEQ ID NO. 87] Trigonellyl-Ala-Tyr-D-Ala-Gly-Phe-D-Leu-OH Methylsulfate (70):

To an ice cold suspension of 1.0 g (0.8 mmol) of compound (63) [SEQ ID NO. 80] in 50 ml of THF, a solution of 64 mg (1.6 mmol) of NaOH in 2 ml of water was added. The mixture was stirred at 0° C. for 4 hours. The yellowish solution was distilled on rotavap at low temperature and the solid yellow residue was extracted thoroughly with 50 ml of water and filtered. The filtrate was cooled, acidified with dilute HCl to pH 3–4, filtered and then freeze dried. The solid was extracted with DMF and filtered. The filtrate was distilled under vacuum and the residue was washed several times with anhydrous ether and dried to give 0.35 (57% yield) of yellowish solid which was proved by MS to be the pure compound (70).

EXAMPLE 71

Preparation of [SEQ ID NO. 88] Trigonellyl-Ala-Ala-Tyr-D-Ala-Gly-Phe-D-Leu-OH Methylsulfate (71):

To an ice cold suspension of 0.5 g (0.4 mmol) of compound (68) [SEQ ID NO. 85] in 25 ml of THF, a solution of 32 mg (0.8 mmol) of NaOH in 2 ml of water was added. The mixture was stirred at 0° C. for 4 hours. The yellowish solution was distilled on rotavap at low temperature and the solid yellow residue was extracted thoroughly with 50 ml of water and filtered. The filtrate was cooled, acidified with dilute HCl to pH 3–4, filtered and then freeze dried. The solid was extracted with DMF and filtered. The filtrate was distilled under vacuum and the residue was washed well with ether and dried to give 0.15 g (39.7% yield) of yellowish solid which was proved by MS to be the pure compound (71) [SEQ ID NO. 88].

EXAMPLE 72

Preparation of [SEQ ID NO. 89] Trigonellyl-Ala-Tyr-D-Ala-Gly-Phe-D-Leu-Ethyl Ester Methylsulfate (72):

To a solution of 0.6 g (0.68 mmol) of compound (70) [SEQ ID NO. 87] in 10 ml of absolute ethanol, 2 ml of THF were added. The mixture was refluxed overnight and then distilled on rotavap. The residue was washed well with anhydrous ether and dried to give 0.4 g (65% yield) of yellowish white highly hygroscopic powder which was proved by MS to be the desired compound (72) [SEQ ID NO. 89].

EXAMPLE 73

Preparation of [SEQ ID NO. 90] 1,4-dihydrotrigonellyl-Ala-Tyr-D-Ala-Gly-Phe-D-Leu-Ethyl Ester (73):

To an ice cold solution of 0.4 g (0.44 mmol) of compound (72) [SEQ ID NO. 89] in 100 ml of 25% aqueous methanol, 0.37 g (4.4 mmol) of sodium bicarbonate and 0.52 g (3 mmol) of sodium dithionite were added slowly while stirring. The mixture was kept ice cold and under nitrogen while stirring for 2 hours. To the cold mixture, 100 ml of water and 100 ml of chloroform were added and stirring was continued for 30 minutes longer. Chloroform was then removed by distillation from the thick emulsion formed, on rotavap at 20° C. The fine yellow solid which separated was removed by filtration, washed well with water and dried in a vacuum desiccator to give 0.25 g (72% yield) of (73) as a yellow solid. MS (electrospray) M+=812, UV (CH₃OH) 270 nm (shoulder), 358 nm. Methanol solution of the product reduced alcoholic silver nitrate solution slowly at room temperature.

EXAMPLE 74

Preparation of [SEQ ID NO. 91] 1,4-Dihydrotrigonellyl-Ala-Tyr-D-Ala-Gly-Phe-D-Leu-OH (74):

To an ice cold solution of 0.5 g (0.53 mmol) of compound (70) [SEQ ID NO. 87] in 100 ml of water, 0.4 g (4.7 mmol) of sodium bicarbonate and 0.82 g (4.4 mmol) of sodium dithionite were added slowly while stirring. The mixture was kept ice cold and under nitrogen while stirring for 2 hours. To the cold mixture, 50 ml of chloroform were added and stirring was continued for 30 minutes longer. The chloroform layer was then separated, washed with water, dried over anhydrous magnesium sulfate and distilled to give 0.1 g (25% yield) of compound (74) [SEQ ID NO. 91] as a fine yellow solid. Methanol solution of (74) [SEQ ID NO. 91] reduced alcoholic silver nitrate solution slowly at room temperature.

EXAMPLE 75

Preparation of [SEQ ID NO. 92] N-t-Boc-Pro-Tyr-D-Ala-Gly-Phe-D-Leu-Cholesteryl Ester (75):

The title compound is prepared by repeating the procedure of EXAMPLE 61, but using an equivalent quantity of N-t-Boc-Pro-OH in place of the N-t-Boc-Ala-OH utilized therein.

EXAMPLE 76

Preparation of [SEQ ID NO. 93] Nicotinoyl-Pro-Tyr-D-Ala-Gly-Phe-D-Leu-Cholesteryl Ester (76):

Repetition of the procedure of EXAMPLE 62 using an equivalent quantity of compound (75) [SEQ ID NO. 92] in place of compound (61) [SEQ ID NO. 78] therein affords the title compound.

EXAMPLE 77

Preparation of [SEQ ID NO. 94] Trigonellyl-Pro-Tyr-D-Ala-Gly-Phe-D-Leu-Cholesteryl Ester Methylsulfate (77):

The procedure of EXAMPLE 63 is repeated, except that an equivalent quantity of compound (76) [SEQ ID NO. 93] is used in place of compound (62) [SEQ ID NO. 79], to afford the quaternary derivative (77) [SEQ ID NO. 94].

EXAMPLE 78

Preparation of [SEQ ID NO. 95] 1,4-Dihydrotrigonellyl-Pro-Tyr-D-Ala-Gly-Phe-D-Leu-Cholesteryl Ester (78):

Using the procedure of EXAMPLE 64, but substituting an equivalent quantity of compound (77) [SEQ ID NO. 94] for the compound (63) [SEQ ID NO. 80] employed therein, affords the title compound having the formula

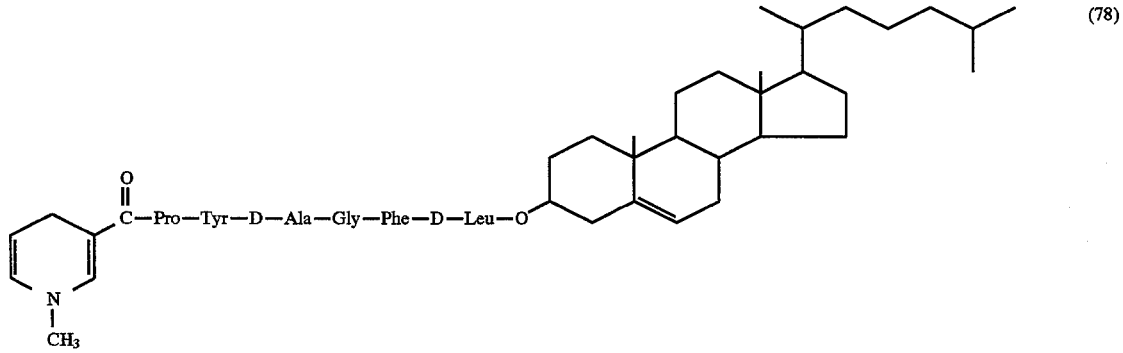

EXAMPLE 79

Preparation of [SEQ ID NO. 96] N-t-Boc-Ala-Pro-Tyr-D-Ala-Gly-Phe-D-Leu-Cholesteryl Ester (79):

The title compound is prepared by repeating the procedure of EXAMPLE 66, but using an equivalent quantity of compound (75) [SEQ ID NO. 92] in place of compound (61) [SEQ ID NO. 78] therein.

EXAMPLE 80

Preparation of [SEQ ID NO. 97] Nicotinoyl-Ala-Pro-Tyr-D-Ala-Gly-Phe-D-Leu-Cholesteryl Ester (80):

Repetition of the procedure of EXAMPLE 67 using an equivalent quantity of compound (79) [SEQ ID NO. 96] in place of compound (66) [SEQ ID NO. 83] therein affords the title compound.

EXAMPLE 81

Preparation of [SEQ ID NO. 98] Trigonellyl-Ala-Pro-Tyr-D-Ala-Gly-Phe-D-Leu-Cholesteryl Ester Methylsulfate (81):

The procedure of EXAMPLE 68 is repeated, except that an equivalent quantity of compound (80) [SEQ ID NO. 97] is used in place of compound (67) [SEQ ID NO. 87], to afford the quaternary derivative (81) [SEQ ID NO. 98].

EXAMPLE 82

Preparation of [SEQ ID NO. 99] 1,4-Dihydrotrigonellyl-Ala-Pro-Tyr-D-Ala-Gly-Phe-D-Leu-Cholesteryl Ester (82):

Using the procedure of EXAMPLE 69, but substituting an equivalent quantity of compound (81) [SEQ ID NO. 98] for the compound (68) [SEQ ID NO. 85] employed therein, affords the title compound having the formula The title compound is prepared by repeating the procedure of EXAMPLE 66, but using an equivalent quantity of compound (75) [SEQ ID NO. 92] in place of compound (61) [SEQ ID NO. 78] and an equivalent quantity of N-t-Boc-Pro-OH in place of the N-t-Boc-Ala-OH utilized therein.

EXAMPLE 84

Preparation of [SEQ ID NO. 101] Nicotinoyl-Pro-Pro-Tyr-D-Ala-Gly-Phe-D-Leu-Cholesteryl Ester (84):

Repetition of the procedure of EXAMPLE 67 using an equivalent quantity of compound (83) [SEQ ID NO. 100] in place of compound (66) [SEQ ID NO. 83] therein affords the title compound.

EXAMPLE 85

Preparation of [SEQ ID NO. 102] Trigonellyl-Pro-Pro-Tyr-D-Ala-Gly-Phe-D-Leu-Cholesteryl Ester Methylsulfate (85):

The procedure of EXAMPLE 68 is repeated, except that an equivalent quantity of compound (84) [SEQ ID NO. 101] is used in place of compound (67) [SEQ ID NO. 84], to afford the quaternary derivative (85) [SEQ ID NO. 102].

EXAMPLE 86

Preparation of [SEQ ID NO. 103] 1,4-Dihydrotrigonellyl-Pro-Pro-Tyr-D-Ala-Gly-Phe-D-Leu-Cholesteryl Ester (86):

Using the procedure of EXAMPLE 69, but substituting an equivalent quantity of compound (85) [SEQ ID NO. 102] for the compound (68) [SEQ ID NO. 85] employed therein, affords the title compound having the formula

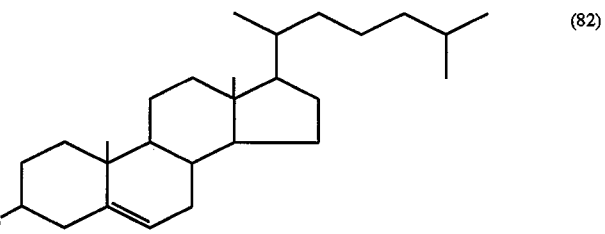
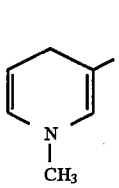

(82)

EXAMPLE 83

Preparation of [SEQ ID NO. 100] N-t-Boc-Pro-Pro-Tyr-D-Ala-Gly-Phe-D-Leu-Cholesteryl Ester (83):

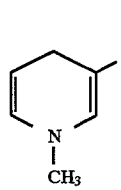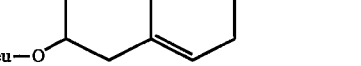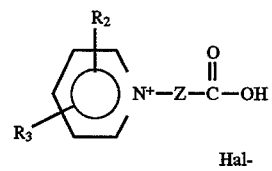

(86)

EXAMPLE 87

Preparation of [SEQ ID NO. 104] N-t-Boc-Pro-Ala-Tyr-D-Ala-Gly-Phe-D-Leu-Cholesteryl Ester, (87):

The title compound is prepared by repeating the procedure of EXAMPLE 66, but using an equivalent quantity of N-t-Boc-Pro-OH in place of the N-t-Boc-Ala-OH utilized therein.

EXAMPLE 88

Preparation of [SEQ ID NO. 105] Nicotinoyl-Pro-Ala-Tyr-D-Ala-Gly-Phe-D-Leu-Cholesteryl Ester (88):

Repetition of the procedure of EXAMPLE 67 using an equivalent quantity of compound (87) [SEQ ID NO. 104] in place of compound (66) [SEQ ID NO. 83] therein affords the title compound.

EXAMPLE 89

Preparation of [SEQ ID NO. 106] Trigonellyl-Pro-Ala-Tyr-D-Ala-Gly-Phe-D-Leu-Cholesteryl Ester Methylsulfate (89):

The procedure of EXAMPLE 68 is repeated, except that an equivalent quantity of compound (88) [SEQ ID NO. 105] is used in place of compound (67) [SEQ ID NO. 84], to afford the quaternary derivative (89) [SEQ ID NO. 106].

EXAMPLE 90

Preparation of [SEQ ID NO. 107] 1,4-Dihydrotrigonellyl-Pro-Ala-Tyr-D-Ala-Gly-Phe-D-Leu-Cholesteryl Ester (90):

Using the procedure of EXAMPLE 69, but substituting an equivalent quantity of compound (89) [SEQ ID NO. 106] for the compound (68) [SEQ ID NO. 85] employed therein, affords the title compound having the formula The foregoing EXAMPLES illustrate the preparation of a variety of representative compounds of formula (I) and intermediates thereto. Many modifications in these methods may be utilized, including use of a peptide synthesizer, variations in protecting groups for the various functional groups used to build the peptide sequence, variations in solvents, reaction conditions, and of course variations in the reactants containing the redox moiety or the bulky ester group —$OR_4$, in the spacer and in the pharmacologically active peptide.

Especially desirable alternates for the nicotinic acid reactant, used to introduce alternate redox moieties into the compounds of formula (I), include isonicotinic acid, picolinic acid, 4-isoquinolinecarboxylic acid, 3-quinolinecarboxylic acid, 4-quinolinecarboxylic acid, and substituted derivatives of these compounds or of nicotinic acid, as well as the corresponding reactants of the type

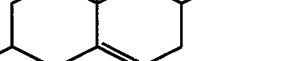

Hal-wherein Z is $C_1-C_6$ alkylene, $R_2$ and $R_3$ are as defined with formula (I) and Hal is halogen (e.g., I), and of course the corresponding quinoline and isoquinoline derivatives. Among the reactants of this second type, those in which Z is —$CH_2$— or —$CH_2CH_2$— and in which one of $R_2$ and $R_3$ is hydrogen and the other of $R_2$ and $R_3$ is $C_2-C_8$ alkanoyloxy (e.g., acetoxy), $C_2-C_8$ alkoxycarboxyl (e.g., ethoxycarboxyl), —CH=NOR''' wherein R''' is as defined with formula (I) (e.g. —CH=NOH) or —CONR'R''

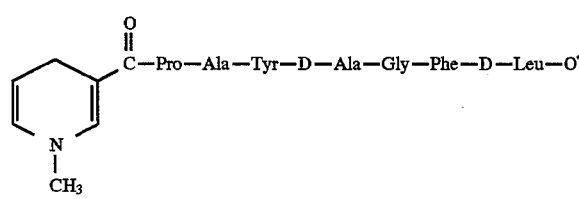

(90)

wherein R' and R" are as defined with formula (I) (e.g., —CONH₂) are preferred.

Especially desirable alternates for the N-protected-L-amino acids used to build the spacer portion of the compounds of formula (I) are the corresponding glycine and phenylalanine protected derivatives, used singly or combined with alanine and/or proline protected derivatives.

Especially desirable alternates for cholesterol, the alcohol (R₄OH) used to convert the carboxyl function of the C-terminal amino acid to the bulky esterified function are other sterols such as 3β-hydroxyandrostan-17-one, β-sitosterol and pregnane-3α,20-diol; fatty alcohols such as lauryl, myristyl, cetyl and stearyl alcohols and cyclic alcohols such as those depicted below:

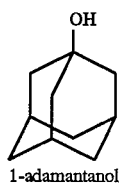
1-adamantanol

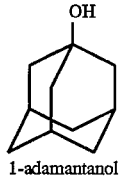
1-adamantanol

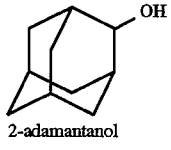
2-adamantanol

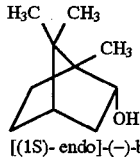
[(1S)- endo]-(–)-borneol

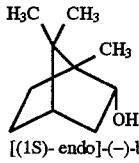
[(1S)- endo]-(–)-borneol

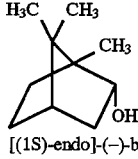
[(1S)-endo]-(–)-borneol

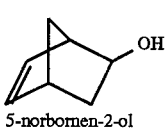
5-norbornen-2-ol

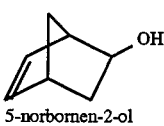
5-norbornen-2-ol

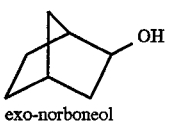
exo-norboneol

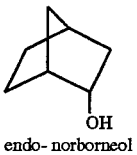
endo- norborneol

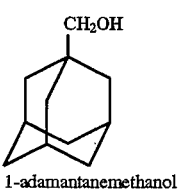
1-adamantanemethanol

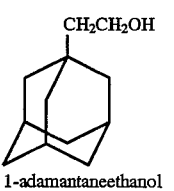
1-adamantaneethanol

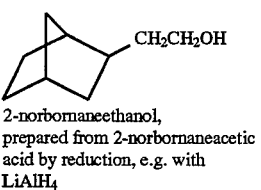
2-norbornaneethanol, prepared from 2-norbornaneacetic acid by reduction, e.g. with LiAlH₄

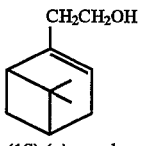
(1S)-(–)-nopol, or 6,6-dimethylbicyclo [3.1.1]-hept-2-ene-2-ethanol

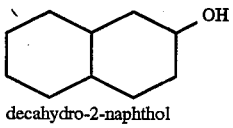
decahydro-2-naphthol

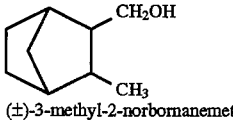
(±)-3-methyl-2-norbornanemethanol

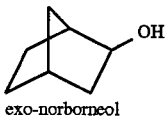
exo-norborneol

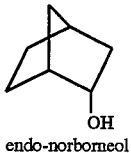
endo-norborneol

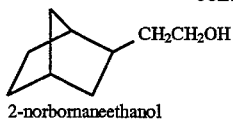

2-norbomaneethanol

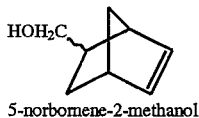

5-norbornene-2-methanol

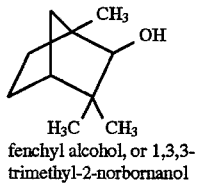

fenchyl alcohol, or 1,3,3-trimethyl-2-norbornanol

Variations in the amino acids used to build the pharmacologically active peptide portion of the compounds of formula (I) will be apparent from the discussion of such peptides earlier in this description. Peptides having useful effects on memory processes or depression and those useful in eliciting analgesia are of particular interest.

Representative peptide derivatives of formula (I) whose syntheses are detailed in the foregoing EXAMPLES have been found active in pharmacological testing, supporting the concept of "molecular packaging" for peptides in accord with the present invention. This testing is described in more detail below.

PHARMACOLOGICAL TESTING

Two representative chemical delivery systems (CDS's) of the invention for the TRH analog [Leu$^2$]-TRH, i.e., compound (8) of Scheme I/EXAMPLE 8, which has an alanine spacer, and compound (12) of Scheme II/Example 12, which has an alanine-alanine spacer, were studied for their effects on the barbiturate-induced sleeping time in mice. TRH is known to antagonize the reduction in cholinergic activity induced by barbiturates. Thus, the activational effects of the CDS's for TRH analogs on cholinergic neurons can be measured by quantitating the antagonism of pentobarbital-induced sleeping and barbiturate-induced reduction in cholinergic neuronal activity.

TRH was obtained from Bachera Inc. (Torrance, Calif.). [Leu$^2$]-TRH and two CDS's of [Leu$^2$]-TRH, Compound (8) (Ala spacer) and Compound (12) (Ala-Ala spacer) were synthesized as described hereinabove.

Swiss Webster mice weighing 30±2 g were used. The compounds were dissolved in a vehicle consisting of DMSO, ethanol and 50% (w/w) 2-hydroxypropyl-β-cyclodextrin at a ratio of 1:2:1 (15 mg/ml). CDS's at a dose of 30 mg/kg were injected in the animals through the tail vein. Vehicle only and an equimolar dose of TRH and [Leu$^2$]-TRH, 10 mg/kg, were also administered to compare CNS activities. Ten minutes after i.v. injection of the compound, each animal received an intraperitoneal injection of sodium methohexital solution (45 mg/ml) at a dose of 90 mg/kg. The sleeping time was recorded as the time elapsed from the onset of loss of the fighting reflex until the reflex was regained. Each compound and the vehicle control were tested on 5-11 animals. The statistical analysis was performed using the Student's t test.

Two experiments were carried out. Results are presented in Tables 1 and 2 below and in FIGS. 1 and 2. In Table 1, the effects of the CDS's were compared with that of [Leu$^2$]-TRH and vehicle control. The results indicate that compared to the control or [Leu$^2$]-TRH, the CDS's significantly decreased the barbiturate-induced sleeping time in mice. However, there was no significant difference between the control and [Leu$^2$]-TRH. A high incidence of death after the i.v. injection of vehicle or [Leu$^2$]-TRH was observed, but the reason is not fully understood. Therefore, the second experiment was done by comparing the sleeping time after the injection of vehicle control, TRH and [Leu$^2$]-TRH as shown in Table 2. The results indicate that the sleeping time was significantly reduced by [Leu$^2$]-TRH compared to TRH or vehicle control. No death occurred after the administration of vehicle or [Leu$^2$]-TRH, but 2 animals died after TRH. The behavior of animals after i.v. administration of each compound was observed. The vehicle inhibited the activity of the animals, but they recovered to normal within a few minutes. Animals after injection of TRH showed typical symptoms reported in the literature, such as tremor, tail-elevation and piloerection. After [Leu$^2$]-TRH, a few animals (1–2) showed the same symptoms as in the case of TRH. The CDS's did not induce the previous symptoms; the locomotor activity was, however, significantly increased.

Figure 2:
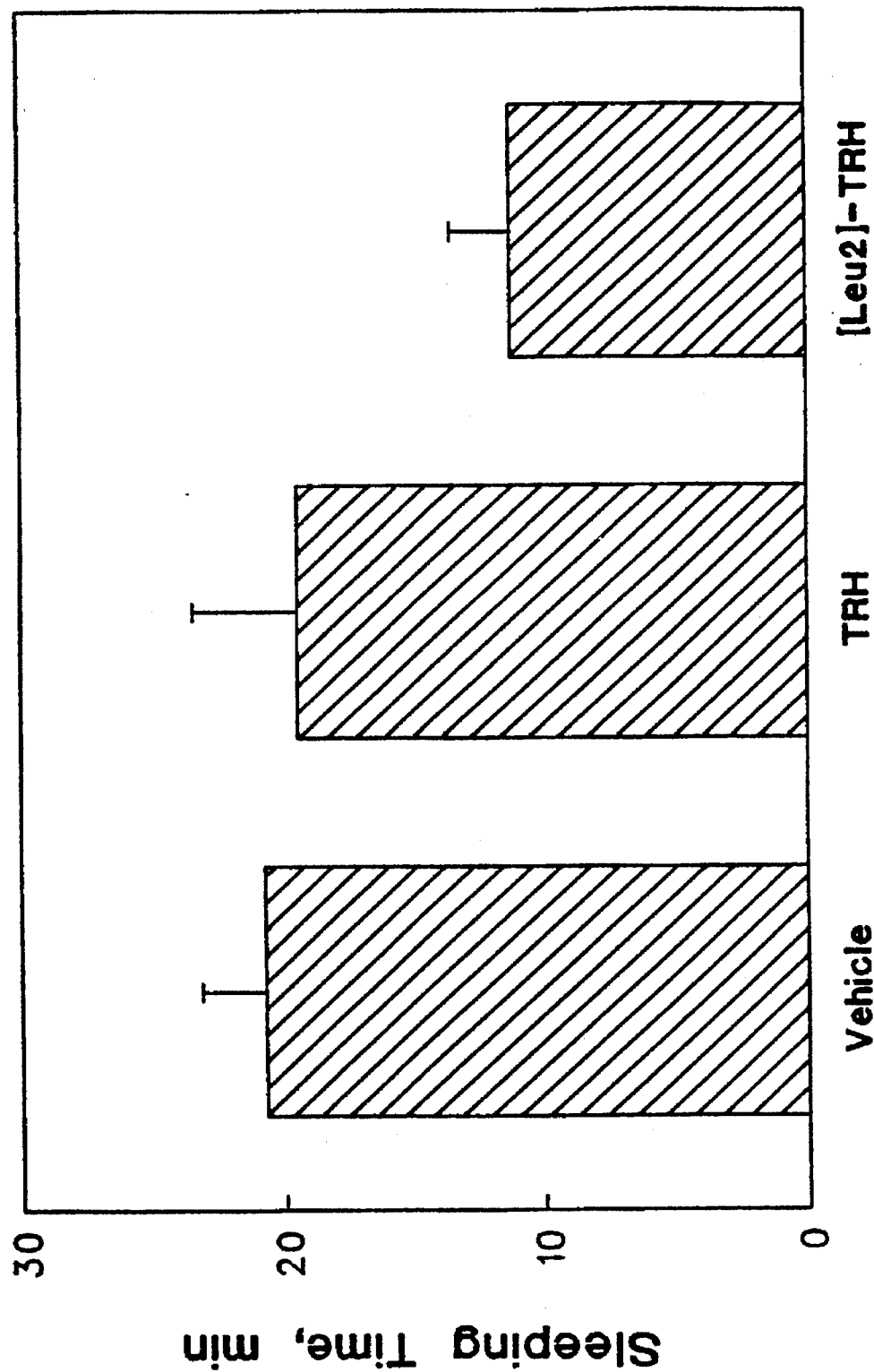
FIG. 2 is a bar graph depicting the effect on methohexital-induced sleeping time in mice in minutes for TRH, for the analog [Leu2]-TRH and for the vehicle following intravenous administration.

As is apparent from Table 1 and FIG. 1, the representative compounds of the invention markedly decreased sleeping time compared to the "unpackaged" TRH analog. The CDS having an alanine-alanine spacer was particularly active.

TABLE 1

A comparison of the methohexital induced sleeping time (in minutes) in mice after the administration of vehicle, TRH analog and the CDS's of the TRH analog.[1,2]

| Animal No. | Vehicle Control | [Leu$^2$]-TRH | CDS-A-[Leu$^2$]-TRH [Compound (8)] | CDS-AA-[Leu$^2$]-TRH [Compound (12)] |
|---|---|---|---|---|
| 1 | 41.95 | 33.95 | 18.23 | 12.08 |
| 2 | 34.23 | 37.37 | 15.33 | 17.18 |
| 3 | 22.06 | 28.22 | 11.90 | 27.05 |
| 4 | 19.97 | 15.03 | 17.27 | 10.07 |
| 5 | 19.35 | 33.63 | 46.07 | 16.40 |
| 6 | 31.60 | 20.90 | 18.58 | 19.00 |
| 7 | 47.38 | 27.97 | 15.73 | 8.13 |
| 8 | 26.57 | 36.80 | 34.43 | 15.38 |
| 9 | 31.50 | | 16.15 | 17.93 |
| 10 | 28.13 | | | 9.45 |
| 11 | 53.25 | | | |
| Mean | 32.36 | 29.23 | 21.52 | 15.27 |
| S.E. | 3.36 | 2.80 | 3.73 | 1.79 |
| p | | 0.40 | 0.042 | <0.001 |
| p* | | | 0.123 | 0.001 |
| No. of Death[2] | 5 | 5 | 2 | 1 |

[1]Table entries are the mean ± SE min.
[2]The sleeping time of the dead animals are not included in the table.
p Student's t-test compared to the control.
p* Student's t-test compared to [Leu$^2$]-TRH.

TABLE 2

Effect of [Leu$^2$]-TRH and TRH on the methohexital induced sleeping time (min) in mice.[1,2]

| Animal No. | Vehicle Control | TRH | [Leu$^2$]-TRH |
|---|---|---|---|
| 1 | 17.35 | 20.47 | 15.18 |
| 2 | 28.50 | 23.90 | 11.95 |
| 3 | 23.23 | 15.00 | 12.47 |

TABLE 2-continued

Effect of [Leu²]-TRH and TRH on the methohexital induced sleeping time (min) in mice.[1,2]

| Animal No. | Vehicle Control | TRH | [Leu²]-TRH |
|---|---|---|---|
| 4 | 14.25 | 12.90 | 11.17 |
| 5 | 20.18 | 11.17 | 8.53 |
| 6 |  | 11.77 | 8.02 |
| 7 |  | 40.82 |  |
| Mean | 20.70 | 19.43 | 11.22 |
| S.E. | 2.45 | 4.04 | 2.20 |
| p |  | 0.80 | 0.089 |
| P* |  |  | 0.004 |
| No. of Death² | 0 | 2 | 0 |

[1]Table entries are the mean ± SE min.
p Student's t-test compared to the control.
p* Student's t-test compared to TRH.

between each time point and control was defined as the change in tail flick latency. In the absence of response, a cut-off period of 1 minute was used. Each drug at each dose was tested in ten animals. Results are presented in Tables 5–8 below and in FIGS. 3–5. It is apparent from these Tables and Figures that a representative compound of the invention produced a very significant analgesic response for a prolonged period of time (at least 5 hours) while the "unpackaged" enkephalin, at an equimolar dose, did not differ from the control.

A representative chemical delivery system (A-CDS) of the invention for an enkephalin analog, H-Tyr-D-Ala-Gly-Phe-D-Leu-OH (also known as DADLE), namely compound (64) [SEQ ID NO. 81] of EXAMPLE 64, which has an alanine spacer, was studied in a rat tail flick test to determine its analgesic effects compared to DADLE itself.

Sprague-Dawley rats weighing 200–250 g were used. Drugs were dissolved in the vehicle consisting of DMSO, ethanol and 50% (w/w) 2-hydroxypropyl-β-cyclodextrin at a ratio of 1:2:1. A-CDS at a dose of 5 or 10 mg/2 ml/kg was injected in the animals through the tail vein. Vehicle only, or an equimolar dose (5 mg/kg) of DADLE (equimolar to 10 mg/kg of A-CDS) was also administered to compare the pharmacological activities. Tail flick latency, an index of spinal cord mediated analgesia, was measured before (control) and at 5 minutes, 15 minutes, 30 minutes, 1 hour, 2 hours, 3 hours, 4 hours, 5 hours and 6 hours after drug administration. The instrument used was a model 33 tail flick analgesia meter (lite, Inc., Landing, N.J.) set with the beam dial at 90 and the sensitivity at 8. Time between presentation of a focused beam of light and the reflexive removal of the tail from the stimulus was defined as the tail flick latency period, and the tail flick latency difference

TABLE 5

Tail flick latency periods in rats prior to and after i.v. administration of an enkephalin-CDS, enkephalin and vehicle[a,b]

| | Tail flick latency periods, seconds[c] | | | |
|---|---|---|---|---|
| Time, min | A-CDS [Compound (64)] (10)[d] | A-CDS [Compound (64)] (5) | Enkephalin [DADLE] (5) | Vehicle Control |
| 0[e] | 9.21 ± 0.53 | 7.24 ± 0.58 | 7.97 ± 0.60 | 8.23 ± 0.52 |
| 5 | 49.67 ± 4.67** | 25.95 ± 5.64 | 12.15 ± 1.53 | 15.16 ± 2.06 |
| 15 | 40.71 ± 7.00* | 20.63 ± 5.40 | 12.67 ± 1.18 | 15.93 ± 3.69 |
| 30 | 36.03 ± 6.34** | 14.22 ± 2.22 | 12.66 ± 1.70 | 10.43 ± 0.75 |
| 60 | 32.59 ± 6.63* | 13.00 ± 1.97 | 15.75 ± 3.03 | 10.32 ± 0.63 |
| 120 | 26.28 ± 4.56* | 18.37 ± 5.10 | 10.11 ± 1.29 | 11.24 ± 1.53 |
| 180 | 28.50 ± 4.40** | 16.63 ± 2.02* | 10.94 ± 1.65 | 9.51 ± 0.71 |
| 240 | 28.30 ± 4.68* | 20.28 ± 5.58 | 10.64 ± 1.68 | 12.61 ± 1.53 |
| 300 | 30.15 ± 3.81 | 17.84 ± 3.42 | 10.02 ± 1.08 | —[f] |

*Compared to the control group, $p < 0.01$; **$p < 0.005$ (by student's t-test). [a]Data represent mean ± S.E. of 9–10 rats. [b]Vehicle consisted of DMSO, ethanol and 50% (w/w) 2-hydroxypropyl-β-cyclodextrin at a ratio of 1:2:1. [c]The cut-off latency was 60 seconds. [d]Dose administered (mg/kg); A-CDS 10 mg is equimolar to enkephalin 5 mg. *Tail flick latency prior to drug administration. [f]Not determined.

TABLE 6

Number of animals responding to the treatment (in rat tail flick test)

| | Number of Animals | | | |
|---|---|---|---|---|
| Tail Flick Latency, seconds | A-CDS [Compound (64)] (10)[a] | A-CDS [Compound (64)] (5) | Enkephalin [DADLE] (5) | Vehicle Control |
| <20[b] | 0 | 4 | 7 | 7 |
| 20–40 | 1 | 2 | 3 | 2 |
| 40–60 | 3 | 2 | 0 | 0 |
| >60[c] | 6 | 2 | 0 | 0 |

[a]Dose administered (mg/kg/); A-CDS 10 mg is equimolar to enkephalin 5 mg.
[b]Maximum tail flick latency. [c]The cut-off latency was 60 seconds.

TABLE 7

Maximum tail flick latency in rats after i.v. administration of an enkephalin-CDS, enkephalin and vehicle[a,b,c]

| Treatment | Maximum tail flick latency, seconds |
|---|---|
| A-CDS (10)[d] [Compound (64)] | 51.94 ± 3.83* |
| A-CDS (5) [Compound (64)] | 33.05 ± 5.99** |
| Enkephalin (5) [DADLE] | 19.68 ± 2.42 |
| Vehicle Control | 19.61 ± 2.99 |

Compared to the control group, *p < 0.001 and **p < 0.07 (by student's t-test). [a]Data represent mean ± S.E. of 9–10 rats. [b]Vehicle consisted of DMSO, ethanol and 50% (w/w) 2-hydroxypropyl-β-cyclodextrin at a ratio of 1:2:1. [c]The cut-off latency was 60 seconds. [d]Dose administered (mg/kg); CDS 10 mg is equimolar to enkephalin 5 mg.

TABLE 8

Area under the latency change vs. time curve after i.v. administration of an enkephalin-CDS, enkephalin and vehicle[a,b,c]

| Treatment | $AUC_{0-240\ min}$ |
|---|---|
| A-CDS (10)[d] [Compound (64)] | 4897.80 ± 1011.63* |
| A-CDS (5) [Compound (64)] | 2528.70 ± 663.78** |
| Enkephalin (5) [DADLE] | 775.58 ± 273.20 |
| Vehicle Control | 692.36 ± 106.68 |

Compared to the control group, *p < 0.005 and **p < 0.05 (by student's t-test). [a]Data represent mean ± S.E. of 9–10 rats. [b]Vehicle consisted of DMSO, ethanol and 50% (w/w) 2-hydroxypropyl-β-cyclodextrin at a ratio of 1:2:1. [c]The cut-off latency was 60 seconds. [d]Dose administered (mg/kg); A-CDS 10 mg is equimolar to enkephalin 5 mg.

Another representative chemical delivery system (AA-CDS) of the invention for the enkephalin analog DADLE, namely compound (69) of EXAMPLE 69, which has an alanine-alanine spacer, was studied in the same rat tail flick test procedure described above to determine its analgesic effects compared to DADLE itself. AA-CDS was tested at a dose of 10 mg/2 ml/kg, which is equimolar to 5 mg/kg of DADLE, and compared with vehicle and 5mg/kg of DADLE exactly as described above. Each dose was tested in ten animals. Results are presented in Tables 9–12 below. It is apparent from these tables that the AA-CDS [Compound (69)], like the earlier tested A-CDS, produced a significant analgesic effect, while the corresponding "unpackaged" enkephalin, at an equimolar dose, did not differ from the control. It is also apparent that, in the case of the enkephalin derivatives, the CDS with a single alanine spacer was more effective than the CDS with an alanine-alanine spacer.

TABLE 9

Tail flick latency periods in rats prior to and after i.v. administration of an enkephalin-CDS, enkephalin and vehicle[a,b,c]

| | Tail flick latency periods, seconds[d] | | |
|---|---|---|---|
| Time, min | AA-CDS [Compound (69)] (10 mg/kg)[b] | Enkephalin [DADLE] (5 mg/kg) | Vehicle Control |
| 0[e] | 8.47 ± 0.76 | 7.97 ± 0.60 | 8.23 ± 0.52 |
| 5 | 29.78 ± 5.99* | 12.15 ± 1.53 | 15.16 ± 2.06 |
| 15 | 20.24 ± 5.07 | 12.67 ± 1.18 | 15.93 ± 3.69 |
| 30 | 20.41 ± 5.42 | 12.66 ± 1.70 | 10.43 ± 0.75 |
| 60 | 13.77 ± 2.01 | 15.75 ± 3.03 | 10.32 ± 0.63 |
| 120 | 11.81 ± 0.99 | 10.11 ± 1.29 | 11.24 ± 1.53 |
| 180 | 15.94 ± 1.89* | 10.94 ± 1.65 | 9.51 ± 0.71 |
| 240 | 13.99 ± 0.95 | 10.64 ± 1.68 | 12.61 ± 1.53 |
| 300 | 18.43 ± 4.52 | 10.02 ± 1.08 | —[f] |

*Compared to the control group, p < 0.02; **p < 0.005 (by student's t-test). [a]Data represent mean ± S.E. of 9–10 rats. [b]Equimolar dose to enkephalin 5 mg was administered. [c]Vehicle consisted of DMSO, ethanol and 50% (w/w) 2-hydroxypropyl-β-cyclodextrin at a ratio of 1:2:1. [d]The cut-off latency was 60 seconds. [e]Tail flick latency prior to drug administration. [f]Not determined.

TABLE 10

Number of animals responding to the treatment (in rat tail flick test)[a]

| | Number of Animals | | |
|---|---|---|---|
| Tail Flick Latency, seconds | AA-CDS [Compound (69)] (10 mg/kg)[a] | Enkephalin [DADLE] (5 mg/kg) | Vehicle Control |
| <20[b] | 3 | 7 | 7 |
| 20–40 | 2 | 3 | 2 |
| 40–60 | 2 | 0 | 0 |
| >60[c] | 2 | 0 | 0 |

[a]Equimolar dose to enkephalin 5 mg was administered. [b]Maximum tail flick latency. [c]The cut-off latency was 60 seconds.

TABLE 11

Maximum tail flick latency in rats after i.v. administration of an enkephalin-CDS, enkephalin and vehicle[a,b,c,d]

| Treatment | Maximum tail flick latency, seconds |
|---|---|
| AA-CDS [Compound (69)][d] | 34.27 ± 6.20** |
| Enkephalin [DADLE] | 19.68 ± 2.42 |
| Vehicle Control | 19.61 ± 2.99 |

Compared to the control group, *p < 0.001 and **p < 0.02 (by student's t-test). [a]Data represent mean ± S.E. of 9–10 rats. [b]Vehicle consisted of DMSO, ethanol and 50% (w/w) 2-hydroxypropyl-β-cyclodextrin at a ratio of 1:2:1. [c]The cut-off latency was 60 seconds. [d]Equimolar dose to enkephalin 5 mg was administered.

TABLE 12

Area under the latency change vs. time curve after i.v. administration of an enkephalin-CDS, enkephalin and vehicle[a,b,c,d]

| Treatment | $AUC_{0-240\ min}$ |
|---|---|
| AA-CDS [Compound (69)][d] | 1639.67 ± 266.61** |
| Enkephalin [DADLE] | 775.58 ± 273.20 |
| Vehicle Control | 692.36 ± 106.68 |

Compared to the control group, *p < 0.005 and **p < 0.05 (by student's t-test). [a]Data represent mean ± S.E. of 9–10 rats. [b]Vehicle consisted of DMSO, ethanol and 50% (w/w) 2-hydroxypropyl-β-cyclodextrin at a ratio of 1:2:1. [c]The cut-off latency was 60 seconds. [d]Equimolar dose to enkephalin 5 mg was administered.

The "packaged" peptides of formula (I) provided by the present invention are typically administered to mammals by incorporating the selected "packaged" peptide in a pharmaceutical composition comprising the peptide or a non-toxic pharmaceutically acceptable salt thereof and a non-toxic pharmaceutically acceptable carrier therefor. The peptide or its salt is employed in an effective amount, i.e., an amount sufficient to evoke the desired pharmacological response. Thus, for example, the enkephalin and kyotorphin derivatives of the invention will typically be employed in an analgesically effective amount; the LHRH agonist derivatives of the invention will typically be used in an amount sufficient to control LH or FSH or to have the desired effect on the reproductive system (e.g. one or more of the physiological and paradoxical utilities disclosed in Nestor et at. U.S. Pat. No. 4,530.920); the TRH type derivatives will be used in amounts sufficient to provoke an antidepressant effect or to improve memory; and so forth. Since the compounds of the invention are delivery systems for pharmacologically active peptides, they are typically used to provoke the type of pharmacological response which would be achieved if the peptides which they are designed to deliver were to be administered directly to the brain.

Suitable non-toxic pharmaceutically acceptable carriers for use with the selected peptide derivative of formula (I) will be apparent to those skilled in the art of pharmaceutical formulation. See, for example, *Remington's Pharmaceutical Sciences*, seventeenth edition, ed. Alfonso R. Gennaro, Mack Publishing Company, Easton, Pa. (1985). Obviously, the choice of suitable careers will depend upon the exact nature of the particular dosage form selected, as well as upon the identity of the "packed" peptide to be administered. The therapeutic dosage range can be estimated on the basis of animal tests, e.g., in the case of the LHRH agonist derivatives, on the basis of tests described in the Nestor et al. patent referred to hereinabove. Naturally, such therapeutic dosage ranges will vary with the particular compound of formula (I) used, the size, species and physical condition of the subject, the severity of the subject's medical condition, the particular dosage form employed, the route of administration and the like. And the quantity of given dosage form needed to deliver the desired dose will of course depend upon the concentration of the "packaged" peptide of formula (I) in any given pharmaceutical composition/dosage form thereof. Generally speaking, on a molar basis, the dosage levels of the "packaged" peptides needed to provoke the desired pharmacological response will be much lower than those needed of the corresponding "unpackaged" peptides.

In addition, the active ingredient may be formulated into a sustained release carrier system and/or a route of administration may be selected to slowly release the chemical, e.g., subcutaneous implantation or transdermal delivery.

Routes of administration contemplated for the "packaged" peptides of formula (I) and pharmaceutical compositions containing them are any of the routes generally used for treatment of the types of conditions for which the peptides are administered. These include parenteral (including intravenous, intramuscular and subcutaneous), vaginal, rectal, nasal, oral and buccal routes. Appropriate dosage forms for these routes of administration will be apparent to those skilled in the art; see, for example, Nestor et al. U.S. Pat. No. 4,530.920. While any of these routes of administration/dosage forms are contemplated for "packaged" peptides of formula (I), it is noted that the invention provides a unique advantage in providing a "packaged" form of peptides which previously could not be effectively administered orally in their "unpackaged" form because they would be rapidly deactivated in the gastrointestinal tract or the gut wall (e.g., by peptidases and proteases) prior to achieving their desired therapeutic function.

While the invention has been described in terms of various preferred embodiments, the skilled artisan will appreciate that various modifications, substitutions, omissions and changes may be made without departing from the spirit thereof. Accordingly, it is intended that the scope of the present invention be limited solely by the scope of the following claims and their equivalents.

What is claimed is:

1. A compound of the formula

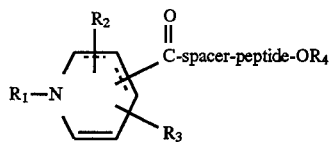

(I)

or a non-toxic pharmaceutically acceptable salt thereof, wherein:

$R_1$ is $C_1$–$C_7$ alkyl, $C_1$–$C_7$ haloalkyl or $C_7$–$C_{12}$ aralkyl;

$R_2$ and $R_3$, which are the same or different, are each selected from the group consisting of hydrogen, halo, cyano, $C_1$–$C_7$ alkyl, $C_1$–$C_7$ alkoxy, $C_2$–$C_8$ alkoxycarbonyl, $C_2$–$C_8$ alkanoyloxy, $C_1$–$C_7$ haloalkyl, $C_1$–$C_7$ alkylthio, $C_1$–$C_7$ alkylsulfinyl, $C_1$–$C_7$ alkylsulfonyl, —CH=NOR''' wherein R''' is hydrogen or $C_1$–$C_7$ alkyl, and —CONR'R'' wherein R' and R'', which are the same or different, are each hydrogen or $C_1$–$C_7$ alkyl;

or one of $R_2$ and $R_3$ together with the adjacent ring carbon atom forms a phenyl ring fused to the six-membered heterocyclic ring, which phenyl ring is unsubstituted or is substituted with one or two substituents, which are the same or different, selected from the group consisting of hydroxy, protected hydroxy, halo, cyano, $C_1$–$C_7$ alkyl, $C_1$–$C_7$ alkoxy, $C_2$–$C_8$ alkoxycarbonyl, $C_2$–$C_8$ alkanoyloxy, $C_1$–$C_7$ haloalkyl, $C_1$–$C_7$ alkylthio, $C_1$–$C_7$ alkylsulfinyl, $C_1$–$C_7$ alkylsulfonyl, —CH=NOR''' wherein R''' is hydrogen or $C_1$–$C_7$ alkyl, and —CONR'R'' wherein R' and R'', which are the same or different, are each hydrogen or $C_1$–$C_7$ alkyl;

the dotted lines represent a double bond in one of the two indicated positions, the depicted being a 1,4- or 1,6-dihydropyridine, a 1,4- or 1,2-dihydroquinoline, or a 1,2-dihydroisoquinoline;

"spacer" is an L-amino acid unit or a di- or tripeptide consisting of 2 or 3 L-amino acid units, the N-terminal amino acid of said spacer being bonded to the depicted carbonyl carbon via an amide bond;

and "peptide" is a pharmacologically active peptide having 2 to 20 amino acid units, the N-terminal amino acid of said peptide being bonded to the C-terminal amino acid of said spacer via a peptide bond, the C-terminal amino acid of said peptide having an esterified carboxyl function —COOR$_4$ wherein R$_4$ is $C_6$–$C_{30}$ polycycloalkyl-$C_pH_{2p}$— wherein p is 0, 1, 2 or 3, or $C_6$–$C_{30}$ polycycloalkenyl-$C_pH_{2p}$— wherein p is defined as above.

2. The compound according to claim 1, wherein $R_1$ is methyl.

3. The compound according to claim 1, wherein the depicted is a 1,4-dihydropyridine ring system.

4. The compound according to claim 1, wherein the depicted is a 1,6-dihydropyridine ring system.

5. The compound according to claim 1, wherein the depicted is a 1,4-dihydroquinoline ring system.

6. The compound according to claim 1, wherein the depicted is a 1,2-dihydroquinoline ring system.

7. The compound according to claim 1, wherein the depicted is a 1,2-dihydroisoquinoline ring system.

8. The compound according to claim 1, wherein

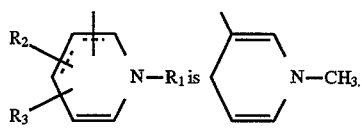

9. The compound according to claim 1, wherein "spacer" is an L-amino acid selected from the group consisting of alanine, proline, glycine and phenylalanine, or a dipeptide consisting of L-amino acid units selected from said group.

10. The compound according to claim 1, wherein "peptide" is kyotorphin.

11. The compound according to claim 1, wherein "peptide" is a TRH analog.

12. The compound according to claim 11, wherein the analog is Gln-Leu-Pro-Gly [SEQ ID No. 3].

13. The compound according to claim 1, wherein "peptide" is Met$^5$-enkephalin or Leu$^5$-enkephalin or an analog thereof.

14. The compound according to claim 13, wherein the analog is [D-Ala$^2$]-[D-Leu$^5$]-enkephalin.

15. The compound according to claim 1, wherein —COOR$_4$ represents the C-terminal carboxyl group of said peptide bonded in ester linkage to the hydroxyl group of a steroidal alcohol.

16. The compound according to claim 15, wherein R$_4$ is a radical of the formula

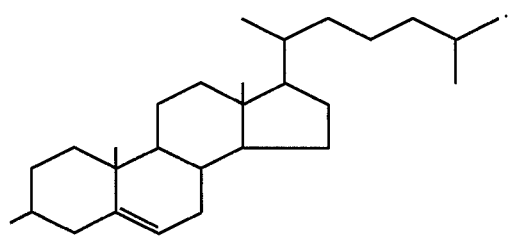

17. A compound of the formula

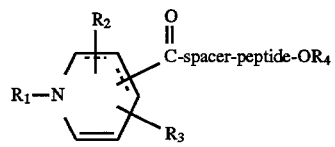

or a non-toxic pharmaceutically acceptable salt thereof, wherein:

R$_1$ is C$_1$–C$_7$ alkyl, C$_1$–C$_7$ haloalkyl or C$_7$–C$_{12}$ aralkyl;

R$_2$ and R$_3$, which are the same or different, are each selected from the group consisting of hydrogen, halo, cyano, C$_1$–C$_7$ alkyl, C$_1$–C$_7$ alkoxy, C$_2$–C$_8$ alkoxycarbonyl, C$_2$–C$_8$ alkanoyloxy, C$_1$–C$_7$ haloalkyl, C$_1$–C$_7$ alkylthio, C$_1$–C$_7$ alkylsulfinyl, C$_1$–C$_7$ alkylsulfonyl, —CH=NOR'" wherein R'" is hydrogen or C$_1$–C$_7$ alkyl, and —CONR'R" wherein R' and R", which are the same or different, are each hydrogen or C$_1$–C$_7$ alkyl;

or one of R$_2$ and R$_3$ together with the adjacent ring carbon atom forms a phenyl ring fused to the six-membered heterocyclic ring, which phenyl ring is unsubstituted or is substituted with one or two substituents, which are the same or different, selected from the group consisting of hydroxy, protected hydroxy, halo, cyano, C$_1$–C$_7$ alkyl, C$_1$–C$_7$ alkoxy, C$_2$–C$_8$ alkoxycarbonyl, C$_2$–C$_8$ alkanoyloxy, C$_1$–C$_7$ haloalkyl, C$_1$–C$_7$ alkylthio, C$_1$–C$_7$ alkylsulfinyl, C$_1$–C$_7$ alkylsulfonyl, —CH=NOR'" wherein R'" is hydrogen or C$_1$–C$_7$ alkyl, and —CONR'R" wherein R' and R", which are the same or different, are each hydrogen or C$_1$–C$_7$ alkyl;

the dotted lines represent a double bond in one of the two indicated positions, the depicted ring system being a 1,4- or 1,6-dihydropyridine, a 1,4- or 1,2-dihydroquinoline, or a 1,2-dihydroisoquinoline;

"spacer" is an L-amino acid selected from the group consisting of alanine and proline, or a dipeptide consisting of L-amino acid units selected from said group, the N-terminal amino acid of said spacer being bonded to the depicted carbonyl carbon via an amide bond;

and "peptide" is a pharmacologically active peptide having 2 to 20 amino acid units, the N-terminal amino acid of said peptide being bonded to the C-terminal amino acid of said spacer via a peptide bond, the C-terminal amino acid of said peptide having an esterified carboxyl function —COOR$_4$ wherein R$_4$ is C$_6$–C$_{30}$ polycycloalkyl-C$_p$H$_{2p}$— wherein p is 0, 1, 2 or 3, or C$_6$–C$_{30}$ polycycloalkenyl-C$_p$H$_{2p}$— wherein p is defined as above.

18. The compound according to claim 17, wherein R$_1$ is methyl.

19. The compound according to claim 17, wherein the depicted ring system is a 1,4-dihydropyridine.

20. The compound according to claim 17, wherein the depicted ring system is a 1,6-dihydropyridine.

21. The compound according to claim 17, wherein the depicted ring system is a 1,4-dihydroquinoline.

22. The compound according to claim 17, wherein the depicted ring system is a 1,2-dihydroquinoline.

23. The compound according to claim 17, wherein the depicted ring system is a 1,2-dihydroisoquinoline.

24. The compound according to claim 17, wherein

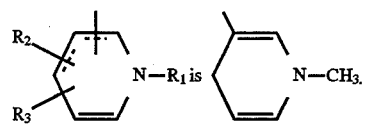

25. The compound according to claim 17, wherein "peptide" is kyotorphin.

26. The compound according to claim 17, wherein "peptide" is a TRH analog.

27. The compound according to claim 26, wherein the analog is Gln-Leu-Pro-Gly [SEQ ID NO. 3].

28. The compound according to claim 17, wherein "peptide" is Met$^5$-enkephalin or Leu$^5$-enkephalin or an analog thereof.

29. The compound according to claim 28, wherein the analog is [D-Ala$^2$]-[D-Leu$^5$]-enkephalin.

30. A compound of the formula

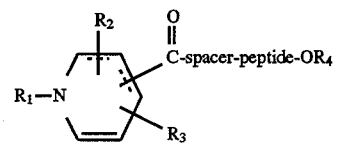

or a non-toxic pharmaceutically acceptable salt thereof, wherein:

$R_1$ is $C_1$-$C_7$ alkyl, $C_1$-$C_7$ haloalkyl or $C_7$-$C_{12}$ aralkyl;

$R_2$ and $R_3$, which are the same or different, are each selected from the group consisting of hydrogen, halo, cyano, $C_1$-$C_7$ alkyl, $C_1$-$C_7$ alkoxy, $C_2$-$C_8$ alkoxycarbonyl, $C_2$-$C_8$ alkanoyloxy, $C_1$-$C_7$ haloalkyl, $C_1$-$C_7$ alkylthio, $C_1$-$C_7$ alkylsulfinyl, $C_1$-$C_7$ alkylsulfonyl, —CH=NOR''' wherein R''' is hydrogen or $C_1$-$C_7$ alkyl, and —CONR'R'' wherein R' and R'', which are the same or different, are each hydrogen or $C_1$-$C_7$ alkyl;

or one of $R_2$ and $R_3$ together with the adjacent ring carbon atom forms a phenyl ring fused to the six-membered heterocyclic ring, which phenyl ring is unsubstituted or is substituted with one or two substituents, which are the same or different, selected from the group consisting of hydroxy, protected hydroxy, halo, cyano, $C_1$-$C_7$ alkyl, $C_1$-$C_7$ alkoxy, $C_2$-$C_8$ alkoxycarbonyl, $C_2$-$C_8$ alkanoyloxy, $C_1$-$C_7$ haloalkyl, $C_1$-$C_7$ alkylthio, $C_1$-$C_7$ alkylsulfinyl, $C_1$-$C_7$ alkylsulfonyl, —CH=NOR''' wherein R''' is hydrogen or $C_1$-$C_7$ alkyl, and —CONR'R'' wherein R' and R'', which are the same or different, are each hydrogen or $C_1$-$C_7$ alkyl;

the dotted lines represent a double bond in one of the two indicated positions, the depicted ring system being a 1,4- or 1,6-dihydropyridine, a 1,4- or 1,2-dihydroquinoline, or a 1,2-dihydroisoquinoline ring system;

"spacer" is an L-amino acid selected from the group consisting of alanine and proline, or a dipeptide consisting of L-amino acid units selected from said group, the N-terminal amino acid of said spacer being bonded to the depicted carbonyl carbon via an amide bond:

and "peptide" is a pharmacologically active peptide having 2 to 20 amino acid units, the N-terminal amino acid of said peptide being bonded to the C-terminal amino acid of said spacer via a peptide bond, the C-terminal amino acid of said peptide having an esterified carboxyl function —COOR$_4$ wherein —OR$_4$ represents a steroidal alcohol, less a hydrogen atom on the hydroxyl group.

31. The compound according to claim 30, wherein $R_4$ is a radical of the formula

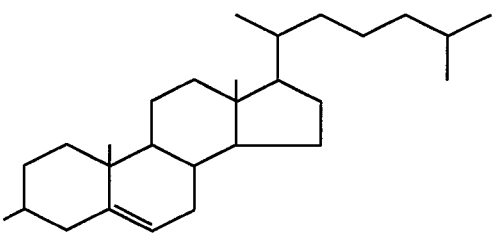

32. The compound according to claim 31, having the formula [SEQ ID NO. 35]

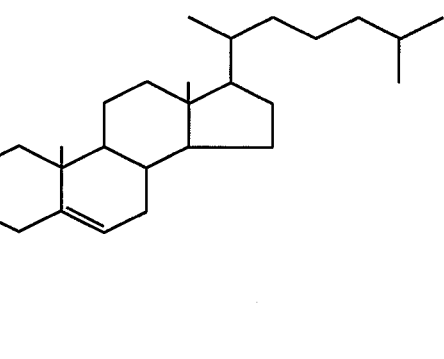

33. The compound according to claim 31, having the formula [SEQ ID NO. 41]

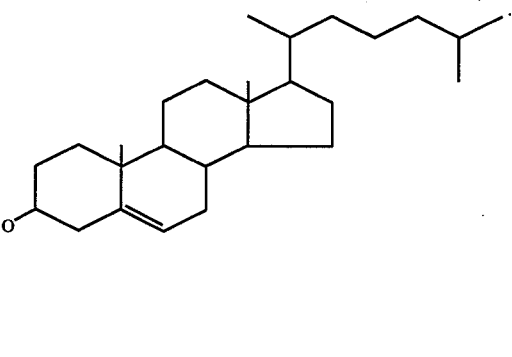

34. The compound according to claim 31, having the formula [SEQ ID NO. 54]
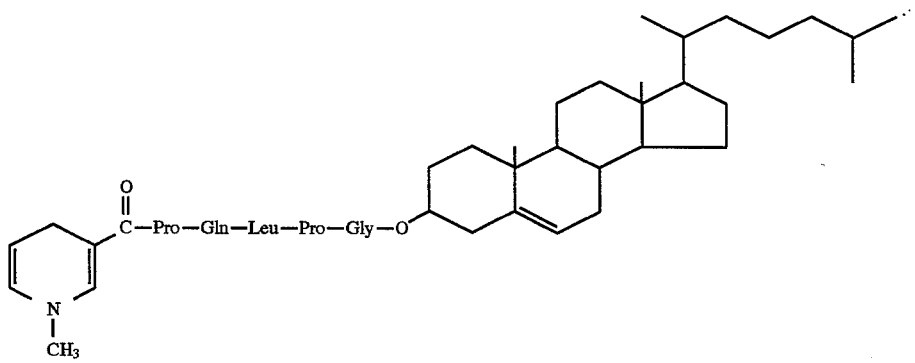
35. The compound according to claim 31, having the formula [SEQ ID NO. 56]
36. The compound according to claim 31, having the formula [SEQ ID NO. 58]
37. The compound according to claim 31, having the formula

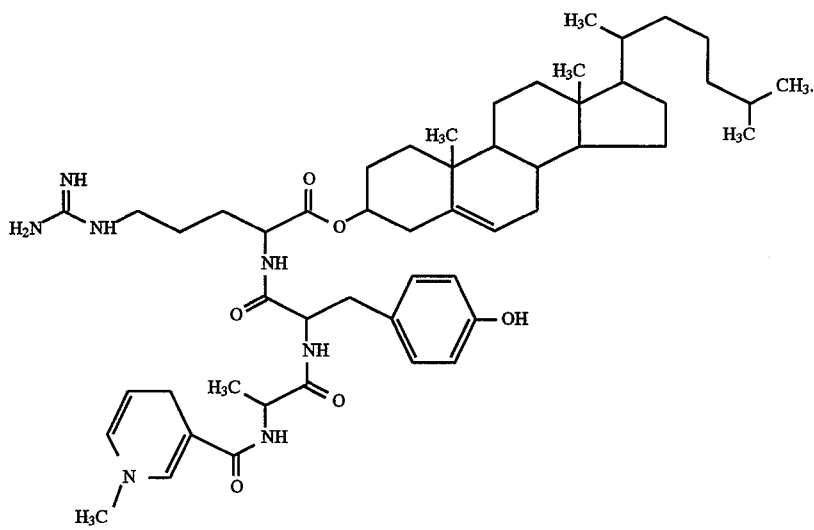
38. The compound according to claim 31, having the formula [SEQ ID NO. 62]
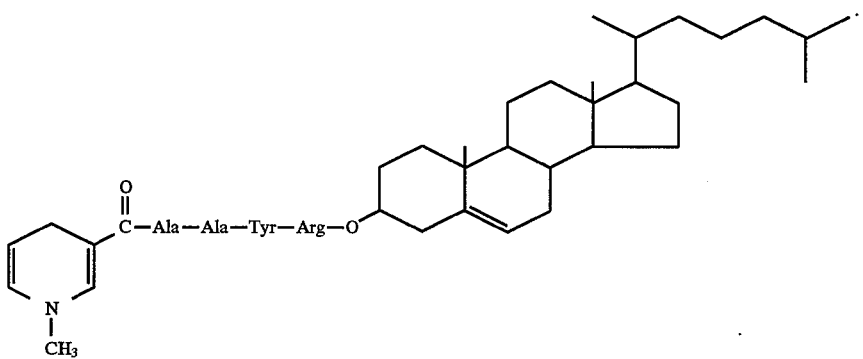
39. The compound according to claim 31, having the structural formula [SEQ ID NO. 81]
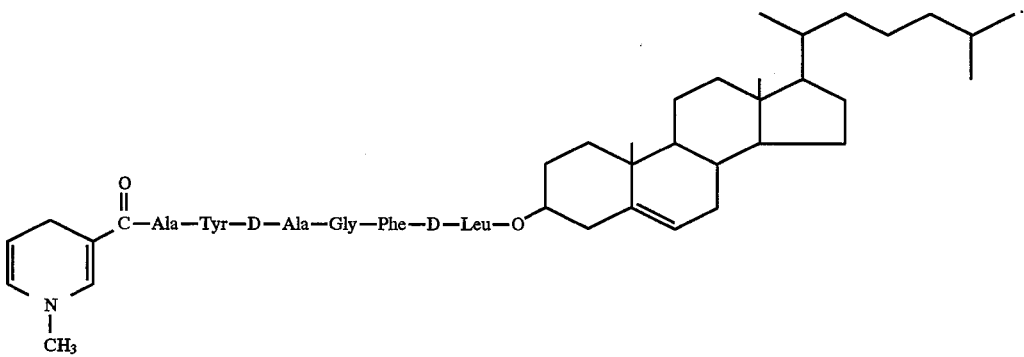
40. The compound according to claim 31, having the formula [SEQ ID NO. 86]

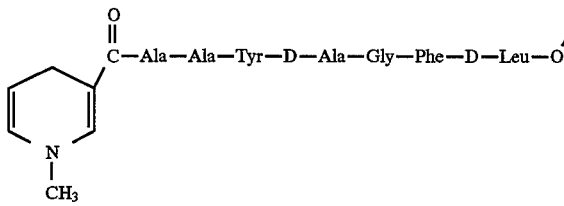
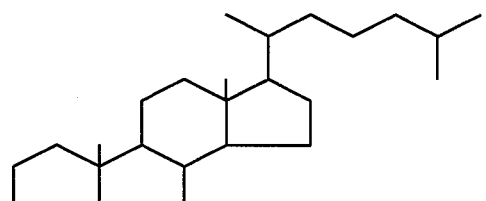

41. A quaternary salt of the formula

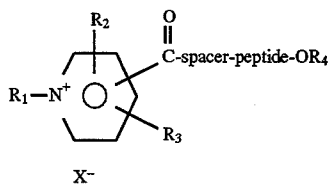

wherein:

$R_1$ is $C_1$–$C_7$ alkyl, $C_1$–$C_7$ haloalkyl or $C_7$–$C_{12}$ aralkyl;

$R_2$ and $R_3$, which are the same or different, are each selected from the group consisting of hydrogen, halo, cyano, $C_1$–$C_7$ alkyl, $C_1$–$C_7$ alkoxy, $C_2$–$C_8$ alkoxycarbonyl, $C_2$–$C_8$ alkanoyloxy, $C_1$–$C_7$ haloalkyl, $C_1$–$C_7$ alkylthio, $C_1$–$C_7$ alkylsulfinyl, $C_1$–$C_7$ alkylsulfonyl, —CH=NOR''' wherein R''' is hydrogen or $C_1$–$C_7$ alkyl, and —CONR'R'' wherein R' and R'', which are the same or different, are each hydrogen or $C_1$–$C_7$ alkyl;

or one of $R_2$ and $R_3$ together with the adjacent ring carbon atom forms a phenyl ring fused to the six-membered heterocyclic ring, which phenyl ring is unsubstituted or is substituted with one or two substituents, which are the same or different, selected from the group consisting of hydroxy, protected hydroxy, halo, cyano, $C_1$–$C_7$ alkyl, $C_1$–$C_7$ alkoxy, $C_2$–$C_8$ alkoxycarbonyl, $C_2$–$C_8$ alkanoyloxy, $C_1$–$C_7$ haloalkyl, $C_1$–$C_7$ alkylthio, $C_1$–$C_7$ alkylsulfinyl, $C_1$–$C_7$ alkylsulfonyl, —CH=NOR''' wherein R''' is hydrogen or $C_1$–$C_7$ alkyl, and —CONR'R'' wherein R' and R'', which are the same or different, are each hydrogen or $C_1$–$C_7$ alkyl;

the depicted is a pyridinium, quinolinium or isoquinolinium ion;

"spacer" is an L-amino acid unit or a di- or tripeptide consisting of 2 or 3 L-amino acid units, the N-terminal amino acid of said spacer being bonded to the depicted carbonyl carbon via an amide bond;

"peptide" is a pharmacologically active peptide having 2 to 20 amino acid units, the N-terminal amino acid of said peptide being bonded to the C-terminal amino acid of said spacer via a peptide bond, the C-terminal amino acid of said peptide having an esterified carboxyl function —COOR$_4$ wherein R$_4$ is $C_6$–$C_{30}$ polycycloalkyl-$C_pH_{2p}$— wherein p is 0, 1, 2 or 3, or $C_6$–$C_{30}$ polycycloalkenyl —$C_pH_{2p}$— wherein p is defined as above;

and X$^-$ is the anion of a non-toxic, pharmaceutically acceptable acid.

42. The salt according to claim 42, wherein $R_1$ is methyl.

43. The salt according to claim 42, wherein the depicted ring system is a pyridinium ion.

44. The salt according to claim 41, wherein the depicted ring system is a quinolinium ion.

45. The salt according to claim 41, wherein the depicted ring system is an isoquinolinium ion.

46. The salt according to claim 41, wherein

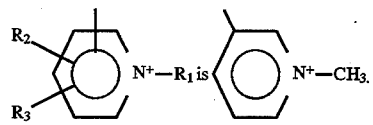

47. The salt according to claim 41, wherein "spacer" is an L-amino acid selected from the group consisting of alanine, proline, glycine and phenylalanine, or a dipeptide consisting of L-amino acid units selected from said group.

48. The salt according to claim 41, wherein "peptide" is kyotorphin.

49. The salt according to claim 41, wherein "peptide" is a TRH analog.

50. The salt according to claim 49, wherein the analog is Gln-Leu-Pro-Gly [SEQ ID NO. 3].

51. The salt according to claim 41, wherein "peptide" is Met$^5$-enkephalin or Leu$^5$-enkephalin or an analog thereof.

52. The salt according to claim 51, wherein the analog is [D-Ala$^2$]-[D-Leu$^5$]-enkephalin.

53. The salt according to claim 41, wherein —COOR$_4$ represents the C-terminal carboxyl group of said peptide bonded in ester linkage to the hydroxyl group of a steroidal alcohol.

54. The salt according to claim 53, wherein R$_4$ is a radical of the formula

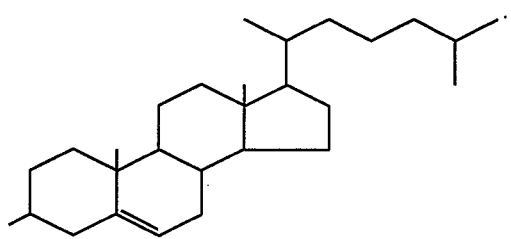

55. A quaternary salt of the formula

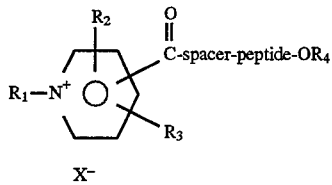

wherein:

$R_1$ is $C_1-C_7$ alkyl, $C_1-C_7$ haloalkyl or $C_7-C_{12}$ aralkyl;

$R_2$ and $R_3$, which are the same or different, are each selected from the group consisting of hydrogen, halo, cyano, $C_1-C_7$ alkyl, $C_1-C_7$ alkoxy, $C_2-C_8$ alkoxycarbonyl, $C_2-C_8$ alkanoyloxy, $C_1-C_7$ haloalkyl, $C_1-C_7$ alkylthio, $C_1-C_7$ alkylsulfinyl, $C_1-C_7$ alkylsulfonyl, —CH=NOR''' wherein R''' is hydrogen or $C_1-C_7$ alkyl, and —CONR'R'' wherein R' and R'', which are the same or different, are each hydrogen or $C_1-C_7$ alkyl;

or one of $R_2$ and $R_3$ together with the adjacent ring carbon atom forms a phenyl ring fused to the six-membered heterocyclic ring, which phenyl ring is unsubstituted or is substituted with one or two substituents, which are the same or different, selected from the group consisting of hydroxy, protected hydroxy, halo, cyano, $C_1-C_7$ alkyl, $C_1-C_7$ alkoxy, $C_2-C_8$ alkoxycarbonyl, $C_2-C_8$ alkanoyloxy, $C_1-C_7$ haloalkyl, $C_1-C_7$ alkylthio, $C_1-C_7$ alkylsulfinyl, $C_1-C_7$ alkylsulfonyl, —CH=NOR''' wherein R''' is hydrogen or $C_1-C_7$ alkyl, and —CONR'R'' wherein R' and R'', which are the same or different, are each hydrogen or $C_1-C_7$ alkyl;

the depicted ring system is a pyridinium, quinolinium or isoquinolinium ion;

"spacer" is an L-amino acid selected from the group consisting of alanine and proline, or a dipeptide consisting of L-amino acid units selected from said group, the N-terminal amino acid of said spacer being bonded to the depicted carbonyl carbon via an amide bond;

"peptide" is a pharmacologically active peptide having 2 to 20 amino acid units, the N-terminal amino acid of said peptide being bonded to the C-terminal amino acid of said spacer via a peptide bond, the C-terminal amino acid of said peptide having an esterified carboxyl function —COOR$_4$ wherein R$_4$ is $C_6-C_{30}$ polycycloalkyl-$C_pH_{2p}$— wherein p is 0, 1, 2 or 3, or $C_6-C_{30}$ polycycloalkenyl —$C_pH_{2p}$— wherein p is defined as above;

and $X^-$ is the anion of a non-toxic, pharmaceutically acceptable acid.

56. The salt according to claim 55, wherein R$_1$ is methyl.

57. The salt according to claim 55, wherein the depicted ring system is a pyridinium ion.

58. The salt according to claim 55, wherein the depicted ring system is a quinolinium ion.

59. The salt according to claim 55, wherein the depicted ring system is an isoquinolinium ion.

60. The salt according to claim 55, wherein

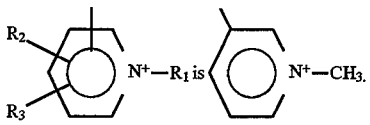

61. The salt according to claim 55, wherein "peptide" is kyotorphin.

62. The salt according to claim 55, wherein "peptide" is a TRH analog.

63. The salt according to claim 62, wherein the analog is Gln-Leu-Pro-Gly [SEQ ID NO. 3].

64. The salt according to claim 55, wherein "peptide" is Met$^5$-enkephalin or Leu$^5$-enkephalin or an analog thereof.

65. The salt according to claim 64, wherein the analog is [D-Ala$^2$]-[D-Leu$^5$]-enkephalin.

66. A quaternary salt of the formula

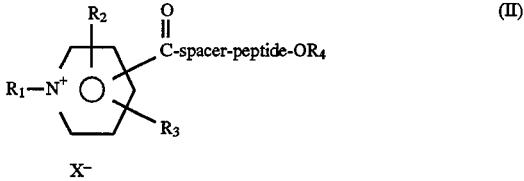

wherein:

$R_1$ is $C_1-C_7$ alkyl, $C_1-C_7$ haloalkyl or $C_7-C_{12}$ aralkyl;

$R_2$ and $R_3$, which are the same or different, are each selected from the group consisting of hydrogen, halo, cyano, $C_1-C_7$ alkyl, $C_1-C_7$ alkoxy, $C_2-C_8$ alkoxycarbonyl, $C_2-C_8$ alkanoyloxy, $C_1-C_7$ haloalkyl, $C_1-C_7$ alkylthio, $C_1-C_7$ alkylsulfinyl, $C_1-C_7$ alkylsulfonyl, —CH=NOR''' wherein R''' is hydrogen or $C_1-C_7$ alkyl, and —CONR'R'' wherein R' and R'', which are the same or different, are each hydrogen or $C_1-C_7$ alkyl;

or one of $R_2$ and $R_3$ together with the adjacent ring carbon atom forms a phenyl ring fused to the six-membered heterocyclic ring, which phenyl ring is unsubstituted or is substituted with one or two substituents, which are the same or different, selected from the group consisting of hydroxy, protected hydroxy, halo, cyano, $C_1-C_7$ alkyl, $C_1-C_7$ alkoxy, $C_2-C_8$ alkoxycarbonyl, $C_2-C_8$ alkanoyloxy, $C_1-C_7$ haloalkyl, $C_1-C_7$ alkylthio, $C_1-C_7$ alkylsulfinyl, $C_1-C_7$ alkylsulfonyl, —CH=NOR''' wherein R''' is hydrogen or $C_1-C_7$ alkyl, and —CONR'R'' wherein R' and R'', which are the same or different, are each hydrogen or $C_1-C_7$ alkyl;

the depicted ring system is a pyridinium, quinolinium or isoquinolinium ion;

"spacer" is an L-amino acid selected from the group consisting of alanine and proline, or a dipeptide consisting of L-amino acid units selected from said group, the N-terminal amino acid of said spacer being bonded to the depicted carbonyl carbon via an amide bond;

"peptide" is a pharmacologically active peptide having 2 to 20 amino acid units, the N-terminal amino acid of said peptide being bonded to the C-terminal amino acid of said spacer via a peptide bond, the C-terminal amino acid of said peptide having an esterified carboxyl function —COOR$_4$ wherein —OR$_4$ represents a steroidal alcohol, less a hydrogen atom on the hydroxyl group;

and X$^-$ is the anion of a non-toxic, pharmaceutically acceptable acid.

67. The salt according to claim 66, wherein R$_4$ is a radical of the formula

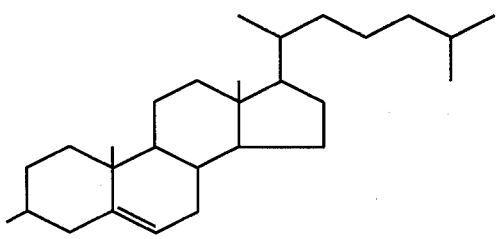

* * * * *